(12) United States Patent
Vodyanyk et al.

(10) Patent No.: US 12,163,155 B2
(45) Date of Patent: Dec. 10, 2024

(54) ANTIGEN-SPECIFIC IMMUNE EFFECTOR CELLS

(71) Applicant: FUJIFILM Cellular Dynamics, Inc., Madison, WI (US)

(72) Inventors: Maksym A. Vodyanyk, Madison, WI (US); Xin Zhang, Madison, WI (US); Andrew J. Brandl, Madison, WI (US); Deepika Rajesh, Madison, WI (US); Bradley Swanson, Madison, WI (US); Christie Munn, Madison, WI (US); Sarah Burton, Madison, WI (US); Wen Bo Wang, Madison, WI (US); Ethan McLEOD, Madison, WI (US)

(73) Assignee: FUJIFILM Cellular Dynamics, Inc., Madison, WI (US)

( * ) Notice: Subject to any disclaimer, the term of this patent is extended or adjusted under 35 U.S.C. 154(b) by 576 days.

(21) Appl. No.: 16/606,120

(22) PCT Filed: Apr. 18, 2018

(86) PCT No.: PCT/US2018/028133
§ 371 (c)(1),
(2) Date: Oct. 17, 2019

(87) PCT Pub. No.: WO2018/195175
PCT Pub. Date: Oct. 25, 2018

(65) Prior Publication Data
US 2020/0123501 A1    Apr. 23, 2020

Related U.S. Application Data
(60) Provisional application No. 62/486,875, filed on Apr. 18, 2017.

(51) Int. Cl.
| | | |
|---|---|---|
| *C12N 5/0783* | (2010.01) | |
| *A61K 35/17* | (2015.01) | |
| *A61K 35/545* | (2015.01) | |
| *C07K 14/725* | (2006.01) | |

(52) U.S. Cl.
CPC ............ *C12N 5/0636* (2013.01); *A61K 35/17* (2013.01); *A61K 35/545* (2013.01); *C07K 14/7051* (2013.01); *C12N 5/0646* (2013.01); *C07K 2317/622* (2013.01); *C07K 2319/03* (2013.01); *C07K 2319/33* (2013.01); *C12N 2501/01* (2013.01); *C12N 2501/115* (2013.01); *C12N 2501/125* (2013.01); *C12N 2501/145* (2013.01); *C12N 2501/155* (2013.01); *C12N 2501/165* (2013.01); *C12N 2501/2303* (2013.01); *C12N 2501/2306* (2013.01); *C12N 2501/2311* (2013.01); *C12N 2501/26* (2013.01); *C12N 2501/727* (2013.01); *C12N 2501/91* (2013.01); *C12N 2506/11* (2013.01); *C12N 2510/00* (2013.01)

(58) Field of Classification Search
CPC ............... C12N 5/0636; C12N 5/0646; C12N 2501/01; C12N 2501/115; C12N 2501/125; C12N 2501/145; C12N 2501/155; C12N 2501/165; C12N 2501/2303; C12N 2501/2306; C12N 2501/2311; C12N 2501/26; C12N 2501/727; C12N 2501/91; C12N 2506/11; C12N 2510/00; C12N 5/0606; A61K 35/17; A61K 35/545; C07K 14/7051; C07K 2317/622; C07K 2319/03; C07K 2319/33
See application file for complete search history.

(56) References Cited

U.S. PATENT DOCUMENTS

| | | |
|---|---|---|
| 5,486,359 A | 1/1996 | Caplan et al. |
| 5,556,954 A | 9/1996 | Burn et al. |
| 5,843,780 A | 12/1998 | Thomson |
| 5,908,782 A | 6/1999 | Marshak et al. |
| 6,200,806 B1 | 3/2001 | Thomson |
| 6,482,926 B1 | 11/2002 | Thomas et al. |
| 7,029,913 B2 | 4/2006 | Thomson |
| 7,259,011 B2 | 8/2007 | Paul et al. |
| 7,442,548 B2 | 10/2008 | Thomson et al. |
| 8,058,065 B2 | 11/2011 | Yamanaka et al. |
| 8,071,369 B2 | 12/2011 | Jaenisch et al. |
| 8,129,187 B2 | 3/2012 | Yamanaka et al. |
| 8,183,038 B2 | 5/2012 | Thomson et al. |

(Continued)

FOREIGN PATENT DOCUMENTS

| | | |
|---|---|---|
| AU | 2015200413 | 2/2015 |
| CN | 105358680 | 2/2016 |

(Continued)

OTHER PUBLICATIONS

Shukla et al ("Progenitor T-cell differentiation from hematopoietic stem cells using Delta-like-4 and VCAM-1," Nature Methods, vol. 14 No. 5 May 2017 531, published online Apr. 10, 2017) (Year: 2017).*

Peled et al ("Nicotinamide, a SIRT1 inhibitor, inhibits differentiation and facilitates expansion of hematopoietic progenitor cells with enhanced bone marrow homing and engraftment," Experimental Hematology 2012;40:342-355) (Peled). (Year: 2012).*

(Continued)

*Primary Examiner* — Anoop K Singh
*Assistant Examiner* — David A Montanari
(74) *Attorney, Agent, or Firm* — Parker Highlander PLLC

(57) ABSTRACT

Provided herein are methods for the production of antigen-specific effector T cells and NK cells from pluripotent stem cells which express a chimeric antigen receptor (CAR). Further provided herein are methods for the adoptive cell therapy by administering the effector T cells and/or NK cells provided herein.

22 Claims, 16 Drawing Sheets

(56) References Cited

U.S. PATENT DOCUMENTS

| | | |
|---|---|---|
| 8,268,620 B2 | 9/2012 | Thomson et al. |
| 8,323,966 B2 | 12/2012 | Lebkowski et al. |
| 8,372,642 B2 | 2/2013 | Rajesh et al. |
| 8,546,140 B2 | 10/2013 | Mack et al. |
| 8,691,574 B2 | 4/2014 | Mack |
| 8,741,648 B2 | 6/2014 | Rajesh et al. |
| 8,900,871 B2 | 12/2014 | Okita et al. |
| 9,040,039 B2 | 5/2015 | Klimanskaya |
| 9,040,770 B2 | 5/2015 | Klimanskaya |
| 9,127,256 B2 | 9/2015 | Fusaki et al. |
| 9,175,268 B2 | 11/2015 | Mack |
| 9,206,389 B2 | 12/2015 | Lazzari et al. |
| 9,206,394 B2 | 12/2015 | Nakauchi et al. |
| 2002/0055144 A1 | 5/2002 | Wei et al. |
| 2003/0211603 A1 | 11/2003 | Earp et al. |
| 2006/0084168 A1 | 4/2006 | Thomson et al. |
| 2007/0077654 A1 | 4/2007 | Thomson et al. |
| 2008/0299095 A1 | 12/2008 | Humphries et al. |
| 2009/0068742 A1 | 3/2009 | Yamanaka |
| 2009/0148425 A1 | 6/2009 | Ohmori et al. |
| 2009/0246875 A1 | 10/2009 | Yamanaka et al. |
| 2010/0105137 A1 | 4/2010 | Takahashi et al. |
| 2010/0210014 A1 | 8/2010 | Yamanaka |
| 2010/0279403 A1 | 11/2010 | Rajesh et al. |
| 2011/0104125 A1 | 5/2011 | Yu |
| 2011/0287538 A1 | 11/2011 | Fusaki et al. |
| 2012/0009676 A1* | 1/2012 | Mack ............... C12N 15/85 435/372 |
| 2012/0135525 A1* | 5/2012 | Brown ............... C12N 15/85 435/377 |
| 2012/0276636 A1 | 11/2012 | Yamanaka et al. |
| 2013/0149284 A1 | 6/2013 | Malcuit et al. |
| 2013/0196369 A1 | 8/2013 | Hikita et al. |
| 2013/0210150 A1 | 8/2013 | Ban et al. |
| 2013/0224156 A1 | 8/2013 | Takahashi et al. |
| 2013/0280809 A1 | 10/2013 | Efe et al. |
| 2014/0037600 A1* | 2/2014 | Yu ..................... A61K 35/28 435/325 |
| 2014/0220681 A1 | 8/2014 | Valamehr et al. |
| 2014/0273211 A1 | 9/2014 | Sluvkin et al. |
| 2014/0315304 A1 | 10/2014 | Brown et al. |
| 2014/0322808 A1 | 10/2014 | Keller et al. |
| 2015/0086512 A1 | 3/2015 | Malcuit et al. |
| 2015/0159134 A1 | 6/2015 | Choudhray et al. |
| 2015/0175964 A1 | 6/2015 | Clegg et al. |
| 2015/0191697 A1 | 7/2015 | Stankewicz et al. |
| 2016/0009813 A1 | 1/2016 | Themeli et al. |
| 2016/0257939 A1 | 9/2016 | Brown et al. |
| 2016/0280809 A1 | 9/2016 | Stoerkle et al. |
| 2017/0067017 A1 | 3/2017 | Meyer et al. |
| 2017/0107492 A1 | 4/2017 | Yu et al. |
| 2018/0072992 A1 | 3/2018 | Valamehr et al. |
| 2018/0258388 A1 | 9/2018 | Ando et al. |
| 2018/0305664 A1 | 10/2018 | Vodyanyk et al. |
| 2019/0169569 A1 | 6/2019 | Bharti et al. |
| 2020/0263139 A1 | 8/2020 | Vodyanyk et al. |
| 2021/0017494 A1 | 1/2021 | Vodyanyk et al. |

FOREIGN PATENT DOCUMENTS

| | | |
|---|---|---|
| EP | 1507865 | 7/2008 |
| JP | 2013-53)2492 | 8/2013 |
| WO | WO 1996/039487 | 12/1996 |
| WO | WO 2006/020889 | 2/2006 |
| WO | WO 2006/050330 | 5/2006 |
| WO | WO 2007/069666 | 6/2007 |
| WO | WO 2009/135206 | 11/2009 |
| WO | WO 2009/137624 | 11/2009 |
| WO | WO 2010/008054 | 1/2010 |
| WO | WO 2010/099539 | 9/2010 |
| WO | WO 2011/063005 | 5/2011 |
| WO | WO 2012/019122 | 2/2012 |
| WO | WO 2012/029770 | 3/2012 |
| WO | WO 2012/109208 | 8/2012 |
| WO | WO 2013/039792 | 3/2013 |
| WO | WO 2013/114360 | 8/2013 |
| WO | WO 2014/121077 | 8/2014 |
| WO | WO 2014/153069 | 9/2014 |
| WO | WO 2014-165663 | 10/2014 |
| WO | WO 2014/165707 | 10/2014 |
| WO | WO 2015/054526 | 4/2015 |
| WO | WO 2015/087231 | 6/2015 |
| WO | WO 2015/164740 | 10/2015 |
| WO | WO 2016/115407 | 7/2016 |
| WO | WO 2017/070337 | 4/2017 |
| WO | WO 2017/079673 | 5/2017 |
| WO | WO 2017/088012 | 6/2017 |
| WO | WO 2017/100403 | 6/2017 |

OTHER PUBLICATIONS

Galat et al ("Cytokine-free directed differentiation of human pluripotent stem cells efficiently produces hemogenic endothelium with lymphoid potential," Stem Cell Research & Therapy vol. 8, Article No. 67 (Mar. 17, 2017) (Year: 2017).*
Chen et al ("Ex vivo expansion of dendritic-cell-activated antigen-specific CD4+ T cells with anti-CD3/CD28, interleukin-7, and interleukin-15: Potential for adoptive T cell immunotherapy," Clinical Immunology (2006) 119, 21-31) (Year: 2006).*
Office Action issued in Japanese Application No. 2019-556588, mailed May 24, 2022, and English translation thereof.
Shin et al., "Contractile forces sustain and polarize hematopoiesis from stem and progenitor cells," *Cell Stem Cell*, 14(1):81-93, 2014.
Abboud et al., "Hydrophobic adsorption chromatography of colony-stimulating activities and erythroid-enhancing activity from the human monocyte-like cell line, GCT," *Blood*, 58:1148-1154, 1981.
Akkina et al., "High-efficiency gene transfer into CD34+ cells with a human immunodeficiency virus type 1-based retroviral vector pseudotyped with vesicular stomatitis virus envelope glycoprotein G," *J. Virol.*, 70:2581-2585, 1996.
Amedola et al., "Coordinate dual-gene transgenesis by lentiviral vectors carrying synthetic bidirectional promoters," *Nature Biotechnology*, 23(1):108-116, 2005.
Amit et al., "Clonally Derived Human Embryonic Stem Cell Lines Maintain Pluripotency and Proliferative Potential for Prolonged Periods of Culture," *Develop. Biol.*, 227:271-278, 2000.
Aoki et al., "Regualtion of DNA Demethylation during Maturation of CD4+ Native T Cells by the Conserved Noncoding Sequence 1," *J. Immunol.*, 182:7698-7707, 2009.
Ayllon et al., "The Notch ligand DLL4 specifically marks human hematoendothelial progenitors and regulates their hematopoietic fate," *Leukemia*, 29(8):1741-1753, 2015.
Batta et al., "Direct Reprogramming of Murine Fibroblasts to Hematopoietic Progenitor Cells," *Cell Rep.*, 9(5):1871-1884, 2014.
Bauer et al., "Reawakening fetal hemoglobin: prospects for new therapies for the β-globin disorders," *Blood*, 120(15):2945-2953, 2012.
Bharti et al., "The new paradigm: retinal pigment epithelium cells generated from embryonic or induced pluripotent stem cells." Pigment Cell Melanoma Res. 24: 21-34 (published online Sep. 15, 2010).
Bhatnagar, et al. "Genetic and pharmacological reactivation of the mammalian inactive X chromosome," *Proc. Natl. Acad. Sci. USA*, 111(35):12591-8, 2014.
Bird, "The methyl-CpG-binding protein MeCP2 and neurological disease," *Biochem. Soc. Trans.*, 36:575-583, 2008.
Biswas et al., "Diagnostic application of polymerase chain reaction for detection of Ehrlichia risticii in equine monocytic ehrlichiosis (Potomac horse fever)," *J. Clin. Microbiol.*, 29:2228-2233, 1991.
Biswas et al., "Gene amplification by polymerase chain reaction for detection of Ehrlichia risticii DNA in Potomac horse fever," *Annals NY Acad. Sci.*, 590:582-583, 1990.
Buckholz et al., "Derivation of functional retinal pigment epithelium from induced pluripotent stem cells," Stem Cells, 29(9): 1391-1404, 2011.
Byrne, J. A., et al. "Producing primate embryonic stem cells by somatic cell nuclear transfer." Nature 450.7169 (2007): 497.

(56) References Cited

OTHER PUBLICATIONS

Carrio et al., "DNA methylation dynamics in muscle development and disease," *Front. Aging Neurosci.*, 7(19), 12 pages, 2015.
Chang et al., "Broad T-cell receptor repertoire in T-lymphocytes derived from human induced pluripotent stem cells," *PLOS ONE*, 9(5):e97335, 2014.
Chen et al., "Development of hematopoietic stem and progenitor cells from human pluripotent stem cells," *Journal of Cellular Biochemistry*, 116(7):1179-1189, 2015.
Cheng et al., "Self-Renewing Endodermal Progenitor Lines Generated from Human Pluripotent Stem Cells," *Cell Stem Cell*, 10(4):371-384, 2012.
Choi et al., "Hematopoietic differentiation and production of mature myeloid cells from human pluripotent stem cells," *Nature Protocols*, 6(3):296-313, 2011.
Chung et al., "Undifferentiated hematopoietic cells are characterized by a genome-wide undermethylation dip around the transcription start site and a hierarchical epigenetic plasticity," *Blood*, 114(24):4968-4978, 2009.
Clontech. Tet-off advanced inducible gene expression system user manual, pp. 1-27, 2007.
D'Souza et al., "GSK3ß inhibition promotes efficient myeloid and lymphoid hematopoiesis from non-human primate-induced pluripotent stem cells," *Stem Cell Reports*, 6(2):243-256, 2016.
De Paz et al., "Circadian Cycle-Dependent MeCP2 and Brain Chromatin Changes," *PLoS One*, 10(4):e0123693, 2015.
Ditadi et al., "Human definitive haemogenic endothelium and arterial vascular endothelium represent distinct lineages," *Nature Cell Biol.*, 7(5):580-591 and supporting information, 2015.
Doulatov et al., "Hematopoiesis: A Human Perspective," *Cell Stem Cell*, 10:120-36, 2012.
Doulatov et al., "Induction of multipotential hematopoietic progenitors from human pluripotent stem cells via respecification of lineage-restricted precursors," *Cell Stem Cell*, 13(4):459-470, 2013.
Doulatov et al., "Revised map of the human progenitor hierarchy shows the origin of macrophages and dendritic cells in early lymphoid development," *Nature Immunol.*, 11(7):585-593, 2010.
Du Pré et al., "Circadian Rhythms in Cell Maturation," *Physiology*, 29:72-83, 2014.
Ebina et al., "Transcription factor-mediated reprogramming toward hematopoietic stem cells," *EMBO Journal*, 34(6):694-709, 2015.
Eguizabal et al., "Natural killer cells for cancer immunotherapy: pluripotent stem cells-derived NK cells as an immunotherapeutic perspective," *Frontiers in Immunology*, 5, 2014.
Elcheva et al., "Direct induction of haematoendothelial programs in human pluripotent stem cells by transcriptional regulators," *Nat Commun*, 5:4372, 2014.
Encabo et al., "Selective generation of different dendritic cell precursors from CD34+ cells by interleukin-6 and interleukin-3," *Stem Cells*, 22(5):725-740, 2004.
Evans et al., "Cancer of the pancreas," In: Cancer Principles and Practice of Oncology, Devita et al. (Eds.), Lippincot-Raven, NY, 1054-1087, 1997.
Fauser et al., "Stimulatory activity for human pluripotent hemopoietic progenitors produced by a human T-lymphocyte cell line," *Stem Cells*, 1(2):73-80, 1981.
Feng et al., "Scalable generation of universal platelets from human induced pluripotent stem cells," *Stem Cell Reports*, 3(5):817-831, 2014.
Frisan et al., "Generation of Lymphoblastoid Cell Lines (LCLs)," In: Epstein-Barr Virus Protocols, Part III, Wilson et al., (Eds.) Humana Press, 174:125-127, 2001.
Fuks et al., "The Methyl-CpG-binding Protein MeCP2 Links DNA Methylation to Histone Methylation," *J. Biol. Chem.*, 278(6):4035-4040, 2003.
Furie and Furie, "The molecular basis of blood coagulation," *Cell*, 53(4):505-518, 1988.
Gama-Norton et al., "Notch signal strength controls cell fate in the haemogenic endothelium," *Nature Comm.*, 6(8510), 12 pages, 2015.
Gilsbach et al., "Dynamic DNA methylation orchestrates cardiomyocyte development, maturation and disease," *Nature Comm.*, 5(5288):1-13, 2014.
Golde et al., "Production of erythroid-potentiating activity by a human T-lymphoblast cell line," *Proc. Natl. Acad. Sci. USA*, 77(1):593-596, 1980.
Gonzalez et al., "Generation of mouse-induced pluripotent stem cells by transient expression of a single nonviral polycistronic vector," *PNAS*, 106(22):8918-8922, 2009.
Gouon-Evans et al., "BMP-4 is required for hepatic specification of mouse embryonic stem cell-derived definitive endoderm," *Nat. Biotechnol.*, 24(11):1402-1411, 2006.
Haddad et al., "Molecular characterization of early human T/NK and B-lymphoid progenitor cells in umbilical cord blood," *Blood*, 104(13):3918-3926, 2004.
Hermanson et al., "Functional chimeric antigen receptor-expressing natural killer cells derived from human pluripotent stem cells," *Blood*, 122(21):896, 2013.
Hirami et al., "Generation of retinal cells from mouse and human induced pluripotent stem cells," Neurosci. Lett., 458(3): 126-131, 2009.
Huijskens et al., "Technical Advance: Ascorbic acid induces development of double-positive T cells from human hematopoietic stem cells in the absence of stromal cells," *J. Leukocyte Biol.*, 96:1165-1175, 2014.
Jaenisch, "Transgenic animals," *Science*, 240(4858):1468-1474, 1988.
Kennedy et al., "T Lymphocyte Potential Marks the Emergence of Definitive Hematopoietic Progenitors in Human Pluripotent Stem Cell Differentiation Cultures," *Cell Reports*, 2:1722-1735, 2012.
Kieusseian et al., "Immature hematopoietic stem cells undergo maturation in the fetal liver," *Development*, 139(19):3521-3530, 2012.
Kim et al., "Genomic variation and segregation of equine infectious anemia virus during acute infection" *J. Virol.*, 66(6):3879-3882, 1992.
Kitajima et al., "In vitro generation of HSC-like cells from murine ESCs/iPSCs by enforced expression of LIM-homeobox transcription factor Lhx2," *Blood*, 117(14):3748-3758, 2011.
Klimanskaya et al., "Derivation and comparative assessment of retinal pigment epithelium from human embryonic stem cells using transcriptomics." Cloning and Stem Cells 6(3): 217-245 (Nov. 3, 2004).
Knust et al., "EGF homologous sequences encoded in the genome of *Drosophila melanogaster*, and their relation to neurogenic genes," *EMBO J.*, 6(3):761-766, 1987.
Kyba et al., "HoxB4 confers definitive lymphoid-myeloid engraftment potential on embryonic stem cell and yolk sac hematopoietic progenitors," *Cell*, 109(1):29-37, 2002.
Ladi et al., "Thymic microenvironments for T cell differentiation and selection," *Nature Immunology*, 7(4):338-343, 2006.
Lakowski et al., "Effective transplantation of photoreceptor precursor cells selected via cell surface antigen expression," Stem Cells, 29.9: 1391-1404, 2011.
Langle-Rouault et al., "Up to 100-fold increase of apparent gene expression in the presence of Epstein-Barr virus oriP sequences and EBNA1: implications of the nuclear import of plasmids," *J. Virol.*, 72(7):6181-6185, 1998.
Lappalainen et al. "A protocol for generating high numbers of mature and functional human mast cells from peripheral blood," *Clin. Experim. Allergy*, 37:1404-1414, 2007.
Laranjeiro et al., "The Notch Ligand Delta-Like 4 Regulates Multiple Stages of Early Hemato-Vascular Development," *PLoS One*, 7(4):e34553, 1-13, 2012.
Lessard et al., "Comparison of DNA methylation profiles in human fetal and adult red blood cell progenitors," *Genome Med.*, 7(1):1-12, 2015.
Levitskaya et al., "Inhibition of ubiquitin/proteasome-dependent protein degradation by the Gly-Ala repeat domain of the Epstein-Barr virus nuclear antigen 1," *Proc. Natl. Acad. Sci. USA*, 94(23):12616-12621, 1997.

(56) References Cited

OTHER PUBLICATIONS

Li et al., "Engineering human induced pluripotent stem cells with novel chimeric antigen receptors to generate natural killer (NK) cell cancer immunotherapies with targeted anti-tumor activity," Blood, 130(Supplement 1):1905, 2017.
Li et al., "Epigenetic Control of Circadian Clock Operation during Development," *Genetics Res. Int.*, 845429:1-8, 2012.
Ludwig et al. "Derivation of human embryonic stem cells in defined conditions," *Nature Biotech.*, 24(2):185-187, 2006.
Ludwig et al. "Feeder-independent culture of human embryonic stem cells," *Nature Methods*, 3(8):637-646, 2006.
Lusis et al., "Purification and characterization of a human T-lymphocyte-derived granulocyte-macrophage colony-stimulating factor," *Blood*, 57(1):13-21, 1981.
Mandai et al., "Use of lectins to enrich mouse ES-derived retinal progenitor cells for the purpose of transplantation therapy," Cell Transplantation, 19.1:9-19, 2010.
McIntosh et al., "Nonirradiated NOD,B6.SCID Il2rγ-/- Kit(W41/W41) (NBSGW) mice support multilineage engraftment of human hematopoietic cells," *Stem Cell Reports*, 4(2):171-180, 2015.
Minskaia and Ryan, "Protein Coexpression using FMDV 2A: Effect of "Linker" Residues," *BioMed Research International*, Article ID 291790, pp. 1-12, 2013.
Nguyen et al., "Global methylation profiling of lymphoblastoid cell lines reveals epigenetic contributions to autism spectrum disorders and a novel autism candidate gene, RORA, whose protein product is reduced in autistic brain," *FASEB J.*, 24:3037-3051, 2010.
Nicola et al., "Separation of functionally distinct human granulocyte-macrophage colony-stimulating factors," *Blood*, 54(3):614-627, 1979.
Nishimura et al., "Generation of rejuvenated antigen-specific T cells by reprogramming to pluripotency and redifferentiation," *Cell Stem Cell*, 12(1):114-126, 2013.
Nostro et al., "Stage-specific signaling through TGFβ family members and WNT regulates patterning and pancreatic specification of human pluripotent stem cells," *Development*, 138:861-871, 2011.
Notta et al., "Isolation of single human hematopoietic stem cells capable of long-term multilineage engraftment," *Science*, 333(6039):218-221, 2011.
Oberlin et al., "VE-cadherin expression allows identification of a new class of hematopoietic stem cells within human embryonic liver," *Blood*, 116(22):4444-4455, 2010.
Office Action issued in European Application No. 16778383.4, mailed Jun. 25, 2019.
Office Action issued in European Application No. 18724646.7, mailed Jan. 1, 2020.
Okabe, "Large-scale preparation and characterization of human colony-stimulating factor," *J. Cell. Phys.*, 110(1):43-49, 1982.
Pandey et al., "A novel MeCP2 acetylation site regulates interaction with ATRX and HDAC1," *Genes Cancer*, 6(9-10):408-421, 2015.
PCT International Preliminary Report on Patentability issued in International Application No. PCT/US2018/028133, mailed Oct. 31, 2019.
PCT International Search Report and Written Opinion issued in International Application No. PCT/US2016/057899, dated Feb. 17, 2017.
PCT International Search Report and Written Opinion issued in International Application No. PCT/US2017/055353, dated Jan. 22, 2018.
PCT International Search Report and Written Opinion issued in International Application No. PCT/US2016/057893, dated Dec. 6, 2016.
PCT International Search Report and Written Opinion issued in International Application No. PCT/US2017/055369, dated Feb. 16, 2018.
PCT International Search Report and Written Opinion issued in International Application No. PCT/US2016/050554, mailed Nov. 28, 2016.
PCT International Search Report and Written Opinion issued in International Application No. PCT/US2016/050543, mailed Dec. 5, 2016.
PCT International Search Report and Written Opinion issued in International Application No. PCT/US2018/028133, mailed Jun. 26, 2018.
PCT Invitation to Pay Additional Fees issued in International Application No. PCT/US2016/057899, dated Dec. 9, 2016.
Pereira et al., "Induction of a Hemogenic Program in Mouse Fibroblasts," *Cell Stem Cell*, 13(2):205-218, 2013.
Pick et al., "Differentiation of human embryonic stem cells in serum-free medium reveals distinct roles for bone morphogenetic protein 4, vascular endothelial growth factor, stem cell factor, and fibroblast growth factor 2 in hematopoiesis," *Stem Cells*, 25(9):2206-2214, 2007.
Ramos-Mejia et al., "HOXA9 promotes hematopoietic commitment of human embryonic stem cells," *Blood*, 124(20):3065-3075, 2014.
Reubinoff et al., "Embryonic stem cell lines from human blastocysts: somatic differentiation in vitro," *Nat. Biotechnol.*, 18(4):399-404, 2000.
Riddell et al., "Reprogramming committed murine blood cells to induced hematopoietic stem cells with defined factors," *Cell*, 157(3):549-564, 2014.
Rowland et al., "Differentiation of human pluripotent stem cells to retinal pigmented epithelium in defined conditions using purified extracellular matrix proteins." Journal of Tissue Engineering and Regenerative Medicine 7: 642-653 (published online Apr. 18, 2012).
Sackett et al., "Modulation of human allogeneic and syngeneic pluripotent stem cells and immunological implications for transplantation," *Transplantation Reviews*, 30(2):61-70, 2016.
Salvagiotto et al., "A Defined, Feeder-Free, Serum-Free System to Generate In Vitro Hematopoietic Progenitors and Differentiated Blood Cells from hESCs and hiPSCs," *PLoS One*, 6(3):e17829, 2011.
Sandler et al., "Reprogramming human endothelial cells to haematopoietic cells requires vascular induction," *Nature*, 511(7509):312-318, 2014.
SBI. pCDH cDNA cloning and expression lentivectors user manual, pp. 1-20, 2013.
Schernthaner et al., "Expression, epitope analysis, and functional role of the LFA-2 antigen detectable on neoplastic mast cells," *Blood*, 98:3784-3792, 2001.
Scicchitano et al., "In vitro expansion of human cord blood CD36+ erythroid progenitors: Temporal changes in gene and protein expression," *Exp Hematol.*, 31(9):760-769, 2003.
Sharghi-Namini et al., "Dll4-containing exosomes induce capillary sprout retraction in a 3D microenvironment," *Scientific Reports*, 4(4031):1-8, 2014.
Slukvin et al. "Direct differentiation of human embryonic stem cells into functional dendritic cells through the Myeloid Pathway," *The Journal of Immunology*, 176:2924-2932, 2006.
Sthanam et al., "Biophysical regulation of mouse embryonic stem cell fate and genomic integrity by feeder derived matrices," *Biomaterials*, 119:9-22, 2016.
Sturgeon et al., "Wnt signaling controls the specification of definitive and primitive hematopoiesis from human pluripotent stem cells," *Nat. Biotechnol.*, 32:554-561, 2014.
Sundberg et al., "CD marker expression profiles of human embryonic stem cells and their neural derivatives, determined using flow-cytometric analysis, reveal a novel CD marker for exclusion of pluripotent stem cells," *Stem Cell Research*, 2:113-124, 2009.
Suzuki et al., "Generation of Engraftable Hematopoietic Stem Cells from Induced Pluripotent Stem Cells by Way of Teratoma Formation," *Mol Ther.*, 21(7):1424-1431, 2013.
Suzuki et al., "Structure and expression of human thrombomodulin, a thrombin receptor on endothelium acting as a cofactor for protein C activation," *EMBO J.*, 6(7):1891-1897, 1987.
Takahashi et al., "Induction of Pluripotent Stem Cells from Mouse Embryonic and Adult Fibroblast Cultures by Defined Factors," *Cell*, 131(5):861-872, 2007.
Takeda et al., "NUP98-HOXA9 induces long-term proliferation and blocks differentiation of primary human CD34+ hematopoietic cells," *Cancer Res.*, 66:6628-6637, 2006.

(56) References Cited

OTHER PUBLICATIONS

Tanaka et al., "Transcriptional regulation in pluripotent stem cells by methyl CpG-binding protein 2 (MeCPG2)," *Human Mol. Genetics*, 23(4):1045-1055, 2013.
Theisen et al., "Biochemical Analysis of Histone Deacetylase-independent Transcriptional Repression by MeCP2," *J. Biol. Chem.*, 288(10):7096-7104, 2013.
Themeli et al., "Generation of tumor-targeted human T lymphocytes from induced pluripotent stem cells for cancer therapy," *Nature Biotechnology*, 31(10):928-933, and supplementary information, 2013.
Themeli et al., "New cell sources for T cell engineering and adoptive immunotherapy," *Cell Stem Cell*, 16(4):357-366, 2015.
Thomson et al., "Human embryonic stem cell and embryonic germ cell lines," Trends in Biotechnology 18.2 (2000): 53-57.
U.S. Appl. No. 61/088,054 entitled "Methods for the Production of IPS Cells" by Amanda Mack et al., filed Aug. 12, 2008.
U.S. Appl. No. 61/759,988, entitled "Method for generating retinal pigment epithlium (RPE) cells from induced pluripotent stem cells (IPSCs)," filed Feb. 1, 2013.
Vacca et al., "CD34+ hematopoietic precursors are present in human decidua and differentiate into natural killer cells upon interaction with stromal cells," *PNAS*, 108(6):2402-2407, 2011.
Van der Jeught et al., "The combination of inhibitors of FGF/MEK/Erk and GSK3β signaling increases the number of OCT3/4-and NANOG-positive cells in the human inner cell mass, but does not improve stem cell derivation" Stem Cells and Development 22(2): 296-306 (published online Jul. 11, 2012).
Vecsler et al., "MeCP2 deficiency down-regulates specific nuclear proteins that could be partially recovered by valproic acid in vitro," *Epigenetics*, 5(1):61-67, 2010.
Vo et al., "De novo generation of HSCs from somatic and pluripotent stem cell sources," *Blood*, 125(17):2641-2648, 2015.
Vugler et al., "Elucidating the phenomenon of HESC-derived RPE: anatomy of cell genesis, expansion and retinal transplantation." Experimental Neurology 214: 347-361 (published online Sep. 27, 2008).
Wilson et al., "Epigenetic control of T-helper-cell differentiation," *Nature Reviews Immunology*, 9:91-105, 2009.
Wynn, "T(H)-17: a giant step from T(H)1 and T(H)2," *Nature Immunology*, 6:1069-1070, 2005.
Xi et al. "In Vitro Large Scale Production of Human Mature Red Blood Cells from Hematopoietic Stem Cells by Coculturing with Human Fetal Liver Stromal Cells," *Biomed Res. Int.*, 2013(807863):1-12, 2013.
Yamanaka et al., "Induction of pluripotent stem cells from adult human fibroblasts by defined factors," *Cell*, 131(5):861-72, 2007.
Ying et al., "Conversion of embryonic stem cells into neuroectodermal precursors in adherent monoculture," 21(2):183-6, 2003.
Young et al., "Human Pluripotent and Progenitor Cells Display Cell Surface Cluster Differentiation Markers CD10, CD13, CD56 and MHC Class-I", Proceedings of the Society of Experimental Biology and Medicine, 1999, vol. 221, No. 1, pp. 63-71. (Year: 1999).
Yu et al. "Induced Pluripotent Stem Cell Lines Derived from Human Somatic Cells," *Science*, 318(5858):1917-1920, 2007.
Zhang et al., "DNA methylation dynamics during ex vivo differentiation and maturation of human dendritic cells," *Epigenetics Chromatin*, 7(21):1-16, 2014.
Office Action issued in Chinese Application No. 201880031627.X, mailed Feb. 24, 2023, and English translation thereof.

\* cited by examiner

ANTIGEN-SPECIFIC IMMUNE EFFECTOR CELLS

The present application is a national phase application under 35 U.S.C. § 371 of International Application No. PCT/US2018/028133, filed Apr. 18, 2018, which claims the priority benefit of U.S. Provisional Application Ser. No. 62/486,875, filed Apr. 18, 2017, the entire contents of each of which are hereby incorporated by reference.

BACKGROUND

1. Field

The present invention relates generally to the field of molecular biology. More particularly, it concerns methods and compositions concerning antigen-specific immune effector cells, such as T cells and NK cells.

2. Description of Related Art

Despite technological advancements in the diagnosis and treatment options available to patients diagnosed with cancer, the prognosis still often remains poor and many patients cannot be cured. Immunotherapy holds the promise of offering a potent, yet targeted, treatment to patients diagnosed with various tumors with the potential to eradicate the malignant tumor cells without damaging normal tissues. In theory, the T cells of the immune system are capable of recognizing protein patterns specific for tumor cells and to mediate their destruction through a variety of effector mechanisms. Adoptive T cell therapy is an attempt to harness and amplify the tumor-eradicating capacity of a patient's own T cells and then return these effectors to the patient in such a state that they effectively eliminate residual tumor, however without damaging healthy tissue. Although this approach is not new to the field of tumor immunology, many drawbacks in the clinical use of adoptive T cell therapy impair the full use of this approach in cancer treatments.

Current adoptive T cell therapies are limited by a lack of patient and tumor-specific T cells, including their rarity in the body, their failure to overcome a number of tumor immune system evading mechanisms, and their short life span. It is difficult to isolate and expand the typically low numbers of T cells reactive to a desired antigen. Therefore, there is an unmet need for therapeutically sufficient and functional antigen-specific immune cells for effective use in immunotherapy.

SUMMARY

In a first embodiment, the present disclosure provides a method of producing antigen-specific effector T cells and/or NK cells comprising engineering pluripotent stem cells (PSCs) to express a chimeric antigen receptor (CAR), thereby producing CAR-PSCs; differentiating or forward reprogramming the CAR-PSCs to $CD34^+$ hematopoietic progenitor cells (HPCs); further differentiating the $CD34^+$ HPCs to T cells and/or NK cells; and expanding the T cells and/or NK cells. In some aspects, expanding comprises co-culturing with antigen-specific target cells, thereby producing antigen-specific effector T cells and/or NK cells.

In certain aspects, the PSCs engineered to express a CAR are induced pluripotent stem cells (iPSCs) or embryonic stem cells (ESCs). In particular aspects, the iPSCs are reprogrammed from somatic cells, such as T cells.

In some aspects, the step of differentiating CAR-PSCs to $CD34^+$ HPCs comprises performing directed differentiation. In certain aspects, directed differentiation comprises generating embryoid bodies (EBs) in the presence of blebbistatin, a GSK-3 inhibitor, FGF2, and VEGF; contacting the EBs with BMP4, VEGF, and FGF2 to induce mesoderm induction; and differentiating the EBs in the presence of Flt-3 ligand, IL-3, SCF, and TPO, thereby producing HPCs. In some aspects, the differentiating is in media essentially free of or free of BMP4. In other aspects, the differentiating is in the presence of BMP4. In particular aspects, the GSK-3 inhibitor is CHIR99021. In some aspects, differentiating further comprises the presence of IL-11, cAMP, and/or VEGF.

In some aspects, directed differentiation comprises culturing individualized PSCs on an amine-coated surface in the presence of blebbistatin, BMP4, VEGF, and bFGF; initiating differentiation by contacting the PSCs with BMP4, VEGF, and FGF2; and further differentiating the PSCs in the presence of Flt-3 ligand, IL-3, IL-6, SCF, TPO, and heparin, thereby producing HPCs, wherein the method does not comprise the formation of EBs.

In particular aspects, the method comprises culturing the cells under defined, feeder-free conditions, such as for the duration of the whole method. In some aspects, the PSCs are essentially transgene-free or are transgene-free. In particular aspects, the PSCs are human. In certain aspects, the T cells are $CD4^+$ T cells, $CD8^+$ T cells, cytotoxic T cells, regulatory T cells, natural killer T cells, naïve T cells, memory T cells, and/or gamma delta T cells.

In certain aspects, the PSCs engineered to express a CAR are further engineered to express ERG/ETV2, GATA2, and HOXA9, such as under the control of a single inducible promoter. In some aspects, the method further comprises engineering the PSCs to express HMGA2, MYCN, NR4A2, SOX17, TFEC, MEIS1, and/or HOXA4. Thus, in some aspects, the step of differentiating CAR-PSCs to $CD34^+$ HPCs comprises inducing expression of ERG/ETV2, GATA2, and HOXA9 for a period of time sufficient to produce HPCs and terminating the induction of expression prior to further differentiating the HPCs to T cells and/or NK cells.

In specific aspects, the step of differentiating CAR-PSCs to $CD34^+$ HPCs further comprises selecting for cells that express CD34 and/or CD43 prior to differentiating to antigen-specific T cells and/or NK cells. In particular aspects, selecting comprises performing magnetic-activated cell sorting (MACS). In some aspects, the cells that express CD34 and/or CD43 comprise at least 25, 30, 35, 40, 45, 50, 60, 65, 70, 75, 80, 85, 90, or higher percent of the total cell population. In some aspects, the step of performing MACs to select for CD34 and/or CD43 positive cells is not performed.

In particular aspects, at least 2, 3, 4, 5, 10, 15, 20, or higher percent of the HPCs express the CAR. In some aspects, at least 3, 4, 5, 6, 7, 8, 9, 10, 11, 12, 13, 14, 15, 20, 25, 30, 35, 40, 45 or higher percent of the HPCs express the CAR.

In some aspects, differentiating of HPCs to T cells and/or NK cells comprises culturing the HPCs on a retronectin and Notch DLL-4 coated surface in the presence of ascorbic acid and nicotinamide under hypoxic conditions. In some aspects, the culture further comprises SCF, FLT-3 ligand, TPO, and IL-7, and optionally comprises a GSK inhibitor (e.g., CHIR99021), IL-2, and/or IL-12. In certain aspects, the expanding step further comprises culturing the antigen-specific T cells in the presence of anti-CD3 antibody and IL-2. In further aspects, the expanding step further comprises culturing the antigen-specific T cells in the presence of anti-CD3 antibody, IL-2, IL-15, and IL-21. In some aspects, the expanding step comprises culturing the antigen-specific T cells in the presence of anti-CD3 antibody, FLT3-ligand, IL-7, IL-2, and/or IL-15, and optionally further comprises SCF, TPO, and/or IL-21. In particular aspects, at least 1, 1.5, 2, 2.5, 3, 4, 5, 6, 7, 8, 9, 10, 15, 20, 25, 30, 35, 40, 45, 50 or higher percent of the differentiated $CD34^+$ HPCs are $CD3+CAR^+$ T cells. In some aspects, at least 1, 2, 3, 4, 5, 6, 7, 8, 9, 10, 15, 20, 25, 30, 35, 40, 50, or higher percent of the differentiated $CD34^+$ HPCs are $CD3-CAR^+$ NK cells. In some aspects, at least 2 percent of the expanded CD34+ HPCs are $CD3+CAR^+$ T cells. In particular aspects, at least 10 percent of the expanded CD34+ HPCs are $CD3-CAR^+$ NK cells.

In certain aspects, the CAR and the antigen-specific target cells are directed to the same antigen. In one specific aspects, the antigen is CD19. In particular aspects, the antigen-specific target cells are tumor cells. In some aspects, the antigen-specific target cells are human. In particular aspects, the antigen-specific target cells are HLA class I negative. In some aspects, at least 5, such as 6, 7, 8, 9, 10, 15, 20, 25, 30, 35, 40, 50, or higher, percent of the antigen-specific effector T cells display cytotoxic activity against target cells. In certain aspects, at least 10, such as 15, 20, 25, 30, 35, 40, 45, 50, or higher, percent of the antigen-specific effector NK cells display cytotoxic activity against target cells.

In some aspects, the CAR is encoded by DNA integrated into the genome of the PSCs. In certain aspects, the CAR comprises an intracellular signaling domain, a transmembrane domain, and an extracellular domain comprising an antigen binding region. In specific aspects, the intracellular signaling domains comprise CD3ζ and CD28. In some aspects, the antigen binding region is a F(ab')2, Fab', Fab, Fv, or scFv.

In certain aspects, the PSCs are HLA homozygous. In some aspects, the HLA homozygous PSCs are homozygous for one or more of the loci alleles HLA-A, HLA-B, HLA-C, HLA-DR, HLA-DP or HLA-DQ. In certain aspects, the HLA homozygous PSCs are homozygous for two of the loci alleles HLA-A, HLA-B, HLA-C, HLA-DR, HLA-DP or HLA-DQ. In particular aspects, the HLA homozygous PSCs are homozygous for HLA-A and HLA-B. In certain aspects, the HLA homozygous PSCs are homozygous for HLA-A, HLA-B, and HLA-C.

Another embodiment provides a method of producing antigen-specific effector T cells and/or NK cells comprising engineering PSCs to express a CAR, thereby producing CAR-PSCs; culturing the CAR-PSCs in the presence of blebbistatin, a GSK-3 inhibitor, FGF2, and VEGF, thereby generating EBs; contacting the EBs with BMP4, VEGF, and FGF2 to induce mesoderm induction; differentiating the EBs in the presence of Flt-3 ligand, BMP4, IL-3, SCF, and TPO, thereby producing $CD34^+$ HPCs; further differentiating the $CD34^+$ HPCs to T cells and/or NK cells; and expanding the T cells and/or NK cells, wherein expanding comprises co-culturing with antigen-specific target cells, thereby producing antigen-specific effector T cells and/or NK cells. In particular aspects, the GSK-3 inhibitor is CHIR99021.

In yet another embodiment, there is provided a method of producing antigen-specific effector T cells and/or NK cells comprising engineering PSCs to express a CAR, thereby producing CAR-PSCs; culturing individualized CAR-PSCs on an amine-coated surface in the presence of blebbistatin, BMP4, VEGF, and initiating differentiation by contacting the CAR-PSCs with BMP4, VEGF, and FGF2; further differentiating the CAR-PSCs in the presence of Flt-3 ligand, IL-3, IL-6, SCF, TPO, and heparin, thereby producing $CD34^+$ HPCs; differentiating the $CD34^+$ HPCs to T cells and/or NK cells; and expanding the T cells and/or NK cells, wherein expanding comprises co-culturing with antigen-specific target cells, thereby producing antigen-specific effector T cells and/or NK cells, wherein the method does not comprise the formation of EBs.

A further embodiment provides a method of producing antigen-specific effector T cells and/or NK cells comprising engineering PSCs to express a CAR, thereby producing CAR-PSCs; differentiating the CAR-PSCs to $CD34^+$ HPCs; selecting for $CD34+CD43^+$ HPCs; further differentiating the $CD34+CD43^+$ HPCs to T cells and/or NK cells; and expanding the T cells and/or NK cells, wherein expanding comprises co-culturing with antigen-specific target cells, thereby producing antigen-specific effector T cells and/or NK cells.

In another embodiment, there is provided a population of antigen-specific effector T cells and/or NK cells produced according to the embodiments described above. Also provided herein is a pharmaceutical composition comprising the antigen-specific effector T cells and/or NK cells produced according to the embodiments described herein. Further provided herein is a composition comprising the antigen-specific effector T cells and/or NK cells produced according to the embodiments for the treatment of cancer in a subject. Also provided herein is the use of the antigen-specific effector T cells and/or NK cells produced according to the embodiments for the treatment of cancer.

In yet another embodiment, there is provided a method of treating cancer in a subject comprising administering an effective amount of the antigen-specific effector T cells and/or NK cells produced according to the embodiments described herein to the subject. In some aspects, the cancer expresses a tumor antigen and the antigen-specific effector T cells and/or NK cells are directed to said tumor antigen. In particular aspects, the subject is human.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A) Schematic depicting methods for producing T cells and NK cells from PSCs, including forward programming methods and directed differentiation methods. (FIG. 1B) Diagram representing feeder-free and serum-free T and NK cell differentiation of hPCS. Abbreviations: CHIR-CHIR99021 GSK-3 inhibitor; HDM, serum-free hematopoietic differentiation medium; TCDM, T cell differentiation medium; TCEM, T cell expansion medium; HPC, hematopoietic progenitor cells; asterisk (*) marked are optional enhancing components. (FIG. 1C) Efficiency of $CD34^+CD43^+$ HPCs from PSCs through directed differentiation or forward programming. (FIG. 1D) Flow cytometric analysis of T/NK differentiation cultures. (FIG. 1E) Yield of different cell populations throughout differentiation. (FIG. 1F) Phenotype of PSC-derived T cells. (FIG. 1G) Expansion of PSC-derived T cells. Immobilized anti-CD3 antibodies (iCD3) are for expansion of PSC-derived T cells (bar graph). T cells proliferating in the expansion cultures acquire a characteristic morphology of irregularly shaped lymphoblasts (photograph). CD56 and acquire CD8 expression of 2 week T cell expansion (flow cytometry dot plots).

(FIG. 3A) In vitro cytotoxicity assay using luciferase-expressing $CD19^+$ Daudi and Raji target cells. (FIG. 3B) Cytolytic potential of CAR-T cells by real-time target cell counting using Incucyte S3 live-cell analysis system (Essen Bioscience).

(FIG. 5A) Tumor progression in mice monitored by in vivo bioluminescent imaging. (FIG. 5B) Survival curves in different groups of mice treated either with PSC-derived T (1C) or NK (A16) cells.

DESCRIPTION OF ILLUSTRATIVE EMBODIMENTS

Figure 1A:
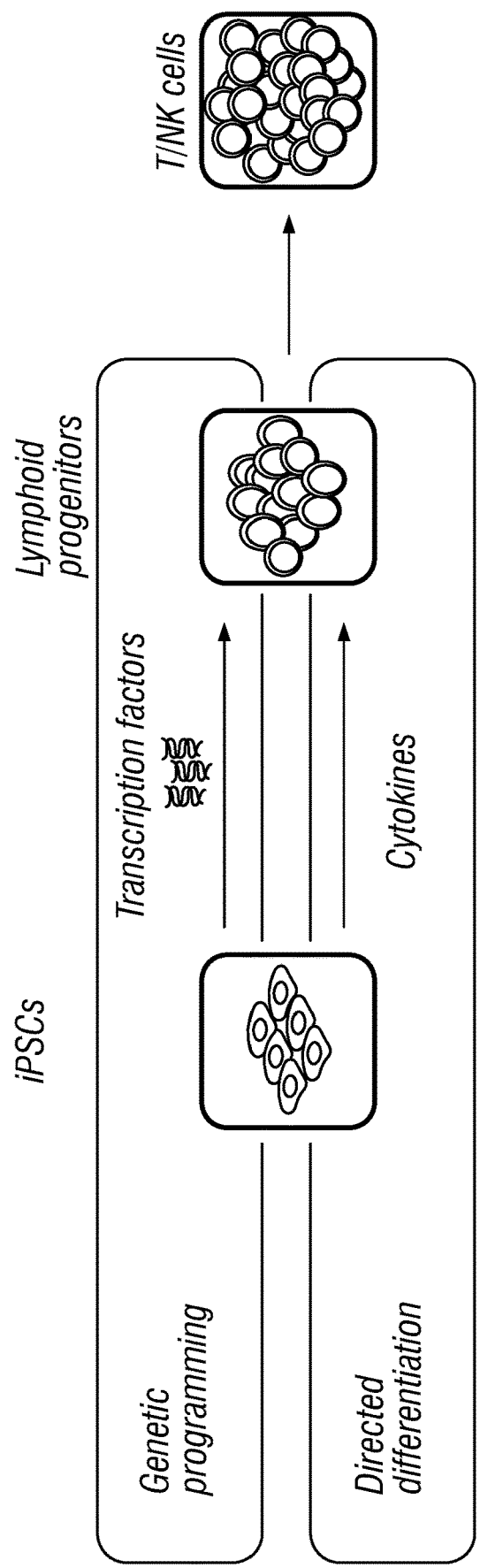
FIGS. 1A-1G.

In certain embodiments, the present disclosure provides highly efficient methods for generating antigen-specific immune effector cells from human pluripotent stem cells (PSCs) which have been engineered to express an antigen receptor, such as a chimeric antigen receptor (CAR), referred to herein as CAR-PSCs. The immune effector cells produced by the current methods can include, but are not limited to, T cells, NK cells, and iNKT cells.

The PSCs may be obtained by reprogramming (e.g., by retroviral or episomal methods) a starting population of T cells to produce T cell-derived iPSCs (TiPSCs). The T cells may be isolated from various sources, such as a blood sample. The starting population of T cells may retain their characteristic T cell receptor (TCR) gene rearrangements and may be HLA homozygous cells (i.e., homozygous for MHC Class I and II genes). Accordingly, iPSCs can be produced from cells isolated from HLA homozygous subjects, referred to herein as HLA super donors.

The CAR-PSCs may then be differentiated or programmed to produce $CD34^+$ hematopoietic progenitor cells (HPCs). This may be achieved through directed differentiation using a combination of cytokines (e.g., SCF, TPO, FLT-3, IL-6, IL-3, and heparin) (e.g., described in PCT/US2016/057899, incorporated herein by reference in its entirety). In an alternate method, the CAR-PSCs may be differentiated to $CD34^+$ HPCs using forward programming with an expression construct encoding ETV2/ERG, GATA2, and HOXA9 (i.e., EGH) (e.g., described in PCT/US2016/057893, incorporated herein by reference in its entirety). These EGH-PSCs may be further engineered to express HMGA2, MYCN, NR4A2, SOX17, TFEC, MEIS1, and/or HOXA4 for long-term engraftability.

Finally, the $CD34^+$ CAR-HPCs may be differentiated to $CD3^+$ T cells or $CD56^+CD3^-$ NK cells. An optimal timeframe during HPC differentiation (e.g., day 7-11) for lymphoid potential may be days 7-11, identified by expression of CD34 and CD43. For example, HPCs with enhanced lymphoid potential may be isolated by sorting for fractions of cells positive for two or more of the markers CD144, CD34, CD45, and CD7.

An exemplary method for T cell differentiation comprises the use of RetroNectin and DLL-4 as a feeder free matrix. The T cell differentiation may be further enhanced by the use of ascorbic acid to increase the efficiency and maturation as well as by culturing under hypoxic conditions.

Further, the T cells and/or NK cells may be expanded by co-culturing with antigen-specific target cells (e.g., tumor cells) during the differentiation process. This method was found to increase the cytotoxic activity of the T cells and NK cells against target cells, specifically observed by a decrease in tumor growth and increase in survival of mice injected with tumor cells.

Thus, the methods of the present disclosure could provide unlimited numbers of antigen-specific immune effector cells, such as T cells and NK cells, for a wide range of applications such as stable transplantation in vivo, screening of compounds in vitro, and elucidating the mechanisms of hematological diseases and injuries.

I. DEFINITIONS

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

The term "exogenous," when used in relation to a protein, gene, nucleic acid, or polynucleotide in a cell or organism refers to a protein, gene, nucleic acid, or polynucleotide that has been introduced into the cell or organism by artificial or natural means; or in relation to a cell, the term refers to a cell that was isolated and subsequently introduced to other cells or to an organism by artificial or natural means. An exogenous nucleic acid may be from a different organism or cell, or it may be one or more additional copies of a nucleic acid that occurs naturally within the organism or cell. An exogenous cell may be from a different organism, or it may be from the same organism. By way of a non-limiting example, an exogenous nucleic acid is one that is in a chromosomal location different from where it would be in natural cells, or is otherwise flanked by a different nucleic acid sequence than that found in nature.

By "expression construct" or "expression cassette" is meant a nucleic acid molecule that is capable of directing transcription. An expression construct includes, at a minimum, one or more transcriptional control elements (such as promoters, enhancers or a structure functionally equivalent thereof) that direct gene expression in one or more desired cell types, tissues or organs. Additional elements, such as a transcription termination signal, may also be included.

A "vector" or "construct" (sometimes referred to as a gene delivery system or gene transfer "vehicle") refers to a macromolecule or complex of molecules comprising a polynucleotide to be delivered to a host cell, either in vitro or in vivo.

A "plasmid," a common type of a vector, is an extra-chromosomal DNA molecule separate from the chromosomal DNA that is capable of replicating independently of the chromosomal DNA. In certain cases, it is circular and double-stranded.

An "origin of replication" ("ori") or "replication origin" is a DNA sequence, e.g., in a lymphotrophic herpes virus, that when present in a plasmid in a cell is capable of maintaining linked sequences in the plasmid and/or a site at or near where DNA synthesis initiates. As an example, an ori for EBV (Ebstein-Barr virus) includes FR sequences (20 imperfect copies of a 30 bp repeat), and preferably DS sequences; however, other sites in EBV bind EBNA-1, e.g., Rep* sequences can substitute for DS as an origin of replication (Kirshmaier and Sugden, 1998). Thus, a replication origin of EBV includes FR, DS or Rep* sequences or any functionally equivalent sequences through nucleic acid modifications or synthetic combination derived therefrom. For example, the present disclosure may also use genetically engineered replication origin of EBV, such as by insertion or mutation of individual elements, as specifically described in Lindner et al., 2008.

A "gene," "polynucleotide," "coding region," "sequence," "segment," "fragment," or "transgene" that "encodes" a particular protein, is a nucleic acid molecule that is transcribed and optionally also translated into a gene product, e.g., a polypeptide, in vitro or in vivo when placed under the control of appropriate regulatory sequences. The coding region may be present in either a cDNA, genomic DNA, or RNA form. When present in a DNA form, the nucleic acid molecule may be single-stranded (i.e., the sense strand) or double-stranded. The boundaries of a coding region are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and synthetic DNA sequences. A transcription termination sequence will usually be located 3' to the gene sequence.

The term "control elements" refers collectively to promoter regions, polyadenylation signals, transcription termination sequences, upstream regulatory domains, origins of replication, internal ribosome entry sites (IRES), enhancers, splice junctions, and the like, which collectively provide for the replication, transcription, post-transcriptional processing, and translation of a coding sequence in a recipient cell. Not all of these control elements need be present so long as the selected coding sequence is capable of being replicated, transcribed, and translated in an appropriate host cell.

The term "promoter" is used herein in its ordinary sense to refer to a nucleotide region comprising a DNA regulatory sequence, wherein the regulatory sequence is derived from a gene that is capable of binding RNA polymerase and initiating transcription of a downstream (3' direction) coding sequence. It may contain genetic elements at which regulatory proteins and molecules may bind, such as RNA polymerase and other transcription factors, to initiate the specific transcription of a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

By "enhancer" is meant a nucleic acid sequence that, when positioned proximate to a promoter, confers increased transcription activity relative to the transcription activity resulting from the promoter in the absence of the enhancer domain.

By "operably linked" or co-expressed" with reference to nucleic acid molecules is meant that two or more nucleic acid molecules (e.g., a nucleic acid molecule to be transcribed, a promoter, and an enhancer element) are connected in such a way as to permit transcription of the nucleic acid molecule. "Operably linked" or "co-expressed" with reference to peptide and/or polypeptide molecules means that two or more peptide and/or polypeptide molecules are connected in such a way as to yield a single polypeptide chain, i.e., a fusion polypeptide, having at least one property of each peptide and/or polypeptide component of the fusion. The fusion polypeptide is preferably chimeric, i.e., composed of heterologous molecules.

"Homology" refers to the percent of identity between two polynucleotides or two polypeptides. The correspondence between one sequence and another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions that promote the formation of stable duplexes between homologous regions, followed by digestion with single strand-specific nuclease(s), and size determination of the digested fragments. Two DNA, or two polypeptide, sequences are "substantially homologous" to each other when at least about 80%, preferably at least about 90%, and most preferably at least about 95% of the nucleotides, or amino acids, respectively match over a defined length of the molecules, as determined using the methods above.

The term "cell" is herein used in its broadest sense in the art and refers to a living body that is a structural unit of tissue of a multicellular organism, is surrounded by a membrane structure that isolates it from the outside, has the capability of self-replicating, and has genetic information and a mechanism for expressing it. Cells used herein may be naturally-occurring cells or artificially modified cells (e.g., fusion cells, genetically modified cells, etc.).

The term "stem cell" refers herein to a cell that under suitable conditions is capable of differentiating into a diverse range of specialized cell types, while under other suitable conditions is capable of self-renewing and remaining in an essentially undifferentiated pluripotent state. The term "stem cell" also encompasses a pluripotent cell, multipotent cell, precursor cell and progenitor cell. Exemplary human stem cells can be obtained from hematopoietic or mesenchymal stem cells obtained from bone marrow tissue, embryonic stem cells obtained from embryonic tissue, or embryonic germ cells obtained from genital tissue of a fetus. Exemplary pluripotent stem cells can also be produced from somatic cells by reprogramming them to a pluripotent state by the expression of certain transcription factors associated with pluripotency; these cells are called "induced pluripotent stem cells" or "iPSCs or iPS cells".

An "embryonic stem (ES) cell" is an undifferentiated pluripotent cell which is obtained from an embryo in an early stage, such as the inner cell mass at the blastocyst stage, or produced by artificial means (e.g. nuclear transfer) and can give rise to any differentiated cell type in an embryo or an adult, including germ cells (e.g. sperm and eggs).

"Induced pluripotent stem cells (iPSCs or iPS cells)" are cells generated by reprogramming a somatic cell by expressing or inducing expression of a combination of factors (herein referred to as reprogramming factors). iPS cells can be generated using fetal, postnatal, newborn, juvenile, or adult somatic cells. In certain embodiments, factors that can be used to reprogram somatic cells to pluripotent stem cells include, for example, Oct4 (sometimes referred to as Oct 3/4), Sox2, c-Myc, Klf4, Nanog, and Lin28. In some embodiments, somatic cells are reprogrammed by expressing at least two reprogramming factors, at least three reprogramming factors, at least four reprogramming factors, at least five reprogramming factors, at least six reprogramming factors, or at least seven reprogramming factors to reprogram a somatic cell to a pluripotent stem cell.

"Hematopoietic progenitor cells" or "hematopoietic precursor cells" refers to cells which are committed to a hematopoietic lineage but are capable of further hematopoietic differentiation and include hematopoietic stem cells, multipotential hematopoietic stem cells, common myeloid progenitors, megakaryocyte progenitors, erythrocyte progenitors, and lymphoid progenitors. Hematopoietic stem cells (HSCs) are multipotent stem cells that give rise to all the blood cell types including myeloid (monocytes and macrophages, granulocytes (neutrophils, basophils, eosinophils, and mast cells), erythrocytes, megakaryocytes/platelets, dendritic cells), and lymphoid lineages (T-cells, B-cells, NK-cells) (see e.g., Doulatov et al., 2012; Notta et al., 2015). A "multilymphoid progenitor" (MLP) is defined to describe any progenitor that gives rise to all lymphoid lineages (B, T, and NK cells), but that may or may not have other (myeloid) potentials (Doulatov et al., 2010) and is CD45RA$^+$/CD10$^+$/CD7$^-$. Any B, T, and NK progenitor can be referred to as an MLP. A "common myeloid progenitor" (CMP) refers to a common myeloid progenitor is defined by the expression of CD45+/CD31$^+$/CD43$^+$/CD34$^-$ cells that can give rise to granulocytes, monocytes, megakaryocytes and erythrocytes. The hematopoietic progenitor cells may express CD34. The hematopoietic progenitor cells may co-express CD133 and be negative for CD38 expression. Hematopoietic precursor cells include CD34$^+$/CD45$^+$ hematopoietic precursor cells and CD34$^+$/CD45$^+$/CD43$^+$ hematopoietic precursor cells. The CD34$^+$/CD43$^+$/CD45$^+$ hematopoietic precursor cells may be highly enriched for myeloid progenitors. Hematopoietic cells also include various subsets of primitive hematopoietic cells including: CD34$^+$/CD133$^+$/CD38$^-$ (primitive hematopoietic precursor cells), CD43(+)CD235a (+)CD41a(+/−) (erythro-megakaryopoietic), lin(−)CD34(+) CD43(+)CD45(−) (multipotent), and lin(−)CD34(+)CD43 (+)CD45(+) (myeloid-skewed) cells, CD133+/ALDH+ (aldehydehydrogenase). It is anticipated that any of these primitive hematopoietic cell types or hematopoietic precursor cells may be converted into iPS cells as described herein. In some aspects, the cells may include Mast cells, Langerhan's cells, Osteoclasts, NK cells, T cells, CIK T cells, or other subtypes of T cells, NK cells, and B cells.

As used herein, the term "immune cell(s)" refers to cells of the immune system, including, but not limited to, T cells, NK cells, T/NK cells, dendritic cells, macrophages, B cells, neutrophils, erythrocytes, monocytes, basophils, neutrophils, mast cells, eosinphils, and any combination thereof.

An "activator" of a T cell or a condition that will activate a T cell refers to a stimulus that activates T cells and include antigens, which may be presented on antigen presenting cells or on other surfaces; polyclonal activators, which bind to many T cell receptor (TCR) complexes regardless of specificity, and include lectins, e.g., concanavalin-A (Con-A) and phytohemagglutinin (PHA) and agents such as antibodies that bind specifically to invariant framework epitopes on TCR or CD3 proteins; and superantigens, which stimulate a significant number of T cells, and include, e.g., enterotoxins, such as Staphyloccal enterotoxins.

The terms "T lymphocyte" and "T cell" are used interchangeably, and refer to a cell that expresses a TCR capable of recognizing antigen when displayed on the surface of antigen presenting cells or matrix together with one or more MHC molecules or, one or more non-classical MHC molecules.

The term "T cell" refers to T lymphocytes as defined in the art and is intended to include thymocytes, immature T lymphocytes, mature T lymphocytes, resting T lymphocytes, or activated T lymphocytes. The T cells can be CD4$^+$ T cells, CD8$^+$ T cells, CD4$^+$CD8$^+$ T cells, or CD4-CD8-cells. The T cells can also be T helper cells, such as T helper 1 (TH1), or T helper 2 (TH2) cells, or TH17 cells, as well as cytotoxic T cells, regulatory T cells, natural killer T cells, naïve T cells, memory T cells, or gamma delta T cells (Wilson et al., 2009; Wynn, 2005; Ladi et al., 2006). T cells that differ from each other by at least one marker, such as CD4, are referred to herein as "subsets" of T cells.

"CD4$^+$ T cells" refers to a subset of T cells that express CD4 on their surface and are associated with cell-mediated immune response. They are characterized by the secretion profiles following stimulation, which may include secretion of cytokines such as IFN-gamma, TNF-alpha, IL-2, IL-4 and IL-10. "CD4" are 55-kD glycoproteins originally defined as differentiation antigens on T-lymphocytes, but also found on other cells including monocytes/macrophages. CD4 antigens are members of the immunoglobulin supergene family and are implicated as associative recognition elements in MHC (major histocompatibility complex) class II-restricted immune responses. On T-lymphocytes they define the helper/inducer subset.

"CD8$^+$ T cells" refers to a subset of T cells which express CD8 on their surface, are MHC class I-restricted, and function as cytotoxic T cells. "CD8" molecules are differentiation antigens found on thymocytes and on cytotoxic and suppressor T-lymphocytes. CD8 antigens are members of the immunoglobulin supergene family and are associative recognition elements in major histocompatibility complex class I-restricted interactions.

"Pluripotent stem cell" refers to a stem cell that has the potential to differentiate into all cells constituting one or more tissues or organs, or preferably, any of the three germ layers: endoderm (interior stomach lining, gastrointestinal tract, the lungs), mesoderm (muscle, bone, blood, urogenital), or ectoderm (epidermal tissues and nervous system).

As used herein, the term "somatic cell" refers to any cell other than germ cells, such as an egg, a sperm, or the like, which does not directly transfer its DNA to the next generation. Typically, somatic cells have limited or no pluripotency. Somatic cells used herein may be naturally-occurring or genetically modified.

"Programming" is a process that alters the type of progeny a cell can produce. For example, a cell has been programmed when it has been altered so that it can form progeny of at least one new cell type, either in culture or in vivo, as compared to what it would have been able to form under the same conditions without programming. This means that after sufficient proliferation, a measurable proportion of progeny having phenotypic characteristics of the new cell type are observed, if essentially no such progeny could form before programming; alternatively, the proportion having characteristics of the new cell type is measurably more than before programming. This process includes differentiation, dedifferentiation and transdifferentiation.

"Differentiation" is the process by which a less specialized cell becomes a more specialized cell type. "Dedifferentiation" is a cellular process in which a partially or terminally differentiated cell reverts to an earlier developmental stage, such as pluripotency or multipotency. "Transdifferentiation" is a process of transforming one differentiated cell type into another differentiated cell type. Typically, transdifferentiation by programming occurs without the cells passing through an intermediate pluripotency stage—i.e., the cells are programmed directly from one differentiated cell type to another differentiated cell type. Under certain conditions, the proportion of progeny with characteristics of the new cell type may be at least about 1%, 5%, 25% or more in order of increasing preference.

"Reprogramming" is a process that confers on a cell a measurably increased capacity to form progeny of at least one new cell type, either in culture or in vivo, than it would have under the same conditions without reprogramming. More specifically, reprogramming is a process that confers on a somatic cell a pluripotent potential. This means that after sufficient proliferation, a measurable proportion of progeny having phenotypic characteristics of the new cell type if essentially no such progeny could form before reprogramming; otherwise, the proportion having characteristics of the new cell type is measurably more than before reprogramming. Under certain conditions, the proportion of progeny with characteristics of the new cell type may be at least about 1%, 5%, 25% or more in order of increasing preference.

The term "forward programming" refers to the programming of a multipotent or pluripotent cell, as opposed to a differentiated somatic cell that has no pluripotency, by the provision of one or more specific lineage-determining genes or gene products to the multipotent or pluripotent cell. For example, forward programming may describe the process of programming ESCs or iPSCs to hematopoietic precursor cells or other precursor cells, or to hematopoietic cells or other differentiated somatic cells.

As used herein, the term "subject" or "subject in need thereof" refers to a mammal, preferably a human being, male or female at any age that is in need of a cell or tissue transplantation. Typically the subject is in need of cell or tissue transplantation (also referred to herein as recipient) due to a disorder or a pathological or undesired condition, state, or syndrome, or a physical, morphological or physiological abnormality which is amenable to treatment via cell or tissue transplantation.

As used herein, a "disruption" of a gene refers to the elimination or reduction of expression of one or more gene products encoded by the subject gene in a cell, compared to the level of expression of the gene product in the absence of the disruption. Exemplary gene products include mRNA and protein products encoded by the gene. Disruption in some cases is transient or reversible and in other cases is permanent. Disruption in some cases is of a functional or full length protein or mRNA, despite the fact that a truncated or non-functional product may be produced. In some embodiments herein, gene activity or function, as opposed to expression, is disrupted. Gene disruption is generally induced by artificial methods, i.e., by addition or introduction of a compound, molecule, complex, or composition, and/or by disruption of nucleic acid of or associated with the gene, such as at the DNA level. Exemplary methods for gene disruption include gene silencing, knockdown, knockout, and/or gene disruption techniques, such as gene editing. Examples include antisense technology, such as RNAi, siRNA, shRNA, and/or ribozymes, which generally result in transient reduction of expression, as well as gene editing techniques which result in targeted gene inactivation or disruption, e.g., by induction of breaks and/or homologous recombination. Examples include insertions, mutations, and deletions. The disruptions typically result in the repression and/or complete absence of expression of a normal or "wild type" product encoded by the gene. Exemplary of such gene disruptions are insertions, frameshift and missense mutations, deletions, knock-in, and knock-out of the gene or part of the gene, including deletions of the entire gene. Such disruptions can occur in the coding region, e.g., in one or more exons, resulting in the inability to produce a full-length product, functional product, or any product, such as by insertion of a stop codon. Such disruptions may also occur by disruptions in the promoter or enhancer or other region affecting activation of transcription, so as to prevent transcription of the gene. Gene disruptions include gene targeting, including targeted gene inactivation by homologous recombination.

"Notch ligand" is a protein capable of binding to a Notch receptor polypeptide present in the membrane of a number of different mammalian cells such as hematopoietic stem cells. The Notch receptors that have been identified in human cells include Notch-1, Notch-2, Notch-3, and Notch-4. Notch ligands typically have a DSL domain (D-Delta, S-Serrate, and L-Lag2) comprising 20 to 22 amino acids at the amino terminus and between 3 to 8 EGF-like repeats (Furie and Furie, 1988; Knust et al., 1987; Suzuki et al., 1987) on the extracellular surface.

"Super donors" are referred to herein as individuals that are homozygous for certain MHC class I and II genes. These homozygous individuals can serve as super donors and their cells, including tissues and other materials comprising their cells, can be transplanted in individuals that are either homozygous or heterozygous for that haplotype. The super donor can be homozygous for the HLA-A, HLA-B, HLA-C, HLA-DR, HLA-DP or HLA-DQ locus/loci alleles, respectively.

The term "chimeric antigen receptors (CARs)," as used herein, may refer to artificial T cell receptors, chimeric T cell receptors, or chimeric immunoreceptors, for example, and encompass engineered receptors that graft an artificial specificity onto a particular immune effector cell. CARs may be employed to impart the specificity of a monoclonal antibody onto a T cell, thereby allowing a large number of specific T cells to be generated, for example, for use in adoptive cell therapy. In specific embodiments, CARs direct specificity of the cell to a tumor associated antigen, for example. In some embodiments, CARs comprise an intracellular activation domain, a transmembrane domain, and an extracellular domain comprising a tumor associated antigen binding region. In particular aspects, CARs comprise fusions of single-chain variable fragments (scFv) derived from monoclonal antibodies, fused to CD3-zeta a transmembrane domain and endodomain. The specificity of other CAR designs may be derived from ligands of receptors (e.g., peptides) or from pattern-recognition receptors, such as Dectins. In certain cases, the spacing of the antigen-recognition domain can be modified to reduce activation-induced cell death. In certain cases, CARs comprise domains for additional co-stimulatory signaling, such as CD3ζ, FcR, CD27, CD28, CD137, DAP10, and/or OX40. In some cases, molecules can be co-expressed with the CAR, including co-stimulatory molecules, reporter genes for imaging (e.g., for positron emission tomography), gene products that conditionally ablate the T cells upon addition of a pro-drug, homing receptors, chemokines, chemokine receptors, cytokines, and cytokine receptors.

The term "antigen presenting cells (APCs)" refers to a class of cells capable of presenting one or more antigens in the form of peptide-MHC complex recognizable by specific effector cells of the immune system, and thereby inducing an effective cellular immune response against the antigen or antigens being presented. APCs can be intact whole cells such as macrophages, B cells, endothelial cells, activated T cells, and dendritic cells; or other molecules, naturally occurring or synthetic, such as purified MHC Class I molecules complexed to 32-microglobulin. While many types of cells may be capable of presenting antigens on their cell surface for T cell recognition, only dendritic cells have the capacity to present antigens in an efficient amount to activate naive T cells for cytotoxic T lymphocyte (CTL) responses.

II. PLURIPOTENT STEM CELLS

In certain embodiments, pluripotent stem cells are engineered to express an antigenic receptor, such as a CAR. The pluripotent stem cells may be stem cells including but are not limited to, induced pluripotent stem cells and embryonic stem cells. In particular aspects, the pluripotent stem cells used herein are human embryonic stem cells (ESCs) or induced pluripotent stem cells (iPSCs) which are capable of long-term proliferation in vitro, while retaining the potential to differentiate into all cell types of the body, including the hematopoietic precursor cells of the present disclosure.

A. Embryonic Stem Cells

In certain aspects, the pluripotent stem cells as ESCs. ES cells are derived from the inner cell mass of blastocysts and have a high in vitro differentiating capability. ES cells can be isolated by removing the outer trophectoderm layer of a developing embryo, then culturing the inner mass cells on a feeder layer of non-growing cells. The replated cells can continue to proliferate and produce new colonies of ES cells which can be removed, dissociated, replated again and allowed to grow. This process of "subculturing" undifferentiated ES cells can be repeated a number of times to produce cell lines containing undifferentiated ES cells (U.S. Pat. Nos. 5,843,780; 6,200,806; 7,029,913). ES cells have the potential to proliferate while maintaining their pluripotency. For example, ES cells are useful in research on cells and on genes which control cell differentiation. The pluripotency of ES cells combined with genetic manipulation and selection can be used for gene analysis studies in vivo via the generation of transgenic, chimeric, and knockout mice.

Methods for producing mouse ES cells are well known. In one method, a preimplantation blastocyst from the 129 strain of mice is treated with mouse antiserum to remove the trophoectoderm, and the inner cell mass is cultured on a feeder cell layer of chemically inactivated mouse embryonic fibroblasts in medium containing fetal calf serum. Colonies of undifferentiated ES cells that develop are subcultured on mouse embryonic fibroblast feeder layers in the presence of fetal calf serum to produce populations of ES cells. In some methods, mouse ES cells can be grown in the absence of a feeder layer by adding the cytokine leukemia inhibitory factor (LIF) to serum-containing culture medium. In other methods, mouse ES cells can be grown in serum-free medium in the presence of bone morphogenetic protein and LIF.

Human ES cells can be produced or derived from a zygote or blastocyst-staged mammalian embryo produced by the fusion of a sperm and egg cell, nuclear transfer, pathogenesis, or the reprogramming of chromatin and subsequent incorporation of the reprogrammed chromatin into a plasma membrane to produce an embryonic cell by previously described methods (Thomson and Marshall, 1998; Reubinoff et al., 2000). In one method, human blastocysts are exposed to anti-human serum, and trophectoderm cells are lysed and removed from the inner cell mass which is cultured on a feeder layer of mouse embryonic fibroblasts. Further, clumps of cells derived from the inner cell mass are chemically or mechanically dissociated, replated, and colonies with undifferentiated morphology are selected by micropipette, dissociated, and replated. In some methods, human ES cells can be grown without serum by culturing the ES cells on a feeder layer of fibroblasts in the presence of basic fibroblast growth factor. In other methods, human ES cells can be grown without a feeder cell layer by culturing the cells on a protein matrix such as MATRIGEL™ or laminin in the presence of "conditioned" medium containing basic fibroblast growth factor (Xu et al., 2001).

ES cells can also be derived from other organisms including rhesus monkey and marmoset by previously described methods (Thomson, and Marshall, 1998; Thomson et al., 1995; Thomson and Odorico, 2000; U.S. Pat. No. 5,843,780), as well as from established mouse and human cell lines. For example, established human ES cell lines include MAOI, MA09, ACT-4, HI, H7, H9, H13, H14 and ACT30. As a further example, mouse ES cell lines that have been established include the CGR8 cell line established from the inner cell mass of the mouse strain 129 embryos, and cultures of CGR8 cells can be grown in the presence of LIF without feeder layers.

ES stem cells can be detected by protein markers including transcription factor Oct4, alkaline phosphatase (AP), stage-specific embryonic antigen SSEA-1, stage-specific embryonic antigen SSEA-3, stage-specific embryonic antigen SSEA-4, transcription factor NANOG, tumor rejection antigen 1-60 (TRA-1-60), tumor rejection antigen 1-81 (TRA-1-81), SOX2, or REX1.

B. Induced Pluripotent Stem Cells

In other aspects, the pluripotent stem cells used herein are induced pluripotent stem (iPS) cells, commonly abbreviated iPS cells or iPSCs. The induction of pluripotency was originally achieved in 2006 using mouse cells (Yamanaka et al. 2006) and in 2007 using human cells (Yu et al. 2007; Takahashi et al. 2007) by reprogramming of somatic cells via the introduction of transcription factors that are linked to pluripotency. The use of iPSCs circumvents most of the ethical and practical problems associated with large-scale clinical use of ES cells, and patients with iPSC-derived autologous transplants may not require lifelong immunosuppressive treatments to prevent graft rejection.

With the exception of germ cells, any cell can be used as a starting point for iPSCs. For example, cell types could be keratinocytes, fibroblasts, hematopoietic cells, mesenchymal cells, liver cells, or stomach cells. T cells may also be used as a source of somatic cells for reprogramming (U.S. Pat. No. 8,741,648). There is no limitation on the degree of cell differentiation or the age of an animal from which cells are collected; even undifferentiated progenitor cells (including somatic stem cells) and finally differentiated mature cells can be used as sources of somatic cells in the methods disclosed herein.

Somatic cells can be reprogrammed to produce iPSCs using methods known to one of skill in the art. One of skill in the art can readily produce induced pluripotent stem cells, see for example, Published U.S. Patent Application No. 20090246875, Published U.S. Patent Application No. 2010/0210014; Published U.S. Patent Application No. 20120276636; U.S. Pat. Nos. 8,058,065; 8,129,187; 8,268,620; PCT Publication NO. WO 2007/069666 A1, and U.S. Pat. No. 8,268,620, which are incorporated herein by reference. Generally, nuclear reprogramming factors are used to produce pluripotent stem cells from a somatic cell. In some embodiments, at least three, or at least four, of Klf4, c-Myc, Oct3/4, Sox2, Nanog, and Lin28 are utilized. In other embodiments, Oct3/4, Sox2, c-Myc and Klf4 are utilized.

Mouse and human cDNA sequences of these nuclear reprogramming substances are available with reference to the NCBI accession numbers mentioned in WO 2007/069666 and U.S. Pat. No. 8,183,038, which are incorporated herein by reference. Methods for introducing one or more reprogramming substances, or nucleic acids encoding these reprogramming substances, are known in the art, and disclosed for example, in U.S. Pat. Nos. 8,268,620, 8,691,574, 8,741,648, 8,546,140, in published U.S. Pat. Nos. 8,900,871 and 8,071,369, which both are incorporated herein by reference.

Once derived, iPSCs can be cultured in a medium sufficient to maintain pluripotency. The iPSCs may be used with various media and techniques developed to culture pluripotent stem cells, more specifically, embryonic stem cells, as described in U.S. Pat. No. 7,442,548 and U.S. Patent Pub. No. 2003/0211603. In the case of mouse cells, the culture is carried out with the addition of Leukemia Inhibitory Factor (LIF) as a differentiation suppression factor to an ordinary medium. In the case of human cells, it is desirable that basic fibroblast growth factor (bFGF) be added in place of LIF. Other methods for the culture and maintenance of iPSCs, as would be known to one of skill in the art, may be used with the present methods.

In certain embodiments, undefined conditions may be used; for example, pluripotent cells may be cultured on fibroblast feeder cells or a medium that has been exposed to fibroblast feeder cells in order to maintain the stem cells in an undifferentiated state. In some embodiments, the cell is cultured in the co-presence of mouse embryonic fibroblasts treated with radiation or an antibiotic to terminate the cell division, as feeder cells. Alternately, pluripotent cells may be cultured and maintained in an essentially undifferentiated state using a defined, feeder-independent culture system, such as a TESR™ medium (Ludwig et al., 2006a; Ludwig et al., 2006b) or E8™/Essential 8™ medium (Chen et al., 2011).

Plasmids have been designed with a number of goals in mind, such as achieving regulated high copy number and avoiding potential causes of plasmid instability in bacteria, and providing means for plasmid selection that are compatible with use in mammalian cells, including human cells. Particular attention has been paid to the dual requirements of plasmids for use in human cells. First, they are suitable for maintenance and fermentation in *E. coli*, so that large amounts of DNA can be produced and purified. Second, they are safe and suitable for use in human patients and animals. The first requirement calls for high copy number plasmids that can be selected for and stably maintained relatively easily during bacterial fermentation. The second requirement calls for attention to elements such as selectable markers and other coding sequences. In some embodiments plasmids that encode a marker are composed of: (1) a high copy number replication origin, (2) a selectable marker, such as, but not limited to, the neo gene for antibiotic selection with kanamycin, (3) transcription termination sequences, including the tyrosinase enhancer and (4) a multicloning site for incorporation of various nucleic acid cassettes; and (5) a nucleic acid sequence encoding a marker operably linked to the tyrosinase promoter. There are numerous plasmid vectors that are known in the art for inducing a nucleic acid encoding a protein. These include, but are not limited to, the vectors disclosed in U.S. Pat. Nos. 6,103,470; 7,598,364; 7,989,425; and 6,416,998, which are incorporated herein by reference.

An episomal gene delivery system can be a plasmid, an Epstein-Barr virus (EBV)-based episomal vector (U.S. Pat. No. 8,546,140), a yeast-based vector, an adenovirus-based vector, a simian virus 40 (SV40)-based episomal vector, a bovine papilloma virus (BPV)-based vector, or a lentiviral vector. A viral gene delivery system can be an RNA-based or DNA-based viral vector.

1. Cells for Production of iPSCs

Certain embodiments of the present disclosure concern a starting population of somatic cells (e.g., blood cells or skin cells) which are reprogrammed to iPSCs. The population of blood cells can include peripheral blood mononuclear cells (PBMC), whole blood or fractions thereof containing mixed populations, spleen cells, bone marrow cells, tumor infiltrating lymphocytes, cells obtained by leukapheresis, biopsy tissue, and lymph nodes, e.g., lymph nodes draining from a tumor. Suitable donors include immunized donors, non-immunized (naive) donors, treated or untreated donors. A "treated" donor is one that has been exposed to one or more biological modifiers. An "untreated" donor has not been exposed to one or more biological modifiers.

In some aspects, the population of blood cells comprises T cells. The T cells can be a purified population of T cells, or alternatively the T cells can be in a population with cells of a different type, such as B cells and/or other peripheral blood cells. The T cells can be a purified population of a subset of T cells, such as $CD4^+$ T cells, or they can be a population of T cells comprising different subsets of T cells. In another embodiment, the T cells are T cell clones that have been maintained in culture for extended periods of time. T cell clones can be transformed to different degrees. In a specific embodiment, the T cells are a T cell clone that proliferates indefinitely in culture.

In some aspects, the T cells are primary T cells. The term "primary T cells" is intended to include T cells obtained from an individual, as opposed to T cells that have been maintained in culture for extended periods of time. Thus, primary T cells are particularly peripheral blood T cells obtained from a subject. A population of primary T cells can be composed of mostly one subset of T cells. Alternatively, the population of primary T cells can be composed of different subsets of T cells.

The T cells can be from previously stored blood samples, from a healthy individual, or alternatively from an individual affected with a condition. The condition can be an infectious disease, such as a condition resulting from a viral infection, a bacterial infection or an infection by any other microorganism, or a hyperproliferative disease, such as cancer like melanoma. In a specific embodiment, the T cells are from an individual infected with a human immunodeficiency virus (HIV). In yet another embodiment, the T cells are from a subject suffering from or susceptible to an autoimmune disease or T cell pathologies. The T cells can be of human origin, murine origin or any other mammalian species.

Methods of obtaining populations of cells comprising T cells are well known in the art. For example, peripheral blood mononuclear cells (PBMC) can be obtained as described according to methods known in the art. Examples of such methods are set forth in the Examples and is discussed by Kim et al. (1992); Biswas et al. (1990); Biswas et al. (1991).

In some aspects, the starting population of blood cells comprises hematopoietic stem cells (HSCs). HSCs normally reside in the bone marrow but can be forced into the blood, a process termed mobilization used clinically to harvest large numbers of HSCs in peripheral blood. One mobilizing agent of choice is granulocyte colony-stimulating factor (G-CSF). $CD34^+$ hematopoietic stem cells or progenitors that circulate in the peripheral blood can be collected by apheresis techniques either in the unperturbed state, or after mobilization following the external administration of hematopoietic growth factors like G-CSF. The number of the stem or progenitor cells collected following mobilization is greater than that obtained after apheresis in the unperturbed state. In some aspects, the source of the cell population is a subject whose cells have not been mobilized by extrinsically applied factors because there is no need to enrich hematopoietic stem cells or progenitor cells.

Methods of obtaining hematopoietic precursor cells from populations of cells are also well known in the art. Hematopoietic precursor cells may be expanded using various cytokines, such as hSCF, hFLT3, and/or IL-3 (Akkina et al., 1996), or $CD34^+$ cells may be enriched using MACS or FACS. As mentioned above, negative selection techniques may also be used to enrich $CD34^+$ cells.

Populations of cells for use in the methods described herein may be mammalian cells, such as human cells, non-human primate cells, rodent cells (e.g., mouse or rat), bovine cells, ovine cells, porcine cells, equine cells, sheep cells, canine cells, and feline cells or a mixture thereof. Non-human primate cells include rhesus macaque cells. The cells may be obtained from an animal, e.g., a human patient, or they may be from cell lines. If the cells are obtained from an animal, they may be used as such, e.g., as unseparated cells (i.e., a mixed population); they may have been established in culture first, e.g., by transformation; or they may have been subjected to preliminary purification methods. For example, a cell population may be manipulated by positive or negative selection based on expression of cell surface markers; stimulated with one or more antigens in vitro or in vivo; treated with one or more biological modifiers in vitro or in vivo; or a combination of any or all of these. In an illustrative embodiment, a cell population is subjected to negative selection for depletion of non-T cells and/or particular T cell subsets. Negative selection can be performed on the basis of cell surface expression of a variety of molecules, including B cell markers such as CD19, and CD20; monocyte marker CD14; the NK cell marker CD56. Alternately, a cell population may be subjected to negative selection for depletion of non-$CD34^+$ hematopoietic cells and/or particular hematopoietic cell subsets. Negative selection can be performed on the basis of cell surface expression of a variety of molecules, such as a cocktail of antibodies (e.g., CD2, CD3, CD11b, CD14, CD15, CD16, CD19, CD56, CD123, CD235a, and CD41 (e.g., for cells of megakaryocyte lineage) which may be used for separation of other cell types, e.g., via MACS or column separation.

It is also possible to obtain a cell sample from a subject, and then to enrich it for a desired cell type. For example, PBMCs and/or $CD34^+$ hematopoietic cells can be isolated from blood as described herein. Counter-flow centrifugation (elutriation) can be used to enrich for T cells from PBMCs. Cells can also be isolated from other cells using a variety of techniques, such as isolation and/or activation with an antibody binding to an epitope on the cell surface of the desired cell type, for example, some T-cell isolation kits use antibody conjugated beads to both activate the cells and then allow column separation with the same beads. Another method that can be used includes negative selection using antibodies to cell surface markers to selectively enrich for a specific cell type without activating the cell by receptor engagement.

Bone marrow cells may be obtained from iliac crest, femora, tibiae, spine, rib or other medullary spaces. Bone marrow may be taken out of the patient and isolated through various separations and washing procedures. A known procedure for isolation of bone marrow cells comprises the following steps: a) centrifugal separation of bone marrow suspension in three fractions and collecting the intermediate fraction, or buffycoat; b) the buffycoat fraction from step (a) is centrifuged one more time in a separation fluid, commonly Ficoll (a trademark of Pharmacia Fine Chemicals AB), and an intermediate fraction which contains the bone marrow cells is collected; and c) washing of the collected fraction from step (b) for recovery of re-transfusable bone marrow cells.

If one desires to use a population of cells enriched in T cells, such populations of cells can be obtained from a mixed population of cells by leukapheresis and mechanical apheresis using a continuous flow cell separator. For example, T cells can be isolated from the buffy coat by any known method, including separation over Ficoll-Hypaque™ gradient, separation over a Percoll gradient, or elutriation.

In certain aspects, T cells are activated by agents that bind to T cell receptors to trigger a signaling cascade for T cell activation. For example, a CD3 antibody may be used. For T cell expansion to a significant number and a proliferating state for reprogramming, a cytokine may also be used, such as IL-2. In a certain aspect, both anti-CD3 and anti-CD28 may be used for T cell activation where co-stimulation is involved. In an alternative aspect, cross-linking of the anti-CD3 may be applied, such as plate bound anti-CD3. If soluble anti-CD3 is used to activate T cells in PBMC, the soluble anti-CD3 antibody may bind to APCs in the PBMC, which then presents the antibody to the T cells. If the soluble anti-CD3 antibody alone is used in a population of purified T-cells, anergy would result for the reasons mentioned above. A certain embodiment comprises culturing T cells in the presence of the anti-CD3 (OKT3) and IL2, which is advantagenous and convenient because there is no need to use costly and cumbersome beads or plate-bound antibody; after adding OKT3 and IL2, the cellular milieu of PBMCs would help activate the T cells. The T cells then overcrowd the other cell types in the PBMC culture due to preferential expansion.

In certain aspects, the starting population of blood cells comprises lymphoblastoid cells, such as from lymphoblastoid cells lines (LCLs). Generation of LCLs is known in the art, for example, by infection of B cells with Epstein-Barr virus (EBV) (Frisan et al., 2001).

2. Reprogramming of Somatic Cells

In some embodiments, the starting population of cells (e.g., T cells) are reprogrammed to iPSCs, such as by the methods described in U.S. Patent Publication No. 2014/

0315304; incorporated herein by reference in its entirety. In certain aspects of the present disclosure, reprogramming factors are expressed from expression cassettes comprised in one or more vectors, such as an integrating vector or an episomal vector. In a further aspect, reprogramming proteins could be introduced directly into somatic cells by protein transduction.

One of skill in the art would be well-equipped to construct a vector through standard recombinant techniques (see, for example, Sambrook et al., 2001 and Ausubel et al., 1996, both incorporated herein by reference). Vectors include but are not limited to, plasmids, cosmids, viruses (bacteriophage, animal viruses, and plant viruses), and artificial chromosomes (e.g., YACs), such as retroviral vectors (e.g. derived from Moloney murine leukemia virus vectors (MoMLV), MSCV, SFFV, MPSV, SNV etc), lentiviral vectors (e.g. derived from HIV-1, HIV-2, SIV, BIV, FIV etc.), adenoviral (Ad) vectors including replication competent, replication deficient and gutless forms thereof, adeno-associated viral (AAV) vectors, simian virus 40 (SV-40) vectors, bovine papilloma virus vectors, Epstein-Barr virus vectors, herpes virus vectors, vaccinia virus vectors, Harvey murine sarcoma virus vectors, murine mammary tumor virus vectors, Rous sarcoma virus vectors.

a. Viral Vectors

Viral vectors may be provided in certain aspects of the present disclosure. In generating recombinant viral vectors, non-essential genes are typically replaced with a gene or coding sequence for a heterologous (or non-native) protein. A viral vector is a kind of expression construct that utilizes viral sequences to introduce nucleic acid and possibly proteins into a cell. The ability of certain viruses to infect cells or enter cells via receptor-mediated endocytosis, and to integrate into host cell genomes and express viral genes stably and efficiently have made them attractive candidates for the transfer of foreign nucleic acids into cells (e.g., mammalian cells). Non-limiting examples of virus vectors that may be used to deliver a nucleic acid of certain aspects of the present disclosure are described below.

Retroviruses have promise as gene delivery vectors due to their ability to integrate their genes into the host genome, transfer a large amount of foreign genetic material, infect a broad spectrum of species and cell types, and be packaged in special cell-lines (Miller, 1992).

In order to construct a retroviral vector, a nucleic acid is inserted into the viral genome in place of certain viral sequences to produce a virus that is replication-defective. In order to produce virions, a packaging cell line containing the gag, pol, and env genes—but without the LTR and packaging components—is constructed (Mann et al., 1983). When a recombinant plasmid containing a cDNA, together with the retroviral LTR and packaging sequences, is introduced into a special cell line (e.g., by calcium phosphate precipitation), the packaging sequence allows the RNA transcript of the recombinant plasmid to be packaged into viral particles, which are then secreted into the culture medium (Nicolas and Rubenstein, 1988; Temin, 1986; Mann et al., 1983). The medium containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136).

Recombinant lentiviral vectors are capable of infecting non-dividing cells and can be used for both in vivo and ex vivo gene transfer and expression of nucleic acid sequences. For example, recombinant lentivirus capable of infecting a non-dividing cell—wherein a suitable host cell is transfected with two or more vectors carrying the packaging functions, namely gag, pol and env, as well as rev and tat—is described in U.S. Pat. No. 5,994,136, incorporated herein by reference.

b. Episomal Vectors

The use of plasmid- or liposome-based extra-chromosomal (i.e., episomal) vectors may be also provided in certain aspects of the present disclosure. Such episomal vectors may include, e.g., oriP-based vectors, and/or vectors encoding a derivative of EBNA-1. These vectors may permit large fragments of DNA to be introduced unto a cell and maintained extra-chromosomally, replicated once per cell cycle, partitioned to daughter cells efficiently, and elicit substantially no immune response.

In particular, EBNA-1, the only viral protein required for the replication of the oriP-based expression vector, does not elicit a cellular immune response because it has developed an efficient mechanism to bypass the processing required for presentation of its antigens on MHC class I molecules (Levitskaya et al., 1997). Further, EBNA-1 can act in trans to enhance expression of the cloned gene, inducing expression of a cloned gene up to 100-fold in some cell lines (Langle-Rouault et al., 1998; Evans et al., 1997). Finally, the manufacture of such oriP-based expression vectors is inexpensive.

Other extra-chromosomal vectors include other lymphotrophic herpes virus-based vectors. Lymphotrophic herpes virus is a herpes virus that replicates in a lymphoblast (e.g., a human B lymphoblast) and becomes a plasmid for a part of its natural life-cycle. Herpes simplex virus (HSV) is not a "lymphotrophic" herpes virus. Exemplary lymphotrophic herpes viruses include, but are not limited to EBV, Kaposi's sarcoma herpes virus (KSHV); Herpes virus saimiri (HS) and Marek's disease virus (MDV). Other sources of episome-base vectors are also contemplated, such as yeast ARS, adenovirus, SV40, or BPV.

One of skill in the art would be well-equipped to construct a vector through standard recombinant techniques (see, for example, Maniatis et al., 1988 and Ausubel et al., 1994, both incorporated herein by reference).

Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide.

Such components also may include markers, such as detectable and/or selection markers that can be used to detect or select for cells that have taken up and are expressing the nucleic acid delivered by the vector. Such components can be provided as a natural feature of the vector (such as the use of certain viral vectors that have components or functionalities mediating binding and uptake), or vectors can be modified to provide such functionalities. A large variety of such vectors are known in the art and are generally available. When a vector is maintained in a host cell, the vector can either be stably replicated by the cells during mitosis as an autonomous structure, incorporated within the genome of the host cell, or maintained in the host cell's nucleus or cytoplasm.

c. Transposon-Based System

In certain aspects, the delivery of programming factors can use a transposon-transposase system. For example, the transposon-transposase system could be the well known Sleeping Beauty, the Frog Prince transposon-transposase system (for a description of the latter, see, e.g., EP1507865), or the TTAA-specific transposon PiggyBac system.

Transposons are sequences of DNA that can move around to different positions within the genome of a single cell, a process called transposition. In the process, they can cause mutations and change the amount of DNA in the genome. Transposons were also once called jumping genes, and are examples of mobile genetic elements.

There are a variety of mobile genetic elements, and they can be grouped based on their mechanism of transposition. Class I mobile genetic elements, or retrotransposons, copy themselves by first being transcribed to RNA, then reverse transcribed back to DNA by reverse transcriptase, and then being inserted at another position in the genome. Class II mobile genetic elements move directly from one position to another using a transposase to "cut and paste" them within the genome.

In particular embodiments, the constructs (e.g., the multi-lineage construct) provided in the present disclosure use a PiggyBac expression system. PiggyBac (PB) DNA transposons mobilize via a "cut-and-paste" mechanism whereby a transposase enzyme (PB transposase), encoded by the transposon itself, excises and re-integrates the transposon at other sites within the genome. PB transposase specifically recognizes PB inverted terminal repeats (ITRs) that flank the transposon; it binds to these sequences and catalyzes excision of the transposon. PB then integrates at TTAA sites throughout the genome, in a relatively random fashion. For the creation of gene trap mutations (or adapted for generating transgenic animals), the transposase is supplied in trans on one plasmid and is co-transfected with a plasmid containing donor transposon, a recombinant transposon comprising a gene trap flanked by the binding sites for the transposase (ITRs). The transposase will catalyze the excision of the transposon from the plasmid and subsequent integration into the genome. Integration within a coding region will capture the elements necessary for gene trap expression. PB possesses several ideal properties: (1) it preferentially inserts within genes (50 to 67% of insertions hit genes) (2) it exhibits no local hopping (widespread genomic coverage) (3) it is not sensitive to over-production inhibition in which elevated levels of the transposase cause decreased transposition 4) it excises cleanly from a donor site, leaving no "footprint," unlike Sleeping Beauty.

d. Regulatory Elements

Expression cassettes included in reprogramming vectors useful in the present disclosure preferably contain (in a 5'-to-3' direction) a eukaryotic transcriptional promoter operably linked to a protein-coding sequence, splice signals including intervening sequences, and a transcriptional termination/polyadenylation sequence.

(i) Promoter/Enhancers

The expression constructs provided herein comprise promoter to drive expression of the programming genes. A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated that the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Non-limiting examples of promoters include early or late viral promoters, such as, SV40 early or late promoters, cytomegalovirus (CMV) immediate early promoters, Rous Sarcoma Virus (RSV) early promoters; eukaryotic cell promoters, such as, e. g., beta actin promoter (Ng, 1989; Quitsche et al., 1989), GADPH promoter (Alexander et al., 1988, Ercolani et al., 1988), metallothionein promoter (Karin et al., 1989; Richards et al., 1984); and concatenated response element promoters, such as cyclic AMP response element promoters (cre), serum response element promoter (sre), phorbol ester promoter (TPA) and response element promoters (tre) near a minimal TATA box. It is also possible to use human growth hormone promoter sequences (e.g., the human growth hormone minimal promoter described at Genbank, accession no. X05244, nucleotide 283-341) or a mouse mammary tumor promoter (available from the ATCC, Cat. No. ATCC 45007).

Tissue-specific transgene expression, especially for reporter gene expression in hematopoietic cells and precursors of hematopoietic cells derived from programming, may be desirable as a way to identify derived hematopoietic cells and precursors. To increase both specificity and activity, the use of cis-acting regulatory elements has been contemplated. For example, a hematopoietic cell-specific promoter may be used. Many such hematopoietic cell-specific promoters are known in the art, such as promoters of the hematopoietic genes provided in Table 1.

In certain aspects, methods of the present disclosure also concern enhancer sequences, i.e., nucleic acid sequences that increase a promoter's activity and that have the potential to act in cis, and regardless of their orientation, even over relatively long distances (up to several kilobases away from the target promoter). However, enhancer function is not necessarily restricted to such long distances as they may also function in close proximity to a given promoter.

Many hematopoietic cell promoter and enhancer sequences have been identified, and may be useful in present methods. See, e.g., U.S. Pat. No. 5,556,954; U.S. Patent App. 20020055144; U.S. Patent App. 20090148425.

(ii) Initiation Signals and Linked Expression

A specific initiation signal also may be used in the expression constructs provided in the present disclosure for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments, internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

Additionally, certain 2A sequence elements could be used to create linked- or co-expression of programming genes in the constructs provided in the present disclosure. For example, cleavage sequences could be used to co-express genes by linking open reading frames to form a single cistron. An exemplary cleavage sequence is the F2A (Foot-and-mouth diease virus 2A) or a "2A-like" sequence (e.g., Thosea asigna virus 2A; T2A). In particular embodiments, an F2A-cleavage peptide is used to link expression of the genes in the multi-lineage construct.

e. Origins of Replication

In order to propagate a vector in a host cell, it may contain one or more origins of replication sites (often termed "ori"), for example, a nucleic acid sequence corresponding to oriP of EBV as described above or a genetically engineered oriP with a similar or elevated function in programming, which is a specific nucleic acid sequence at which replication is initiated. Alternatively a replication origin of other extra-chromosomally replicating virus as described above or an autonomously replicating sequence (ARS) can be employed.

f. Selection and Screenable Markers

In certain embodiments, cells containing a nucleic acid construct may be identified in vitro or in vivo by including a marker in the expression vector. Such markers would confer an identifiable change to the cell permitting easy identification of cells containing the expression vector. Generally, a selection marker is one that confers a property that allows for selection. A positive selection marker is one in which the presence of the marker allows for its selection, while a negative selection marker is one in which its presence prevents its selection. An example of a positive selection marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selection markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes as negative selection markers such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selection and screenable markers are well known to one of skill in the art.

Introduction of a nucleic acid, such as DNA or RNA, into the pluripotent stem cells to be programmed to hematopoietic precursor cells with the current disclosure may use any suitable methods for nucleic acid delivery for transformation of a cell, as described herein or as would be known to one of ordinary skill in the art. Such methods include, but are not limited to, direct delivery of DNA such as by ex vivo transfection (Wilson et al., 1989, Nabel et al, 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); by desiccation/inhibition-mediated DNA uptake (Potrykus et al., 1985), and any combination of such methods. Through the application of techniques such as these, organelle(s), cell(s), tissue(s) or organism(s) may be stably or transiently transformed.

C. MHC Haplotype Matching

Major Histocompatibility Complex (MHC) is the main cause of immune-rejection of allogeneic organ transplants. There are three major class I MHC haplotypes (A, B, and C) and three major MHC class II haplotypes (DR, DP, and DQ). The HLA loci are highly polymorphic and are distributed over 4 Mb on chromosome 6. The ability to haplotype the HLA genes within the region is clinically important since this region is associated with autoimmune and infectious diseases and the compatibility of HLA haplotypes between donor and recipient can influence the clinical outcomes of transplantation. HLAs corresponding to MHC class I present peptides from inside the cell and HLAs corresponding to MHC class II present antigens from outside of the cell to T-lymphocytes. Incompatibility of MHC haplotypes between the graft and the host triggers an immune response against the graft and leads to its rejection. Thus, a patient can be treated with an immunosuppressant to prevent rejection. HLA-matched stem cell lines may overcome the risk of immune rejection.

Because of the importance of HLA in transplantation, the HLA loci are usually typed by serology and PCR for identifying favorable donor-recipient pairs. Serological detection of HLA class I and II antigens can be accomplished using a complement mediated lymphocytotoxicity test with purified T or B lymphocytes. This procedure is predominantly used for matching HLA-A and -B loci. Molecular-based tissue typing can often be more accurate than serologic testing. Low resolution molecular methods such as SSOP (sequence specific oligonucleotide probes) methods, in which PCR products are tested against a series of oligonucleotide probes, can be used to identify HLA antigens, and currently these methods are the most common methods used for Class II-HLA typing. High resolution techniques such as SSP (sequence specific primer) methods which utilize allele specific primers for PCR amplification can identify specific MHC alleles.

MHC compatibility between a donor and a recipient increases significantly if the donor cells are HLA homozygous, i.e. contain identical alleles for each antigen-presenting protein. Most individuals are heterozygous for MHC class I and II genes, but certain individuals are homozygous for these genes. These homozygous individuals can serve as super donors and grafts generated from their cells can be transplanted in all individuals that are either homozygous or heterozygous for that haplotype. Furthermore, if homozygous donor cells have a haplotype found in high frequency in a population, these cells may have application in transplantation therapies for a large number of individuals.

Accordingly, in some embodiments, PSCs of the present methods can be produced from somatic cells of the subject to be treated, or another subject with the same or substantially the same HLA type as that of the patient. In one case, the major HLAs (e.g., the three major loci of HLA-A, HLA-B and HLA-DR) of the donor are identical to the major HLAs of the recipient. In some cases, the somatic cell donor may be a super donor; thus, PSCs derived from a MHC homozygous super donor may be used to generate HPCs and, subsequently, immune cells, such as T cells. Thus, the immune effector cells derived from a super donor may be transplanted in subjects that are either homozygous or heterozygous for that haplotype. For example, the immune cells can be homozygous at two HLA alleles such as HLA-A and HLA-B. As such, immune cells produced from super donors can be used in the methods disclosed herein, to produce immune cells that can potentially "match" a large number of potential recipients.

D. Genetically Engineered Antigenic Receptors

The PSCs can be genetically engineered to express antigen receptors such as engineered TCRs or CARs. For example, the PSCs (e.g, autologous or allogeneic) are modified to express a TCR or CAR having antigenic specificity for a cancer antigen.

Suitable methods of modification are known in the art. See, for instance, Sambrook and Ausubel, supra. For example, the cells may be transduced to express a TCR having antigenic specificity for a cancer antigen using transduction techniques described in Heemskerk et al. *Hum Gene Ther.* 19:496-510 (2008) and Johnson et al. *Blood* 114:535-46 (2009).

Electroporation of RNA coding for the full length TCR α and β (or γ and δ) chains can be used as alternative to overcome long-term problems with autoreactivity caused by pairing of retrovirally transduced and endogenous TCR chains. Even if such alternative pairing takes place in the transient transfection strategy, the possibly generated autoreactive T cells will lose this autoreactivity after some time, because the introduced TCR α and β chain are only transiently expressed. When the introduced TCR α and β chain expression is diminished, only normal autologous T cells are left. This is not the case when full length TCR chains are introduced by stable retroviral transduction, which will never lose the introduced TCR chains, causing a constantly present autoreactivity in the patient.

In some embodiments, the cells comprise one or more nucleic acids introduced via genetic engineering that encode one or more antigen receptors, and genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature (e.g., chimeric).

In some embodiments, the CAR contains an extracellular antigen-recognition domain that specifically binds to an antigen. In some embodiments, the antigen is a protein expressed on the surface of cells. In some embodiments, the CAR is a TCR-like CAR and the antigen is a processed peptide antigen, such as a peptide antigen of an intracellular protein, which, like a TCR, is recognized on the cell surface in the context of a major histocompatibility complex (MHC) molecule.

Exemplary antigen receptors, including CARs and recombinant TCRs, as well as methods for engineering and introducing the receptors into cells, include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., *Cancer Discov.* 2013 April; 3(4): 388-398; Davila et al. (2013) *PLoS ONE* 8(4): e61338; Turtle et al., *Curr. Opin. Immunol.*, 2012 October; 24(5): 633-39; Wu et al., *Cancer,* 2012 Mar. 18(2): 160-75. In some aspects, the genetically engineered antigen receptors include a CAR as described in U.S. Pat. No. 7,446,190, and those described in International Patent Application Publication No.: WO/2014055668 A1.

1. Chimeric Antigen Receptors

In some embodiments, the CAR comprises: a) an intracellular signaling domain, b) a transmembrane domain, and c) an extracellular domain comprising an antigen binding region.

In some embodiments, the engineered antigen receptors include CARs, including activating or stimulatory CARs, costimulatory CARs (see WO2014/055668), and/or inhibitory CARs (iCARs, see Fedorov et al., 2013). The CARs generally include an extracellular antigen (or ligand) binding domain linked to one or more intracellular signaling components, in some aspects via linkers and/or transmembrane domain(s). Such molecules typically mimic or approximate a signal through a natural antigen receptor, a signal through such a receptor in combination with a costimulatory receptor, and/or a signal through a costimulatory receptor alone.

Certain embodiments of the present disclosure concern the use of nucleic acids, including nucleic acids encoding an antigen-specific CAR polypeptide, including a CAR that has been humanized to reduce immunogenicity (hCAR), comprising an intracellular signaling domain, a transmembrane domain, and an extracellular domain comprising one or more signaling motifs. In certain embodiments, the CAR may recognize an epitope comprising the shared space between one or more antigens. In certain embodiments, the binding region can comprise complementary determining regions of a monoclonal antibody, variable regions of a monoclonal antibody, and/or antigen binding fragments thereof. In another embodiment, that specificity is derived from a peptide (e.g., cytokine) that binds to a receptor.

It is contemplated that the human CAR nucleic acids may be human genes used to enhance cellular immunotherapy for human patients. In a specific embodiment, the invention includes a full-length CAR cDNA or coding region. The antigen binding regions or domain can comprise a fragment of the $V_H$ and $V_L$ chains of a single-chain variable fragment (scFv) derived from a particular human monoclonal antibody, such as those described in U.S. Pat. No. 7,109,304, incorporated herein by reference. The fragment can also be any number of different antigen binding domains of a human antigen-specific antibody. In a more specific embodiment, the fragment is an antigen-specific scFv encoded by a sequence that is optimized for human codon usage for expression in human cells.

The arrangement could be multimeric, such as a diabody or multimers. The multimers are most likely formed by cross pairing of the variable portion of the light and heavy chains into a diabody. The hinge portion of the construct can have multiple alternatives from being totally deleted, to having the first cysteine maintained, to a proline rather than a serine substitution, to being truncated up to the first cysteine. The Fc portion can be deleted. Any protein that is stable and/or dimerizes can serve this purpose. One could use just one of the Fc domains, e.g., either the CH2 or CH3 domain from human immunoglobulin. One could also use the hinge, CH2 and CH3 region of a human immunoglobulin that has been modified to improve dimerization. One could also use just the hinge portion of an immunoglobulin. One could also use portions of CD8alpha.

In some embodiments, the CAR nucleic acid comprises a sequence encoding other costimulatory receptors, such as a transmembrane domain and a modified CD28 intracellular signaling domain. Other costimulatory receptors include, but are not limited to one or more of CD28, CD27, OX-40 (CD134), DAP10, and 4-1BB (CD137). In addition to a primary signal initiated by CD3c, an additional signal provided by a human costimulatory receptor inserted in a human CAR is important for full activation of NK cells and could help improve in vivo persistence and the therapeutic success of the adoptive immunotherapy.

In some embodiments, CAR is constructed with a specificity for a particular antigen (or marker or ligand), such as an antigen expressed in a particular cell type to be targeted by adoptive therapy, e.g., a cancer marker, and/or an antigen intended to induce a dampening response, such as an antigen expressed on a normal or non-diseased cell type. Thus, the CAR typically includes in its extracellular portion one or more antigen binding molecules, such as one or more antigen-binding fragment, domain, or portion, or one or more antibody variable domains, and/or antibody molecules. In some embodiments, the CAR includes an antigen-binding portion or portions of an antibody molecule, such as a single-chain antibody fragment (scFv) derived from the variable heavy (VH) and variable light (VL) chains of a monoclonal antibody (mAb).

In certain embodiments of the chimeric antigen receptor, the antigen-specific portion of the receptor (which may be referred to as an extracellular domain comprising an antigen binding region) comprises a tumor associated antigen or a pathogen-specific antigen binding domain. Antigens include carbohydrate antigens recognized by pattern-recognition receptors, such as Dectin-1. A tumor associated antigen may be of any kind so long as it is expressed on the cell surface of tumor cells. Exemplary embodiments of tumor associated antigens include CD19, CD20, carcinoembryonic antigen, alphafetoprotein, CA-125, MUC-1, CD56, EGFR, c-Met, AKT, Her2, Her3, epithelial tumor antigen, melanoma-associated antigen, mutated p53, mutated ras, and so forth.

The sequence of the open reading frame encoding the chimeric receptor can be obtained from a genomic DNA source, a cDNA source, or can be synthesized (e.g., via PCR), or combinations thereof. Depending upon the size of the genomic DNA and the number of introns, it may be desirable to use cDNA or a combination thereof as it is found that introns stabilize the mRNA. Also, it may be further advantageous to use endogenous or exogenous non-coding regions to stabilize the mRNA.

It is contemplated that the chimeric construct can be introduced into immune cells as naked DNA or in a suitable vector. Methods of stably transfecting cells by electroporation using naked DNA are known in the art. See, e.g., U.S. Pat. No. 6,410,319. Naked DNA generally refers to the DNA encoding a chimeric receptor contained in a plasmid expression vector in proper orientation for expression.

Alternatively, a viral vector (e.g., a retroviral vector, adenoviral vector, adeno-associated viral vector, or lentiviral vector) can be used to introduce the chimeric construct into immune cells. Suitable vectors for use in accordance with the method of the present disclosure are non-replicating in the immune cells. A large number of vectors are known that are based on viruses, where the copy number of the virus maintained in the cell is low enough to maintain the viability of the cell, such as, for example, vectors based on HIV, SV40, EBV, HSV, or BPV.

In some aspects, the antigen-specific binding, or recognition component is linked to one or more transmembrane and intracellular signaling domains. In some embodiments, the CAR includes a transmembrane domain fused to the extracellular domain of the CAR. In one embodiment, the transmembrane domain that naturally is associated with one of the domains in the CAR is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 zeta, CD3 epsilon, CD3 gamma, CD3 delta, CD45, CD4, CD5, CD8, CD9, CD 16, CD22, CD33, CD37, CD64, CD80, CD86, CD 134, CD137, CD154, ICOS/CD278, GITR/CD357, NKG2D, and DAP molecules. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain.

In certain embodiments, the platform technologies disclosed herein to genetically modify immune cells, such as NK cells, comprise (i) non-viral gene transfer using an electroporation device (e.g., a nucleofector), (ii) CARs that signal through endodomains (e.g., CD28/CD3-ζ, CD137/CD3-ζ, or other combinations), (iii) CARs with variable lengths of extracellular domains connecting the antigen-recognition domain to the cell surface, and, in some cases, (iv) artificial antigen presenting cells (aAPC) derived from K562 to be able to robustly and numerically expand CAR$^+$ immune cells (Singh et al., 2008; Singh et al., 2011).

2. T Cell Receptor (TCR)

In some embodiments, the genetically engineered antigen receptors include recombinant TCRs and/or TCRs cloned from naturally occurring T cells. A "T cell receptor" or "TCR" refers to a molecule that contains a variable a and β chains (also known as TCRα and TCRβ, respectively) or a variable γ and δ chains (also known as TCRγ and TCRδ, respectively) and that is capable of specifically binding to an antigen peptide bound to a MHC receptor. In some embodiments, the TCR is in the αβ form.

Typically, TCRs that exist in αβ and γδ forms are generally structurally similar, but T cells expressing them may have distinct anatomical locations or functions. A TCR can be found on the surface of a cell or in soluble form. Generally, a TCR is found on the surface of T cells (or T lymphocytes) where it is generally responsible for recognizing antigens bound to major histocompatibility complex (MHC) molecules. In some embodiments, a TCR also can contain a constant domain, a transmembrane domain and/or a short cytoplasmic tail (see, e.g., Janeway et al, Immunobiology: The Immune System in Health and Disease, $3^{rd}$ Ed., Current Biology Publications, p. 433, 1997). For example, in some aspects, each chain of the TCR can possess one N-terminal immunoglobulin variable domain, one immunoglobulin constant domain, a transmembrane region, and a short cytoplasmic tail at the C-terminal end. In some embodiments, a TCR is associated with invariant proteins of the CD3 complex involved in mediating signal transduction. Unless otherwise stated, the term "TCR" should be understood to encompass functional TCR fragments thereof. The term also encompasses intact or full-length TCRs, including TCRs in the αβ form or γδ form.

Thus, for purposes herein, reference to a TCR includes any TCR or functional fragment, such as an antigen-binding portion of a TCR that binds to a specific antigenic peptide bound in an MHC molecule, i.e. MHC-peptide complex. An "antigen-binding portion" or antigen-binding fragment" of a TCR, which can be used interchangeably, refers to a molecule that contains a portion of the structural domains of a TCR, but that binds the antigen (e.g. MHC-peptide complex) to which the full TCR binds. In some cases, an antigen-binding portion contains the variable domains of a TCR, such as variable a chain and variable β chain of a TCR, sufficient to form a binding site for binding to a specific MHC-peptide complex, such as generally where each chain contains three complementarity determining regions.

In some embodiments, the variable domains of the TCR chains associate to form loops, or complementarity determining regions (CDRs) analogous to immunoglobulins, which confer antigen recognition and determine peptide specificity by forming the binding site of the TCR molecule and determine peptide specificity. Typically, like immunoglobulins, the CDRs are separated by framework regions (FRs) (see, e.g., Jores et al., 1990; Chothia et al., 1988; Lefranc et al., 2003). In some embodiments, CDR3 is the main CDR responsible for recognizing processed antigen, although CDR1 of the alpha chain has also been shown to interact with the N-terminal part of the antigenic peptide, whereas CDR1 of the beta chain interacts with the C-terminal part of the peptide. CDR2 is thought to recognize the MHC molecule. In some embodiments, the variable region of the β-chain can contain a further hypervariability (HV4) region.

In some embodiments, the TCR chains contain a constant domain. For example, like immunoglobulins, the extracellular portion of TCR chains (e.g., a-chain, β-chain) can contain two immunoglobulin domains, a variable domain (e.g., $V_a$ or Vp; typically amino acids 1 to 116 based on Kabat numbering Kabat et al., "Sequences of Proteins of Immunological Interest, US Dept. Health and Human Services, Public Health Service National Institutes of Health, 1991, 5$^{th}$ ed.) at the N-terminus, and one constant domain (e.g., a-chain constant domain or $C_a$, typically amino acids 117 to 259 based on Kabat, β-chain constant domain or Cp, typically amino acids 117 to 295 based on Kabat) adjacent to the cell membrane. For example, in some cases, the extracellular portion of the TCR formed by the two chains contains two membrane-proximal constant domains, and two membrane-distal variable domains containing CDRs. The constant domain of the TCR domain contains short connecting sequences in which a cysteine residue forms a disulfide bond, making a link between the two chains. In some embodiments, a TCR may have an additional cysteine residue in each of the α and β chains such that the TCR contains two disulfide bonds in the constant domains.

In some embodiments, the TCR chains can contain a transmembrane domain. In some embodiments, the transmembrane domain is positively charged. In some cases, the TCR chains contains a cytoplasmic tail. In some cases, the structure allows the TCR to associate with other molecules like CD3. For example, a TCR containing constant domains with a transmembrane region can anchor the protein in the cell membrane and associate with invariant subunits of the CD3 signaling apparatus or complex.

Generally, CD3 is a multi-protein complex that can possess three distinct chains (γ, δ, and ε) in mammals and the ζ-chain. For example, in mammals the complex can contain a CD3γ chain, a CD3δ chain, two CD3ε chains, and a homodimer of CD3ζ chains. The CD3γ, CD3δ, and CD3ε chains are highly related cell surface proteins of the immunoglobulin superfamily containing a single immunoglobulin domain. The transmembrane regions of the CD3γ, CD3δ, and CD3ε chains are negatively charged, which is a characteristic that allows these chains to associate with the positively charged T cell receptor chains. The intracellular tails of the CD3γ, CD3δ, and CD3ε chains each contain a single conserved motif known as an immunoreceptor tyrosine-based activation motif or ITAM, whereas each CD3ζ chain has three. Generally, ITAMs are involved in the signaling capacity of the TCR complex. These accessory molecules have negatively charged transmembrane regions and play a role in propagating the signal from the TCR into the cell. The CD3– and ζ-chains, together with the TCR, form what is known as the T cell receptor complex.

In some embodiments, the TCR may be a heterodimer of two chains α and β (or optionally γ and δ) or it may be a single chain TCR construct. In some embodiments, the TCR is a heterodimer containing two separate chains (α and β chains or γ and δ chains) that are linked, such as by a disulfide bond or disulfide bonds. In some embodiments, a TCR for a target antigen (e.g., a cancer antigen) is identified and introduced into the cells. In some embodiments, nucleic acid encoding the TCR can be obtained from a variety of sources, such as by polymerase chain reaction (PCR) amplification of publicly available TCR DNA sequences. In some embodiments, the TCR is obtained from a biological source, such as from cells such as from a T cell (e.g. cytotoxic T cell), T cell hybridomas or other publicly available source. In some embodiments, the T cells can be obtained from in vivo isolated cells. In some embodiments, a high-affinity T cell clone can be isolated from a patient, and the TCR isolated. In some embodiments, the T cells can be a cultured T cell hybridoma or clone. In some embodiments, the TCR clone for a target antigen has been generated in transgenic mice engineered with human immune system genes (e.g., the human leukocyte antigen system, or HLA). In some embodiments, phage display is used to isolate TCRs against a target antigen. In some embodiments, the TCR or antigen-binding portion thereof can be synthetically generated from knowledge of the sequence of the TCR.

3. Antigen-Presenting Cells

APCs, which include macrophages, B lymphocytes, and dendritic cells, are distinguished by their expression of a particular MHC molecule. APCs internalize antigen and re-express a part of that antigen, together with the MHC molecule on their outer cell membrane. The MHC is a large genetic complex with multiple loci. The MHC loci encode two major classes of MHC membrane molecules, referred to as class I and class II MHCs. T helper lymphocytes generally recognize antigen associated with MHC class II molecules, and T cytotoxic lymphocytes recognize antigen associated with MHC class I molecules. In humans the MHC is referred to as the HLA complex and in mice the H-2 complex.

In some cases, aAPCs are useful in preparing therapeutic compositions and cell therapy products of the embodiments. For general guidance regarding the preparation and use of antigen-presenting systems, see, e.g., U.S. Pat. Nos. 6,225,042, 6,355,479, 6,362,001 and 6,790,662.

aAPC systems may comprise at least one exogenous assisting molecule. Any suitable number and combination of assisting molecules may be employed. The assisting molecule may be selected from assisting molecules such as co-stimulatory molecules and adhesion molecules. Exemplary co-stimulatory molecules include CD86, CD64 (FcγRI), 41BB ligand, and IL-21. Adhesion molecules may include carbohydrate-binding glycoproteins such as selectins, transmembrane binding glycoproteins such as integrins, calcium-dependent proteins such as cadherins, and single-pass transmembrane immunoglobulin (Ig) superfamily proteins, such as intercellular adhesion molecules (ICAMs), which promote, for example, cell-to-cell or cell-to-matrix contact. Exemplary adhesion molecules include LFA-3 and ICAMs, such as ICAM-1. Techniques, methods, and reagents useful for selection, cloning, preparation, and expression of exemplary assisting molecules, including co-stimulatory molecules and adhesion molecules, are exemplified in, e.g., U.S. Pat. Nos. 6,225,042, 6,355,479, and 6,362,001.

4. Antigens

Among the antigens targeted by the genetically engineered antigen receptors are those expressed in the context of a disease, condition, or cell type to be targeted via the adoptive cell therapy. Among the diseases and conditions are proliferative, neoplastic, and malignant diseases and disorders, including cancers and tumors, including hematologic cancers, cancers of the immune system, such as lymphomas, leukemias, and/or myelomas, such as B, T, and myeloid leukemias, lymphomas, and multiple myelomas. In some embodiments, the antigen is selectively expressed or over-expressed on cells of the disease or condition, e.g., the tumor or pathogenic cells, as compared to normal or non-targeted cells or tissues. In other embodiments, the antigen is expressed on normal cells and/or is expressed on the engineered cells.

Any suitable antigen may find use in the present method. Exemplary antigens include, but are not limited to, antigenic molecules from infectious agents, auto-/self-antigens, tumor-/cancer-associated antigens, and tumor neoantigens (Linnemann et al., 2015).

Tumor-associated antigens may be derived from prostate, breast, colorectal, lung, pancreatic, renal, mesothelioma, ovarian, or melanoma cancers. Exemplary tumor-associated antigens or tumor cell-derived antigens include MAGE 1, 3, and MAGE 4 (or other MAGE antigens); PRAME; BAGE; RAGE, Lage (also known as NY-ESO-1); SAGE; and HAGE or GAGE. These non-limiting examples of tumor antigens are expressed in a wide range of tumor types such as melanoma, lung carcinoma, sarcoma, and bladder carcinoma. See, e.g., U.S. Pat. No. 6,544,518. Prostate cancer tumor-associated antigens include, for example, prostate specific membrane antigen (PSMA), prostate-specific antigen (PSA), prostatic acid phosphates, NKX3.1, and six-transmembrane epithelial antigen of the prostate (STEAP).

Other tumor associated antigens include Plu-1, HASH-1, HasH-2, Cripto and Criptin. Additionally, a tumor antigen may be a self peptide hormone, such as whole length gonadotrophin hormone releasing hormone (GnRH), a short 10 amino acid long peptide, useful in the treatment of many cancers.

Tumor antigens include tumor antigens derived from cancers that are characterized by tumor-associated antigen expression, such as HER-2/neu expression. Tumor-associated antigens of interest include lineage-specific tumor antigens such as the melanocyte-melanoma lineage antigens MART-1/Melan-A, gp100, gp75, mda-7, tyrosinase and tyrosinase-related protein. Illustrative tumor-associated antigens include, but are not limited to, tumor antigens derived from or comprising any one or more of, p53, Ras, c-Myc, cytoplasmic serine/threonine kinases (e.g., A-Raf, B-Raf, and C-Raf, cyclin-dependent kinases), MAGE-A1, MAGE-A2, MAGE-A3, MAGE-A4, MAGE-A6, MAGE-A10, MAGE-A12, MART-1, BAGE, DAM-6, -10, GAGE-1, -2, -8, GAGE-3, -4, -5, -6, -7B, NA88-A, MART-1, MC1R, Gp100, PSA, PSM, Tyrosinase, TRP-1, TRP-2, ART-4, CAMEL, CEA, Cyp-B, hTERT, hTRT, iCE, MUC1, MUC2, Phosphoinositide 3-kinases (PI3Ks), TRK receptors, PRAME, P15, RU1, RU2, SART-1, SART-3, Wilms' tumor antigen (WT1), AFP, -catenin/m, Caspase-8/m, CEA, CDK-4/m, ELF2M, GnT-V, G250, HSP70-2M, HST-2, KIAA0205, MUM-1, MUM-2, MUM-3, Myosin/m, RAGE, SART-2, TRP-2/INT2, 707-AP, Annexin II, CDC27/m, TPI/mbcr-abl, BCR-ABL, interferon regulatory factor 4 (IRF4), ETV6/AML, LDLR/FUT, Pml/RAR, Tumor-associated calcium signal transducer 1 (TACSTD1) TACSTD2, receptor tyrosine kinases (e.g., Epidermal Growth Factor receptor (EGFR) (in particular, EGFRvIII), platelet derived growth factor receptor (PDGFR), vascular endothelial growth factor receptor (VEGFR)), cytoplasmic tyrosine kinases (e.g., src-family, syk-ZAP70 family), integrin-linked kinase (ILK), signal transducers and activators of transcription STAT3, STAT5, and STATE, hypoxia inducible factors (e.g., HIF-1 and HIF-2), Nuclear Factor-Kappa B (NF-B), Notch receptors (e.g., Notch1-4), c-Met, mammalian targets of rapamycin (mTOR), WNT, extracellular signal-regulated kinases (ERKs), and their regulatory subunits, PMSA, PR-3, MDM2, Mesothelin, renal cell carcinoma-5T4, SM22-alpha, carbonic anhydrases I (CAI) and IX (CAIX) (also known as G250), STEAD, TEL/AML1, GD2, proteinase3, hTERT, sarcoma translocation breakpoints, EphA2, ML-IAP, EpCAM, ERG (TMPRSS2 ETS fusion gene), NA17, PAX3, ALK, androgen receptor, cyclin B1, polysialic acid, MYCN, RhoC, GD3, fucosyl GM1, mesothelian, PSCA, sLe, PLAC1, GM3, BORIS, Tn, GLoboH, NY-BR-1, RGsS, SART3, STn, PAX5, OY-TES 1, sperm protein 17, LCK, HMWMAA, AKAP-4, SSX2, XAGE 1, B7H3, legumain, TIE2, Page4, MAD-CT-1, FAP, MAD-CT-2, fos related antigen 1, CBX2, CLDN6, SPANX, TPTE, ACTL8, ANKRD30A, CDKN2A, MAD2L1, CTAG1B, SUNC1, LRRN1 and idiotype.

Antigens may include epitopic regions or epitopic peptides derived from genes mutated in tumor cells or from genes transcribed at different levels in tumor cells compared to normal cells, such as telomerase enzyme, survivin, mesothelin, mutated ras, bcr/abl rearrangement, Her2/neu, mutated or wild-type p53, cytochrome P450 1B1, and abnormally expressed intron sequences such as N-acetylglucosaminyltransferase-V; clonal rearrangements of immunoglobulin genes generating unique idiotypes in myeloma and B-cell lymphomas; tumor antigens that include epitopic regions or epitopic peptides derived from oncoviral processes, such as human papilloma virus proteins E6 and E7; Epstein bar virus protein LMP2; nonmutated oncofetal proteins with a tumor-selective expression, such as carcinoembryonic antigen and alpha-fetoprotein.

In other embodiments, an antigen is obtained or derived from a pathogenic microorganism or from an opportunistic pathogenic microorganism (also called herein an infectious disease microorganism), such as a virus, fungus, parasite, and bacterium.

In certain embodiments, antigens derived from such a microorganism include full-length proteins.

III. IMMUNE EFFECTOR CELLS

A. Hematopoietic Precursor Cells

The PSCs of the present disclosure engineered to express an antigenic receptor, such as a CAR, may be differentiated to HPCs by methods known in the art. In one method, the CAR-PSCs are differentiated to $CD34^+$ HPCs through directed differentiation. In another method, the CAR-PSCs are differentiated to $CD34^+$ HPCs through forward programming.

1. Directed Differentiation

Certain embodiments of the present disclosure concern the differentiation of CAR-PSCs to HPCs. The CAR-PSCs can be differentiated into HPCs by methods known in the art such as described in U.S. Pat. No. 8,372,642, which is incorporated by reference herein. In one method, combinations of BMP4, VEGF, Flt3 ligand, IL-3, and GM-CSF may be used to promote hematopoietic differentiation. In certain embodiments, the sequential exposure of cell cultures to a first media to prepare PSCs for differentiation, a second media that includes BMP4, VEGF, and FGF, followed by culture in a third media that includes Flt3 ligand, SCF, TPO, IL-3, and IL-6 can differentiate pluripotent cells into HPCs and hematopoietic cells. The second defined media can also comprise heparin. Further, inclusion of FGF-2 (50 ng/ml) in the media containing BMP4 and VEGF can enhance the efficiency of the generation of hematopoietic precursor cells from pluripotent cells. In addition, inclusion of a Glycogen synthase kinase 3 (GSK3) inhibitor (e.g., CHIR99021, BIO, and SB-216763) in the first defined media can further enhance the production of HPCs.

Generally, differentiation of pluripotent cells into hematopoietic precursor cells may be performed using defined or undefined conditions. It will be appreciated that defined conditions are generally preferable in embodiments where the resulting cells are intended to be administered to a human subject. Hematopoietic stem cells may be derived from pluripotent stem cells under defined conditions (e.g., using a TeSR media), and hematopoietic cells may be generated from embryoid bodies derived from pluripotent cells. In other embodiments, pluripotent cells may be co-cultured on OP9 cells or mouse embryonic fibroblast cells and subsequently differentiated.

Pluripotent cells may be allowed to form embryoid bodies or aggregates as a part of the differentiation process. The formation of "embryoid bodies" (EBs), or clusters of growing cells, in order to induce differentiation generally involves in vitro aggregation of human pluripotent stem cells into EBs and allows for the spontaneous and random differentiation of human pluripotent stem cells into multiple tissue types that represent endoderm, ectoderm, and mesoderm origins. Three-dimensional EBs can thus be used to produce some fraction of hematopoietic cells and endothelial cells.

EBs may be formed using the following protocol. Undifferentiated iPSCs adapted to feeder free growth on MATRIGEL™ coated plates may be harvested at confluency using 0.5M EDTA treatment for about 8-10 minutes at room temperature. The EDTA is aspirated after the incubation and the EBs may be formed by collecting the cells in SFD media containing rock inhibitor or blebbistatin. The media may be changed the next day to EB1 differentiation media containing different cytokine formulations. The cells are plated at a density of 0.25-0.5 million cells per ml to promote aggregate formation.

To promote aggregate formation, the cells may be transferred to low-attachment plates for an overnight incubation in serum-free differentiation (SFD) medium, consisting of 75% IMDM (Gibco), 25% Ham's Modified F12 (Cellgro) supplemented with 0.05% N2 and B-27 without RA supplements, 200 mM 1-glutamine, 0.05 mg/ml Ascorbic Acid-2-phosphate Magnesium Salt (Asc 2-P) (WAKO), and $4.5 \times 10^{-4}$ MTG. The next day the cells may be collected from each well and centrifuged. The cells may then be resuspended in "EB differentiation media," which consists of SFD basal media supplemented with about 50 ng/ml bone morphogenetic factor (BMP4), about 50 ng/ml vascular endothelial growth factor (VEGF), and 50 ng/ml zb FGF for the first four days of differentiation. The cells are half fed ever 48 hrs. On the fifth day of differentiation the media is replaced with a second media comprised of SFD media supplemented with 50 ng/ml stem cell factor (SCF), about 50 ng/ml Flt-3 ligand (Flt-3L), 50 ng/ml interleukin-6 (IL-6), 50 ng/ml interleukin-3 (IL-3), 50 ng/ml thrombopoieitin (TPO). The cells are half fed every 48 hrs with fresh differentiation media. The media changes are performed by spinning down the differentiation cultures at 300 g for 5 minutes and aspirating half the volume from the differentiating cultures and replenishing it with fresh media. In certain embodiments, the EB differentiation media may include about BMP4 (e.g., about 50 ng/ml), VEGF (e.g., about 50 ng/ml), and optionally FGF-2 (e.g., about 25-75 ng/ml or about 50 ng/ml). The supernatant may be aspirated and replaced with fresh differentiation medium. Alternately the cells may be half fed every two days with fresh media. The cells may be harvested at different time points during the differentiation process.

HPCs may be cultured from pluripotent stem cells using a defined medium. Methods for the differentiation of pluripotent cells into hematopoietic CD34$^+$ stem cells using a defined media are described, e.g., in U.S. application Ser. No. 12/715,136 which is incorporated by reference in its entirety. It is anticipated that these methods may be used with the present disclosure.

For example, a defined medium may be used to induce hematopoietic CD34$^+$ differentiation. The defined medium may contain the growth factors BMP4, VEGF, Flt3 ligand, IL-3 and/or GMCSF. Pluripotent cells may be cultured in a first defined media comprising BMP4, VEGF, and optionally FGF-2, followed by culture in a second media comprising either (Flt3 ligand, IL-3, and GMCSF) or (Flt3 ligand, IL-3, IL-6, and TPO). The first and second media may also comprise one or more of SCF, IL-6, G-CSF, EPO, FGF-2, and/or TPO. Substantially hypoxic conditions (e.g., less than 20% 02) may further promote hematopoietic or endothelial differentiation.

Cells may be substantially individualized via mechanical or enzymatic means (e.g., using a trypsin or TrypLE™). A ROCK inhibitor (e.g., H1152 or Y-27632) may also be included in the media. It is anticipated that these approaches may be automated using, e.g., robotic automation.

In certain embodiments, substantially hypoxic conditions may be used to promote differentiation of pluripotent cells into hematopoietic progenitor cells. As would be recognized by one of skill in the art, an atmospheric oxygen content of less than about 20.8% would be considered hypoxic. Human cells in culture can grow in atmospheric conditions having reduced oxygen content as compared to ambient air. This relative hypoxia may be achieved by decreasing the atmospheric oxygen exposed to the culture media. Embryonic cells typically develop in vivo under reduced oxygen conditions, generally between about 1% and about 6% atmospheric oxygen, with carbon dioxide at ambient levels. Without wishing to be bound by theory, it is anticipated that hypoxic conditions may mimic an aspect of certain embryonic developmental conditions. As shown in the below examples, hypoxic conditions can be used in certain embodiments to promote additional differentiation of pluripotent cells, such as iPSC or hESC, into a more differentiated cell type, such as HPCs.

The following hypoxic conditions may be used to promote differentiation of pluripotent cells into hematopoietic progenitor cells. In certain embodiments, an atmospheric oxygen content of less than about 20%, less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, less than about 5%, about 5%, about 4%, about 3%, about 2%, or about 1% may be used to promote differentiation into hematopoietic precursor cells. In certain embodiments, the hypoxic atmosphere comprises about 5% oxygen gas.

Regardless of the specific medium being used in any given hematopoietic progenitor cell expansion, the medium used is preferably supplemented with at least one cytokine at a concentration from about 0.1 ng/mL to about 500 ng mL, more usually 10 ng/mL to 100 ng/mL. Suitable cytokines, include but are not limited to, c-kit ligand (KL) (also called steel factor (StI), mast cell growth factor (MGF), and stem cell factor (SCF)), IL-6, G-CSF, IL-3, GM-CSF, IL-1α, IL-11 MIP-1α, LIF, c-mpl ligand/TPO, and flk2/flk3 ligand (Flt2L or Flt3L). Particularly, the culture will include at least one of SCF, Flt3L and TPO. More particularly, the culture will include SCF, Flt3L and TPO.

In one embodiment, the cytokines are contained in the media and replenished by media perfusion. Alternatively, when using a bioreactor system, the cytokines may be added separately, without media perfusion, as a concentrated solution through separate inlet ports. When cytokines are added without perfusion, they will typically be added as a 10× to 100× solution in an amount equal to one-tenth to 1/100 of the volume in the bioreactors with fresh cytokines being added approximately every 2 to 4 days. Further, fresh concentrated cytokines also can be added separately in addition, to cytokines in the perfused media.

In some embodiments, the HPCs exhibit disrupted Methyl-CpG Binding Protein 2 (MeCP2) and are cultured under conditions to promote myeloid differentiation or lymphoid differentiation. In some aspects, the HPCs express a non-functional MeCP2 that has essentially no binding to methylated DNA. In certain aspects, the HPCs do not express MeCP2 at levels that are sufficient to effect MeCP2 DNA binding activity. In particular aspects, the MeCP2 is non-functional by virtue of a truncation or mutation in the MeCP2 gene. In some aspects, obtaining HPCs that exhibit disrupted MeCP2 comprises contacting the HPCs with siRNA, shRNA or a small molecule inhibitor of MeCP2.

(i) Exemplary 3D Differentiation Method

An exemplary method for PSC differentiation to HPCs comprises maintained under feeder-free conditions, such as on MATRIGEL™- or Vitronectin-coated plates in Essential 8 (E8) medium. Aggregates are made from PSCs, particularly sub-confluent, such as <80% confluence) at a density of 0.5-1 million cells per ml in the Essential 3 (E3) medium (e.g., containing only 3 of 8 components of E8 medium: DMEM/F12 basal medium, ascorbic acid (e.g., 100-500 µM), 2-phosphate magnesium and sodium selenite) supplemented with, 50 ng/ml FGF2, 50 ng/ml VEGF, 2 µM CHIR99021 (GSK-3 inhibitor), and blebbistatin (myosin-II inhibitor) (e.g., 2-10 µM, such as 10 µM)). The aggregate formation, and subsequent steps, is performed during 24 hour culture in ultra-low attachment (ULA) flasks under continuous agitation.

The formed cell aggregates (i.e., EBs) are further transferred to serum-free differentiation medium (e.g., 50% IMDM, 50% Hams F12 medium, 100 µg/ml polyvinyl alcohol, 100 µg/ml recombinant human serum albumin, lx non-essential amino acid supplement (Invitrogen), 0.1× chemically-defined lipid supplement (Invitrogen), 125 µM ascorbic acid 2-phosphate magnesium, 0.25 µM linoleic acid, trace element supplements A (0.3×), B (0.2×) and C (0.1×) (Corning), 5 mM sodium chloride, 100 µM monothioglycerol, 20 µM ethanolamine, 100 ng/ml heparin, and 10 ng/ml IGF1) supplemented with hematopoietic mesoderm inducing cytokines—25 ng/ml BMP4, 50 mg/ml VEGF and 50 ng/ml FGF2. Cultures are continued, such as for 4 days, with complete medium change on the second day.

To support differentiation and expansion of hematopoietic CD34+ progenitors, cell aggregates are further transferred to serum-free differentiation medium (as above) supplemented with hematopoietic supportive cytokines, such as 50 ng/ml SCF, 20 mg/ml TPO, 10 ng/ml FLT3L, 20 ng/ml IL-3, and 25 ng/ml BMP4. Cultures are continued, such as for 4 days, with complete medium change on the second day.

The cultures are harvested after the differentiation process, such as 9 days. Single cell suspension is obtained through digestion of differentiated cell aggregates, such as in the Accutase. Isolated CD34+ cells, such as isolated by MACS, are then plated to T/NK differentiation cultures or cryopreserved for later use within 1 hour after isolation.

(ii) Exemplary 2D Differentiation Method

In an alternative exemplary method, the PSCs are subjected to a 2D differentiation protocol for production of HPCs. First, the PSCs are acclimatized to hypoxic conditions, such as for 5-10 passages, under feeder-free conditions, such as on MATRIGEL™—or Vitronectin-coated in Essential 8 (E8) media. PSCs are individualized and plated on PureCoat Amine-coated 6-well plates (Corning Inc.) at a density of 25000/cm$^2$ in the presence Serum Free Defined (SFD) media supplemented with 5 uM blebbistatin (e.g., 2-10 µM, such as 10 µM). The SFD basal medium may contain 75% IMDM (Invitrogen 12200-069) (with Glutamine and 25 mM HEPES+P/S), 25% Hams F12 (Mediatech 10-080-CV), 0.5% N2-supplement (Invitrogen 17502-048), 1% B27 supplement without retinoic acid (Invitrogen 12587-010), 0.05% BSA, 50 ug/ml Ascorbic acid, and 4.5×10−4 M monothioglycerol supplemented with 50 ng/ml of BMP-4, VEGF, and bFGF.

Induction of hematopoietic differentiation is initiated on Day 1 by culturing, for example, in SFD basal medium containing 75% IMDM (Invitrogen 12200-069) (with Glutamine and 25 mM HEPES+P/S), 25% Hams F12 (Mediatech 10-080-CV), 0.5% N2-supplement (Invitrogen 17502-048), 1% B27 supplement without retinoic acid (Invitrogen 12587-010), 0.05% BSA, 50 ug/ml Ascorbic acid, and 4.5×10−4 M monothioglycerol supplemented with 50 ng/ml of BMP4, VEGF, and bFGF. On Day 2, the media is aspirated and the cells are placed in fresh EB1 medium (e.g., SFD basal medium containing 75% IMDM (Invitrogen 12200-069) (with Glutamine and 25 mM HEPES+P/S), 25% Hams F12 (Mediatech 10-080-CV), 0.5% N2-supplement (Invitrogen 17502-048), 1% B27 supplement without retinoic acid (Invitrogen 12587-010), 0.05% BSA, 50 ug/ml Ascorbic acid, and 4.5×10−4 M monothioglycerol supplemented with 50 ng/ml of BMP4, VEGF, and bFGF) for an additional 48 hrs.

On Days 5-10, the media is aspirated and the cells are placed in EB2 media for the next 48 hrs. The EB2 media may comprise fresh SFD basal medium containing 75% IMDM (Invitrogen 12200-069) (with Glutamine and 25 mM HEPES+P/S), 25% Hams F12 (Mediatech 10-080-CV), 0.5% N2-supplement (Invitrogen 17502-048), 1% B27 supplement without retinoic acid (Invitrogen 12587-010), 0.05% BSA, 50 ug/ml Ascorbic acid, and 4.5×10−4 M monothioglycerol supplemented with 50 ng/ml of Flt-3 Ligand, IL3, IL6, SCF, and TPO each at 50 ng/ml and 5000 U/ml of heparin. The cells are harvested at day 7, 8, 9, 10 of differentiation using TrypLE and stained for the presence of HPC markers and lymphoid progenitors.

2. Forward Programming

Certain embodiments of the present disclosure provide HPCs by forward programming of the CAR-PSCs via expression of a combination of programming genes important for hematopoietic cell differentiation/function. In one method, the PSCs are modified to express at least three hematopoietic precursor programming genes such as an ETS gene (e.g., ETC2 or ERG), a hematopoietic development gene (e.g., GATA2), and a homoebox gene (e.g., HOXA9), such as described in PCT/US2016/057893, incorporated herein by reference in its entirety. In particular aspects, the ETV2/ERG, GATA2, and HOXA9 genes are co-expressed by one vector, such as an inducible PiggyBac vector, using a bi-directional Tight promoter which is transfected into the CAR-PSCs.

Further, the EGH-CAR-PSCs may be further modified to express additional genes for long-term engraftment potential. Exemplary genes include HMGA2, MYCN, NR4A2, SOX17, TFEC, MEIS1, HOXA4, ZNF414, KLF4, ZNF131, BCL2, ETV6, ZNF350, and/or RBAK. For example, the PSCs may be transfected with one or more vectors to express HMGA2, MYCN, NR4A2, SOX17, TFEC, MEIS1, and HOXA4.

Preferably, the ETV2/GAT2/HOXA9 genes are expressed for only a period of time sufficient to forward program the PSCs into hematopoietic precursor cells. Accordingly, the hematopoietic precursor programming genes can be under the control of an inducible promoter. Thus, the expression of the hematopoietic precursor programming genes can be induced in the PSCs for a period of time sufficient to forward program to the multi-lineage hematopoietic precursor cells. The period of time can be about 1 day to about 20 days, such as about 3, 4, 5, 6, 7, 8, 9, or 10 days. Alternatively, the hematopoietic precursor programming genes can be introduced to the PSCs by an episomal vector. Thus, the hematopoietic precursor programming genes could be transiently expressed in the PSCs.

B. Lymphoid Cell Differentiation

The HPCs can then be further differentiated to lymphoid lineage cells, including T cells, NK cells, and T/NK cells. In some aspects, HPCs during differentiation are isolated at Day 7-12, such as Day 8-11, for differentiation to lymphoid cells. The HPCs at this stage may be identified by expression of CD34 and CD43. In addition the HPCs with lymphoid potential can express CD144, DLL4, CD7 and CD235 at low levels which decline at Day 11, implying that a certain threshold level of expression of these markers is needed to prime cells towards lymphoid differentiation in the presence of DLL4.

In some aspects, HPCs isolated at day 7-11, such as day 7, day 8, day 9, day 10 or day 11 of the differentiation process can be differentiated to lymphoid cells such as T and NK cells. In some aspects, the timing of the origin for lymphoid progenitors coincides with the decline of hematoendothelial progenitors and the emergence of erythroid progenitors during HPC differentiation. In particular aspects, Day 9 HPCs may have an increased efficiency at generating T cells. HPCs capable of lymphoid differentiation can be isolated and/or identified by the expression of certain markers. For example, cells with surface expression of CD34 and/or CD43, particularly expressing both CD34 and CD43, may be selected for lymphoid differentiation, such as by MACS sorting.

Additional markers for detecting lymphoid progenitors include DLL4, CD144, CD31, CD34, CD43$^{lo}$, CD45$^{lo/-}$, CD235, CD7, Flk-1, APNLR. In particular aspects, the presence of CD34/CD7, CD235/CD7, DLL4/CD34, DLL4/CD31, DLL4/CD144, or CD34/CD43$^{lo}$ double positive populations is used to identify lymphoid progenitors. CD144 expression on HPCs co stains with CD31, CD34 and DLL4. CD7 expression on HPCs co-stains with CD235, CD34 and CD43. Hence HPCs co-expressing CD144 and CD7 demonstrate lymphoid potential capture precursors expressing membrane bound notch ligand (DLL4) along with hematoendothelial markers and create the phenotypic signature for emerging lymphoid progenitors capable of generating lineages of definitive hematopoiesis in vitro. In particular aspects, the HPCs may be further sorted into cells with enhanced lymphoid potential by sorting of the surface markers including CD31, CD34, CD144, CD43, CD45, CD6, CD335, Flk-1, and DLL4. In some aspects, the positive fractions of CD114/CD34, CD144/CD45, CD144/CD7, and CD144/CD34/CD45/CD7 of HPCs are differentiated to lymphoid cells. In particular aspects, the CD144/CD7 positive fractions of HPCs is differentiated to lymphoid cells.

The HPCs may be cultured in defined, feeder free conditions for lymphoid differentiation. A culture media may contain one or more matrix components, such as RetroNectin, fibronectin or a RGD peptide. Without wishing to be bound by any theory, a matrix component may provide a solid support for the growth of embryonic stem cells. In certain embodiments, a matrix component may be applied to a culturing surface and contacted with culture media prior to seeding cells into the media. For example, cells may be cultured in a defined media (e.g., a TeSR media) on plates coated with fibronectin or MATRIGEL™ prior to mechanically separating the cells into clumps or individualizing cells and inducing differentiation into hematopoietic precursor cells.

Various matrix components may be used to culture pluripotent cells including a collagen (e.g., collagen IV), laminin, vitronectin, MATRIGEL™, gelatin, polylysine, thrombospondin (e.g., TSP-1, -2, -3, -4 and/or -5), and/or PRONECTIN-F™. In certain embodiments, the use of only MATRIGEL™, collagen IV, or laminin with cells previously cultured using TeSR may be avoided due to possible adverse effects on cell viability; nonetheless, these compositions may be advantageously used in combination with other matrix components. Combinations of these matrix components may provide additional benefit for promoting cell growth and cell viability. In certain embodiments, 1, 2, 3, 4, 5, 6, or more of the above matrix components may be used to culture cells, e.g., prior to hematopoietic differentiation.

In some embodiments, ascorbic acid may be used to enhance lymphoid differentiation. The defined media may be supplemented with about 10 µM to about 1 mM ascorbic acid, such as 100 to 500 µM, such as about 50 µM to about 100 µM, such as about 95 µM. The ascorbic acid may be selected from various ascorbates, such as ascorbic acid magnesium phosphate. In some embodiments, nicotinamide (e.g., nicotinic acid) may be used to enhance lymphoid differentiation, such as at a concentration of about 0.1 mM to about 5 mM.

In some aspects, the HPCs are differentiated to lymphoid cells, such as T cells, by altering the endogenous activity of a Notch ligand by administering a substance that increases the production of the Notch ligand in a subject. The method also includes culturing the cells in a medium, wherein the medium includes an effective amount of a notch ligand and one or more cytokines selected from the group consisting of IL-7, IL-15, SCF, Flt-3 and IL-3. In some particular embodiments, the medium can further include IL-6. In some embodiments, the notch ligand is delta4 notch ligand (DLL4), such as DLL4:Fc chimera.

A Notch ligand is selected that promotes and maintains differentiation and proliferation of cells of the T cell lineage. A Notch ligand may be human in origin, or may be derived from other species, including mammalian species such as rodent, dog, cat, pig, sheep, cow, goat, and primates. Particular examples of Notch Ligands include the Delta family. The Delta family includes Delta-1 (Genbank Accession No. AF003522, *Homo sapiens*), Delta-3 (Genbank Accession No. AF084576, *Rattus norvegicus*), Delta-like 1 (Genbank Accession No. NM-005618 and NP-005609, *Homo sapiens*; Genbank Accession No. X80903, 148324, *M. musculus*), Delta-like 3 (Genbank Accession No. NM 053666, N-446118, *Rattus norvegicus*), Delta-4 (Genbank Accession No. AF273454, BAB18580, *Mus musculus*; Genbank Accession No. AF279305, AAF81912, *Homo sapiens*), and Delta-like 4 (Genbank Accession. No. Q9NR61, AAF76427, AF253468, NM-019074, *Homo sapiens*; Genbank Accession No. NM-019454, *Mus musculus*). Notch ligands are commercially available or can be produced by recombinant DNA techniques and purified to various degrees.

The method further includes the step of maintaining the HPC cells in the culture described above for a duration of time sufficient to produce differentiated NK cells. In some embodiments, differentiated NK cells emerge in the cultures along with T cells, however the NK cells may cease to proliferate after week 6. In general, the determination of an increase in the number of NK cells and/or their state of differentiation is assessed using conventional methods known to those of ordinary skill in the art. For example, the cultured cells may be monitored by flow cytometry for the development of NK cells by staining the cells with anti-CD56 and anti-CD3 antibodies. The anti-CD3 antibody, such as OKT3, may be present at a concentration of 0.5 to 2 μg. Cells which are CD56+/CD3 would be indicative of differentiated NK cells.

In particular aspects, the lymphoid differentiation to $CD3^+$ T cells or $CD56^+CD3^-$ NK cells is performed by 2D hypoxic culture on retronectin and DLL4-coated plates. In particular aspects, a nontissue culture-treated plate may be coated with DLL4:Fc chimera protein and RetroNectin (fibronectin fragment CH-296; Takara Shuzo, Japan) for use in lymphoid differentiation of HPCs. The differentiation may comprise a first period of T/NK cell differentiation followed by a second period of T or NK cell expansion. The first period of differentiation may be for about 1 week to about 2 weeks, and the second period of expansion may also be for about 1 week to about 2 weeks. Thus, the complete period of lymphoid differentiation and expansion may be for about 2-4 weeks.

In some embodiments, the lymphoid differentiation process may comprise co-culture with antigen-specific target cells, such as antigen-specific tumor cells, to increase the cytotoxic activity of the T cells and NK cells. In particular aspects, the expansion period of lymphoid differentiation may comprise co-culture with antigen-specific target cells. For example, CD19-CAR-T cells or NK cells may be co-cultured with CD19+ tumor cells (e.g., CD19+ Daudi cells) during the expansion period, such as for one to three weeks, particularly two weeks. In some aspects, the expansion period may further comprise the addition of cytokines, such as IL2, IL15, and/or IL21, particularly IL2, to improve expansion. The concentration of the cytokines may be optimized, such as 10 to 50 μM.

C. Cell Culture

In certain embodiments, substantially hypoxic conditions may be used to promote differentiation of HPCs to myeloid or lymphoid lineages. In certain embodiments, an atmospheric oxygen content of less than about 20%, less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, less than about 5%, about 5%, about 4%, about 3%, about 2%, or about 1% may be used to promote differentiation into hematopoietic precursor cells. In certain embodiments, the hypoxic atmosphere comprises about 5% oxygen gas.

As described herein, one or more defined culture medium may be advantageously used to promote the differentiation of HPCs to myeloid and lymphoid lineages; in particular, the elimination of animal products such as serum and mouse feeder layers can reduce the risks associated with exposure of cells to animal products and allow for the generation of cells that could be more safely administered to a human subject. As traditional stem cell culture development has relied on serum products and mouse feeder layers for differentiating stem cells into a variety of cell types, these traditional procedures have limited the scale on which differentiation can be conducted, increased biological variability and potential contamination, and severely hampered the use of ES cells in translational therapies in which they might otherwise prove useful.

Generally, cells of the present disclosure are cultured in a culture medium, which is a nutrient-rich buffered solution capable of sustaining cell growth. Culture media suitable for isolating, expanding and differentiating pluripotent stem cells into hematopoietic precursor cells and hematopoietic cells according to the method described herein include but not limited to high glucose Dulbecco's Modified Eagle's Medium (DMEM), DMEM/F-15, RPMI 1640, Iscove's modified Dubelcco's media (IMDM), and Opti-MEM SFM (Invitrogen Inc.). Chemically Defined Medium comprises a minimum essential medium such as Iscove's Modified Dulbecco's Medium (IMDM) (Gibco), supplemented with human serum albumin, human ExCyte lipoprotein, transferrin, insulin, vitamins, essential and non-essential amino acids, sodium pyruvate, glutamine and a mitogen is also suitable. As used herein, a mitogen refers to an agent that stimulates division of a cell. An agent can be a chemical, usually some form of a protein that encourages a cell to commence cell division, triggering mitosis. In one embodiment, serum free media such as those described in U.S. Ser. No. 08/464,599 and WO 96/39487, and the "complete media" as described in U.S. Pat. No. 5,486,359 are contemplated for use with methods described herein. In some embodiments, the culture medium is supplemented with 10% Fetal Bovine Serum (FBS), human autologous serum, human AB serum or platelet rich plasma supplemented with heparin (2 U/ml).

Immune cells can be generated by culturing pluripotent stem cells or hematopoietic precursor cells in a medium under conditions that increase the intracellular level of factors sufficient to promote differentiation of the cells into myeloid or lymphoid lineages. The medium may also contain one or more hematopoietic cell differentiation and maturation agents, like various kinds of growth factors. These agents may either help induce cells to commit to a more mature phenotype—or preferentially promote survival of the mature cells—or have a combination of both of these effects. Differentiation and maturation agents may include soluble growth factors (peptide hormones, cytokines, ligand-receptor complexes, and other compounds) that are capable of promoting the growth of cells of the hematopoietic cell lineage. Non-limiting examples of such agents include but are not limited to hematopoietic or endothelial growth factors such as fibroblast growth factor (FGF), vascular endothelial growth factor (VEGF), stem cell factor (SCF), thrombopoietin (TPO), FLT-3 ligand (FLT3L), interleukin-3 (IL-3), interleukin-6 (IL-6), interleukin-9 (IL-9), or granulocyte colony-stimulating factor (G-CSF), or isoforms or variants thereof.

IV. USES OF ANTIGEN-SPECIFIC IMMUNE CELLS

The antigen-specific immune effector cells provided by methods and compositions of certain aspects can be used in a variety of applications. These include but are not limited to transplantation or implantation of the cells in vivo; screening cytotoxic compounds, carcinogens, mutagens growth/regulatory factors, pharmaceutical compounds, etc., in vitro; elucidating the mechanism of hematological diseases and injuries; studying the mechanism by which drugs and/or growth factors operate; diagnosing and monitoring cancer in a patient; gene therapy; and the production of biologically active products, to name but a few.

A. Test Compound Screening

Immune cells of this disclosure can be used to screen for factors (such as solvents, small molecule drugs, peptides, and polynucleotides) or environmental conditions (such as culture conditions or manipulation) that affect the characteristics of lymphoid cells provided herein.

Particular screening applications of this disclosure relate to the testing of pharmaceutical compounds in drug research. The reader is referred generally to the standard textbook *In vitro Methods in Pharmaceutical Research*, Academic Press, 1997, and U.S. Pat. No. 5,030,015. In certain aspects, myeloid and lymphoid cells play the role of test cells for standard drug screening and toxicity assays, as have been previously performed on hematopoietic cells and precursors in short-term culture. Assessment of the activity of candidate pharmaceutical compounds generally involves combining the hematopoietic cells or precursors provided in certain aspects with the candidate compound, determining any change in the morphology, marker phenotype, or metabolic activity of the cells that is attributable to the compound (compared with untreated cells or cells treated with an inert compound), and then correlating the effect of the compound with the observed change. The screening may be done either because the compound is designed to have a pharmacological effect on hematopoietic cells or precursors, or because a compound designed to have effects elsewhere may have unintended effects on hematopoietic cells or precursors. Two or more drugs can be tested in combination (by combining with the cells either simultaneously or sequentially), to detect possible drug-drug interaction effects.

B. Adoptive Cell Therapy

In some embodiments, the present disclosure provides methods for immunotherapy comprising administering an effective amount of the immune cells of the present disclosure. In one embodiments, a medical disease or disorder is treated by transfer of an immune cell population that elicits an immune response. In certain embodiments of the present disclosure, cancer or infection is treated by transfer of an immune cell population that elicits an immune response. Provided herein are methods for treating or delaying progression of cancer in an individual comprising administering to the individual an effective amount an antigen-specific cell therapy. The present methods may be applied for the treatment of immune disorders, solid cancers, hematologic cancers, and viral infections.

Tumors for which the present treatment methods are useful include any malignant cell type, such as those found in a solid tumor or a hematological tumor. Exemplary solid tumors can include, but are not limited to, a tumor of an organ selected from the group consisting of pancreas, colon, cecum, stomach, brain, head, neck, ovary, kidney, larynx, sarcoma, lung, bladder, melanoma, prostate, and breast. Exemplary hematological tumors include tumors of the bone marrow, T or B cell malignancies, leukemias, lymphomas, blastomas, myelomas, and the like. Further examples of cancers that may be treated using the methods provided herein include, but are not limited to, lung cancer (including small-cell lung cancer, non-small cell lung cancer, adenocarcinoma of the lung, and squamous carcinoma of the lung), cancer of the peritoneum, gastric or stomach cancer (including gastrointestinal cancer and gastrointestinal stromal cancer), pancreatic cancer, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, and melanoma.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis *Coli*; Solid carcinoma; carcinoid tumor, malignant; branchioloalveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; lentigo malignant melanoma; acral lentiginous melanomas; nodular melanomas; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; B-cell lymphoma; low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; Waldenstrom's macroglobulinemia; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; hairy cell leukemia; chronic lymphocytic leukemia (CLL); acute lymphoblastic leukemia (ALL); acute myeloid leukemia (AML); and chronic myeloblastic leukemia.

To determine the suitability of cells provided herein for therapeutic applications, the cells can first be tested in a suitable animal model. At one level, cells are assessed for their ability to survive and maintain their phenotype in vivo. Cells provided herein are administered to immunodeficient animals (such as NOG mice, or animals rendered immunodeficient chemically or by irradiation) at a site amenable for further observation, such as under the kidney capsule, into the spleen, into a liver lobule, or into the bone marrow. Tissues are harvested after a period of a few days to several weeks or more, and assessed as to whether starting cell types such as erythrocytes are still present. This can be performed by providing the administered cells with a detectable label (such as green fluorescent protein, or (3-galactosidase); or by measuring a constitutive marker specific for the administered human cells. Where cells provided herein are being tested in a rodent model, the presence and phenotype of the administered cells can be assessed by immunohistochemistry or ELISA using human-specific antibody, or by RT-PCR analysis using primers and hybridization conditions that cause amplification to be specific for human polynucleotide sequences. Suitable markers for assessing gene expression at the mRNA or protein level are provided elsewhere in this disclosure.

Immune cells provided by methods of the present disclosure may be tested in various animal models for their ability to treat hematological disorders and injuries. For example, a sickle cell anemia mouse model or the T/B cell-deficient Rag-2 knockout mouse may be particularly useful animal models for testing the myeloid and lymphoid cells disclosed herein.

Immune cells provided in certain aspects of the present disclosure that demonstrate desirable functional characteristics or efficacy in animal models, may also be suitable for direct administration to human subjects in need thereof. For purposes of hemostasis, the cells can be administered at any site that has adequate access to the circulation. Hematopoietic cells or precursors thereof may also be delivered at a site of injury or disease.

The cells provided in certain aspects of this present disclosure can be used for therapy of any subject in need thereof. Human conditions that may be appropriate for such therapy include the various anemias and hemoglobinopathies, as well as diseases characterized by decreased numbers of hematopoietic cells (such as, for example, myelodysplastic syndrome, myelofibrosis, neutropenia, agranulocytosis, Glanzmann's thrombasthenia, thrombocytopenia, and acquired immune deficiency syndrome). For human therapy, the dose is generally between about $10^9$ and $10^{12}$ cells, and typically between about $5\times10^9$ and $5\times10^{10}$ cells, making adjustments for the body weight of the subject, nature and severity of the affliction, and the replicative capacity of the administered cells. The ultimate responsibility for determining the mode of treatment and the appropriate dose lies with the managing clinician.

Therapeutically effective amounts of immune cells can be administered by a number of routes, including parenteral administration, for example, intravenous, intraperitoneal, intramuscular, intrasternal, or intraarticular injection, or infusion.

The therapeutically effective amount of immune cells for use in adoptive cell therapy is that amount that achieves a desired effect in a subject being treated. For instance, this can be the amount of immune cells necessary to inhibit advancement, or to cause regression of an autoimmune or alloimmune disease, or which is capable of relieving symptoms caused by an autoimmune disease, such as pain and inflammation. It can be the amount necessary to relieve symptoms associated with inflammation, such as pain, edema and elevated temperature. It can also be the amount necessary to diminish or prevent rejection of a transplanted organ.

The immune cell population can be administered in treatment regimens consistent with the disease, for example a single or a few doses over one to several days to ameliorate a disease state or periodic doses over an extended time to inhibit disease progression and prevent disease recurrence. The precise dose to be employed in the formulation will also depend on the route of administration, and the seriousness of the disease or disorder, and should be decided according to the judgment of the practitioner and each patient's circumstances. The therapeutically effective amount of immune cells will be dependent on the subject being treated, the severity and type of the affliction, and the manner of administration. In some embodiments, doses that could be used in the treatment of human subjects range from at least $3.8\times10^4$, at least $3.8\times10^5$, at least $3.8\times10^6$, at least $3.8\times10^7$, at least $3.8\times10^8$, at least $3.8\times10^9$, or at least $3.8\times10^{10}$ immune cells/m$^2$. In a certain embodiment, the dose used in the treatment of human subjects ranges from about $3.8\times10^9$ to about $3.8\times10^{10}$ immune cells/m$^2$. In additional embodiments, a therapeutically effective amount of immune cells can vary from about $5\times10^6$ cells per kg body weight to about $7.5\times10^8$ cells per kg body weight, such as about $2\times10^7$ cells to about $5\times10^8$ cells per kg body weight, or about $5\times10^7$ cells to about $2\times10^8$ cells per kg body weight. The exact amount of immune cells is readily determined by one of skill in the art based on the age, weight, sex, and physiological condition of the subject. Effective doses can be extrapolated from dose-response curves derived from in vitro or animal model test systems.

The immune cells may be administered in combination with one or more other therapeutic agents for the treatment of the immune-mediated disorder. Combination therapies can include, but are not limited to, one or more antimicrobial agents (for example, antibiotics, anti-viral agents and anti-fungal agents), anti-tumor agents (for example, fluorouracil, methotrexate, paclitaxel, fludarabine, etoposide, doxorubicin, or vincristine), immune-depleting agents (for example, fludarabine, etoposide, doxorubicin, or vincristine), immunosuppressive agents (for example, azathioprine, or glucocorticoids, such as dexamethasone or prednisone), anti-inflammatory agents (for example, glucocorticoids such as hydrocortisone, dexamethasone or prednisone, or non-steroidal anti-inflammatory agents such as acetylsalicylic acid, ibuprofen or naproxen sodium), cytokines (for example, interleukin-10 or transforming growth factor-beta), hormones (for example, estrogen), or a vaccine. In addition, immunosuppressive or tolerogenic agents including but not limited to calcineurin inhibitors (e.g., cyclosporin and tacrolimus); mTOR inhibitors (e.g., Rapamycin); mycophenolate mofetil, antibodies (e.g., recognizing CD3, CD4, CD40, CD154, CD45, IVIG, or B cells); chemotherapeutic agents (e.g., Methotrexate, Treosulfan, Busulfan); irradiation; or chemokines, interleukins or their inhibitors (e.g., BAFF, IL-2, anti-IL-2R, IL-4, JAK kinase inhibitors) can be administered. Such additional pharmaceutical agents can be administered before, during, or after administration of the immune cells, depending on the desired effect. This administration of the cells and the agent can be by the same route or by different routes, and either at the same site or at a different site.

C. Pharmaceutical Compositions

Also provided herein are pharmaceutical compositions and formulations comprising immune cells (e.g., T cells or NK cells) and a pharmaceutically acceptable carrier. Administration can be autologous or non-autologous. For example, T cells and/or NK cells and compositions comprising thereof can be obtained from one subject, and administered to the same subject or a different, compatible subject. Immune cells of the present disclosure can be administered via localized injection, including catheter administration, systemic injection, localized injection, intravenous injection, or parenteral administration. When administering a therapeutic composition of the present disclosure, it will generally be formulated in a unit dosage injectable form (e.g., solution, suspension, emulsion).

Pharmaceutical compositions and formulations as described herein can be prepared by mixing the active ingredients (such as an antibody or a polypeptide) having the desired degree of purity with one or more optional pharmaceutically acceptable carriers (Remington's Pharmaceutical Sciences 22$^{nd}$ edition, 2012), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Derivation of Anti-CD19 CAR-Expressing PSC-Derived T/NK Cells

In order to generate pluripotent stem cells which express a chimeric antigen receptor (CAR), two separate methods were used. In one method, transgene-free PSCs were derived from T cells using retroviral vectors to produce 1C cells (US20160257939; incorporated herein by reference in its entirety) or epiosomal vectors to produce E11 cells. In the second method, PSCs were transfected with a PiggyBac expression vector encoding hematopoietic programming genes ETV2/ERG, GATA2, and HOXA9 (engineered H1 ESCs with introduced DOX-inducible ETV2-GATA2-HOXA9 (EGH) hematopoietic programming genes) to produce A16 cells. The PSCs from both methods were then genetically modified to constitutively express a second generation anti-human CD19 chimeric antigen receptor (CAR) composed of the FMC63 mAb-derived human CD19-binding scFv domain, CD28 co-stimulatory domain and CD3ζ signaling domain.

Figure 1B:
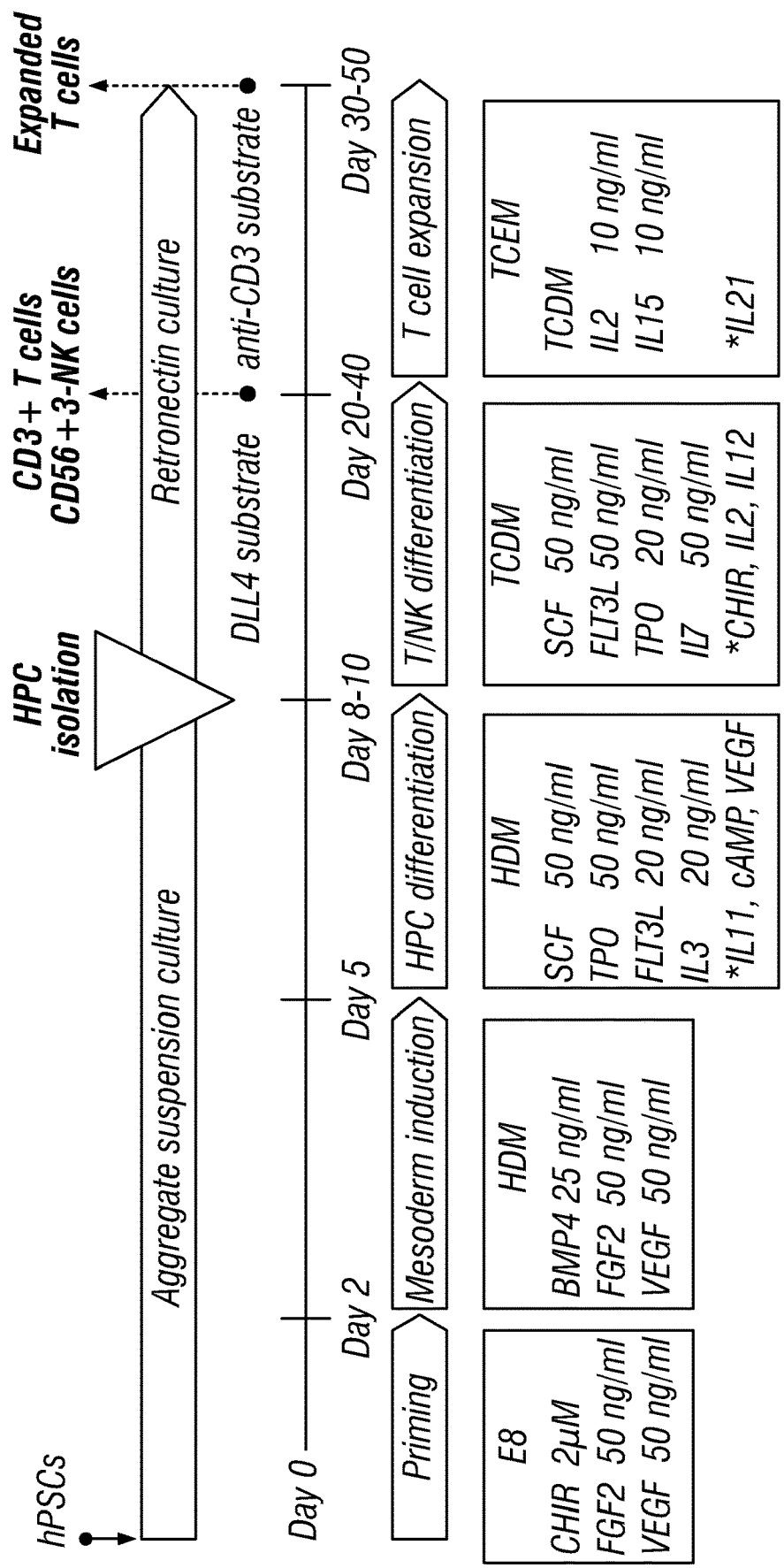
Figure 1C:
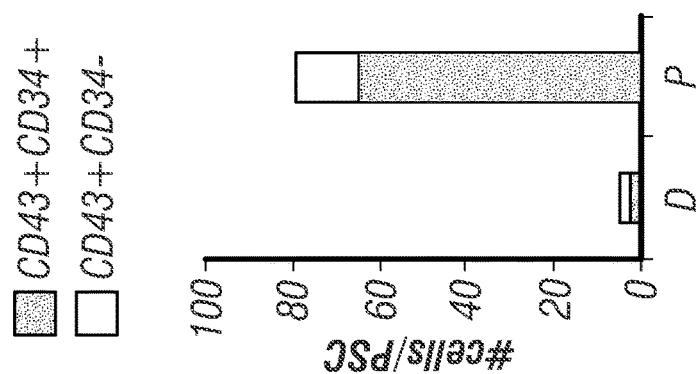
Figure 1C:
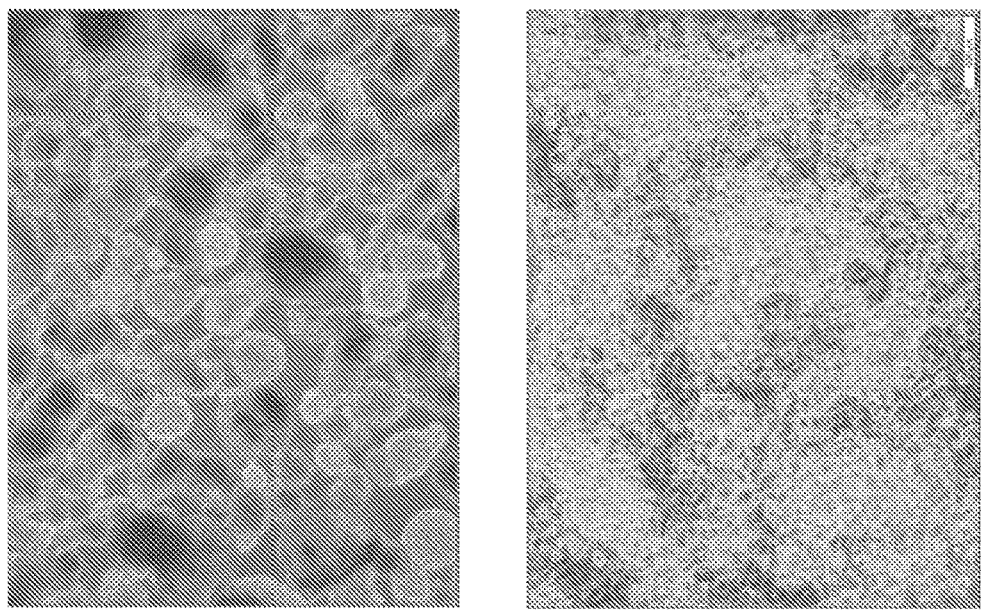
Figure 1C:
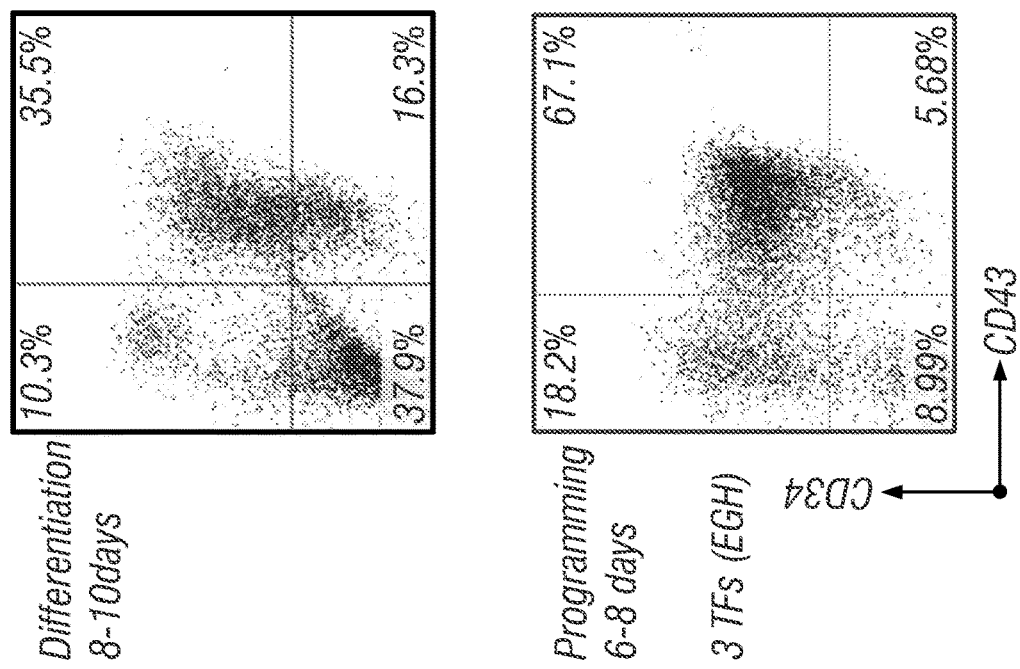

Non-modified and CAR-modified PSCs were differentiated to CD34$^+$ T/NK progenitors through cytokine-directed differentiation (1C, E11) or EGH-induced programming (A16) (FIGS. 1A-B). Isolated CD34$^+$ progenitors were further differentiated to CD3$^+$ T (1C, E11) and CD3-CD56$^+$ NK (A16) cells using 4 week hypoxic culture on the DLL4/retronectin-coated plates in StemSpan SFEM (Stem Cell Technologies) supplemented with ascorbic acid magnesium phosphate (0.25 mM), nicotinamide (2 mM) and cytokines (SCF, TPO, FLT3L, IL7, IL2). In parallel T/NK cultures, mitomycin C-treated Daudi cells (132-microglobulin deficient HLA class I negative CD19+B lymphoblastoid cell line) were added during last 2 weeks of differentiation as a source of antigen (CD19)-specific CAR activation. Generated T/NK cells were designated as follows: 1C or E11-derived T cells—T, CAR-T, CAR-T/Ag (Daudi co-culture); A16-derived NK cells—NK, CAR-NK, CAR-NK/Ag (Daudi co-culture).

CAR expression throughout differentiation stages was evaluated by flow cytometry using protein L staining. CD3$^+$ T cells were co-stained with lambda chain mouse anti-human CD3 mAb (clone SP34-2). Following differentiation to T/NK cells, CAR expression was significantly silenced, however, CAR-positive T and NK cells could be selectively expanded after activation culture with CAR-specific antigen (Ag; co-culture with CD19$^+$ Daudi cells).

The cytotoxic function of PSC-derived T (1C) and NK (A16) cells was evaluated by an in vitro cytotoxicity assay using luciferase-expressing CD19$^+$ Daudi and Raji target cells. Targets were incubated with T/NK effectors 24 hours at 1:1 ratio and luciferase activity was quantitated in culture lysates by Steady-Glo luciferase assay system (Promega). Percent cytotoxicity was calculated by the formula: $(1-(ET/T))\times100$, where ET-effectors+targets culture, T—targets only.

Figure 3A:
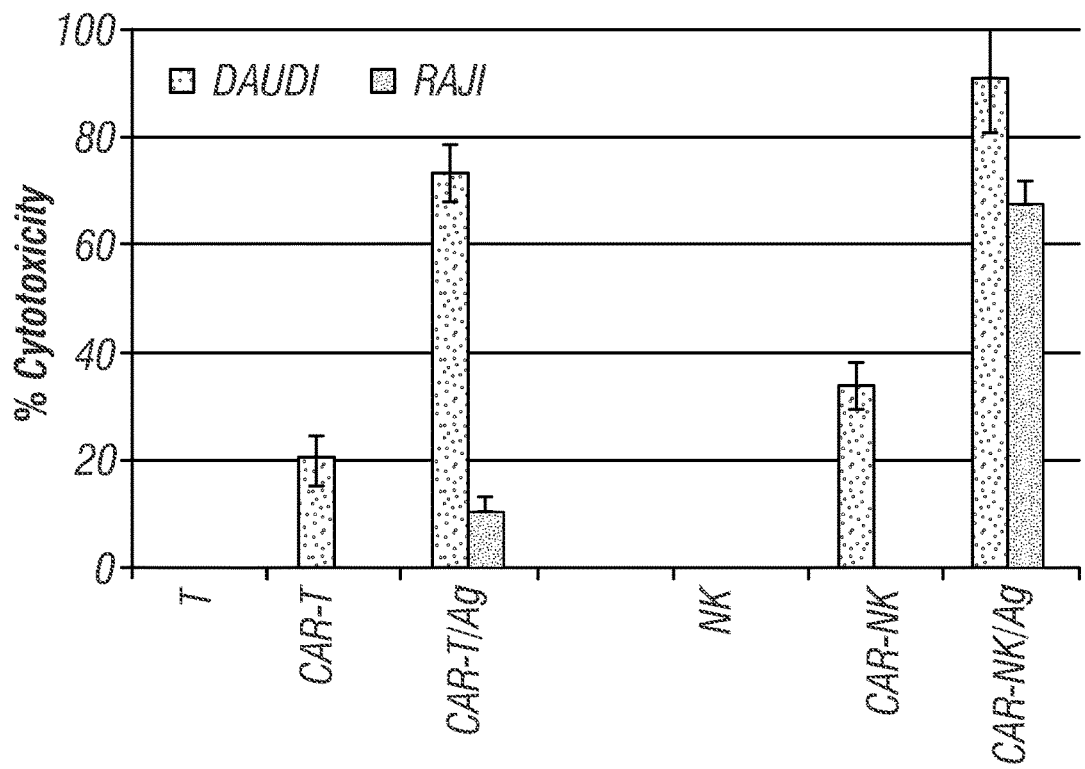
FIGS. 3A-B: In vitro anti-CD19 CAR-mediated cytotoxicity in PSC-derived T/NK cells.

While non-modified T/NK cells were lacking any detectable activity, both CAR-expressing T (1C) and NK (A16)

cells displayed cytotoxicity against the CD19+ targets. CAR-dependent cytotoxic activity was significantly enhanced after 2 week T/NK co-culture with CD19+ target (Daudi) cells (CAR/Ag variant) (FIG. 3A).

Figure 3B:
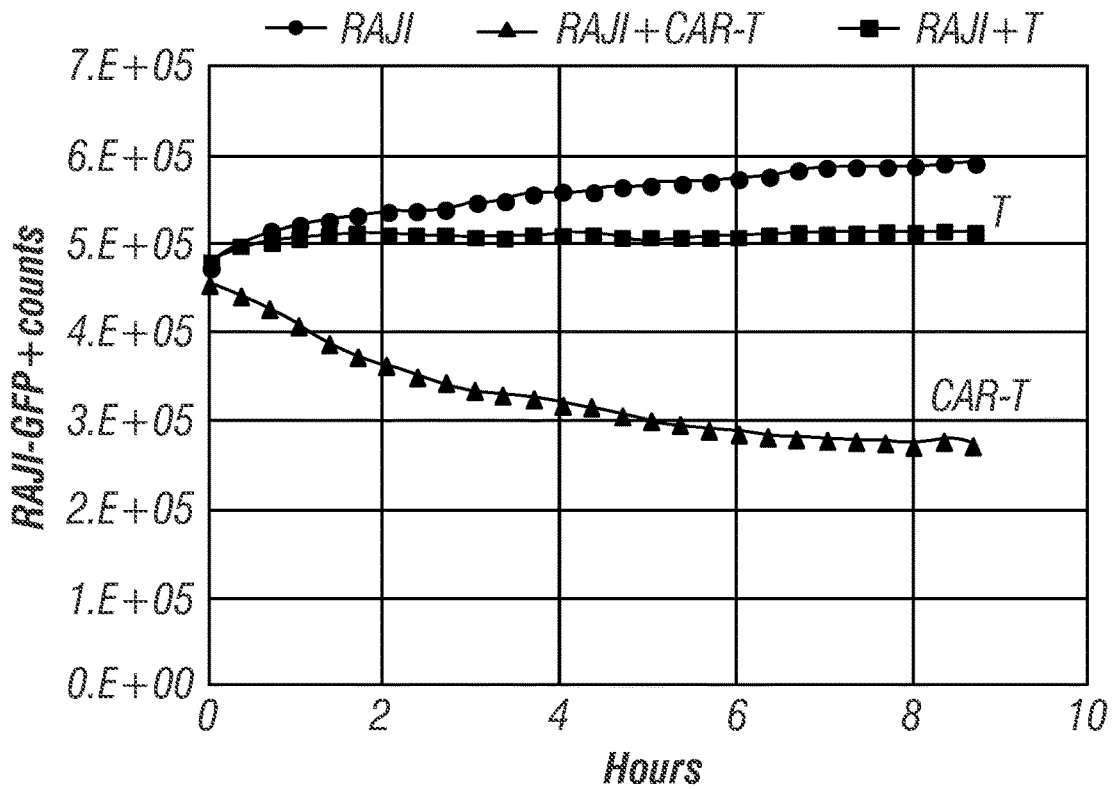

The cytolytic potential of CAR-T cells was confirmed by real-time target cell counting using Incucyte S3 live-cell analysis system (Essen Bioscience). GFP-expressing CD19+ Raji target cells were incubated with non-modified and CAR-transfected PSC (E11 TiPSC)-derived T cells at a 1:1 ratio. Time-lapse imaging and counting of GFP+ Raji cells was performed during 9 hours. A significant decrease of viable (GFP+) Raji cells was detected in culture with CAR-T cells only (FIG. 3B).

Figure 4:
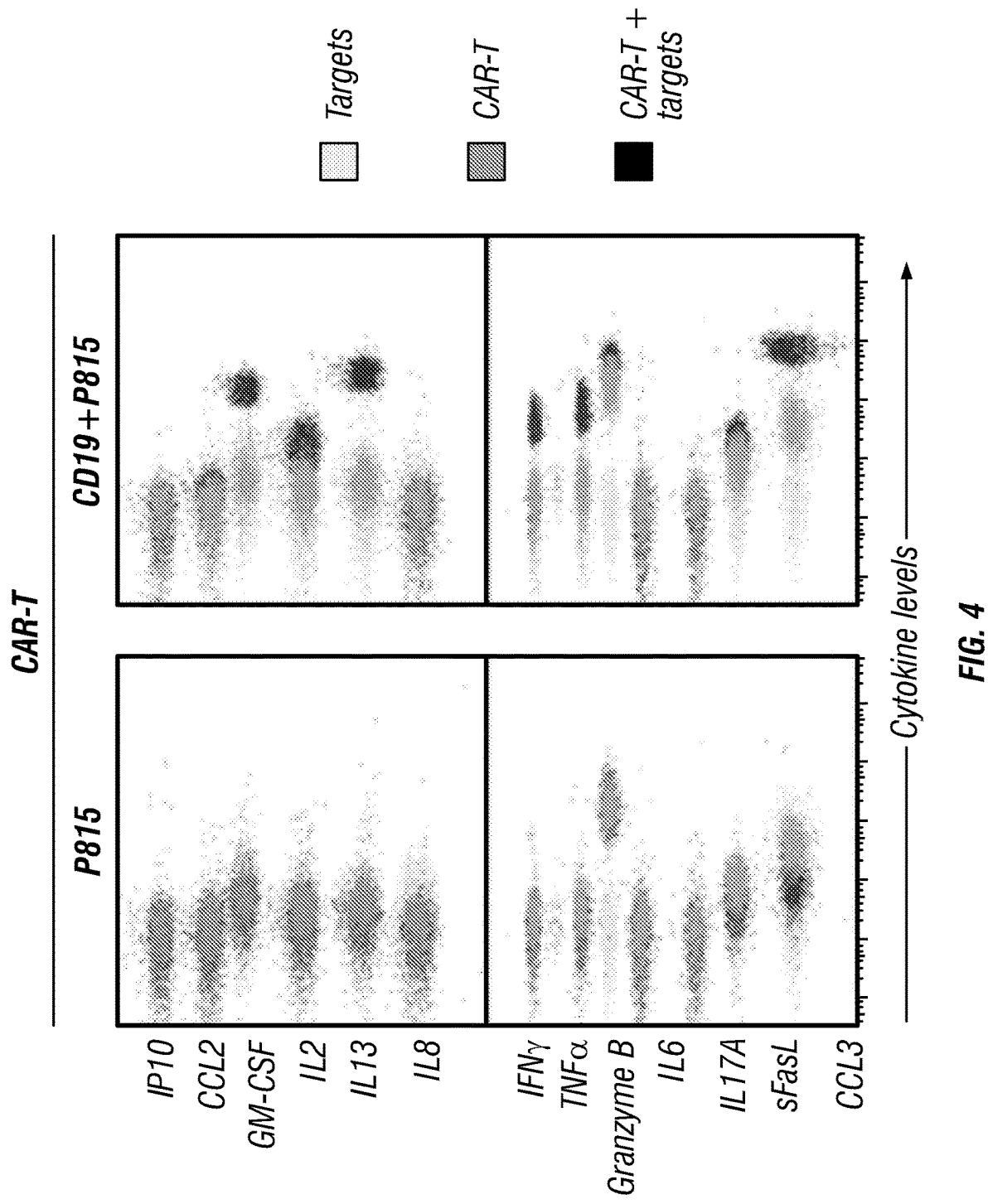
FIG. 4: In vitro anti-CD19 CAR-induced cytokine production in PSC-derived T/NK cells.

CAR-T cells that were generated by the 2 week T/NK differentiation followed by 1 week of anti-CD3 induced T cell expansion cultures from PSC (E11 TiPSC)-derived CD34+ HPCs were incubated 24 hours with mouse P815 mastocytoma cells transfected with human CD19 antigen (CD19+ P815) and non-transfected P815 to evaluate CAR-induced and constitutive cytokine production, respectively. Cytokines were measured in culture supernatants using LEGENDplex flow cytometry multiplex cytokine assay (BioLegend) (FIG. 4). CAR-T cells demonstrated specific CAR-induced production of IFNγ, TNFα, IL2, IL13 and GM-CSF. Cytotoxic properties of PSC-derived CAR-T cells were also revealed by constitutive Granzyme B secretion.

Figure 5A:
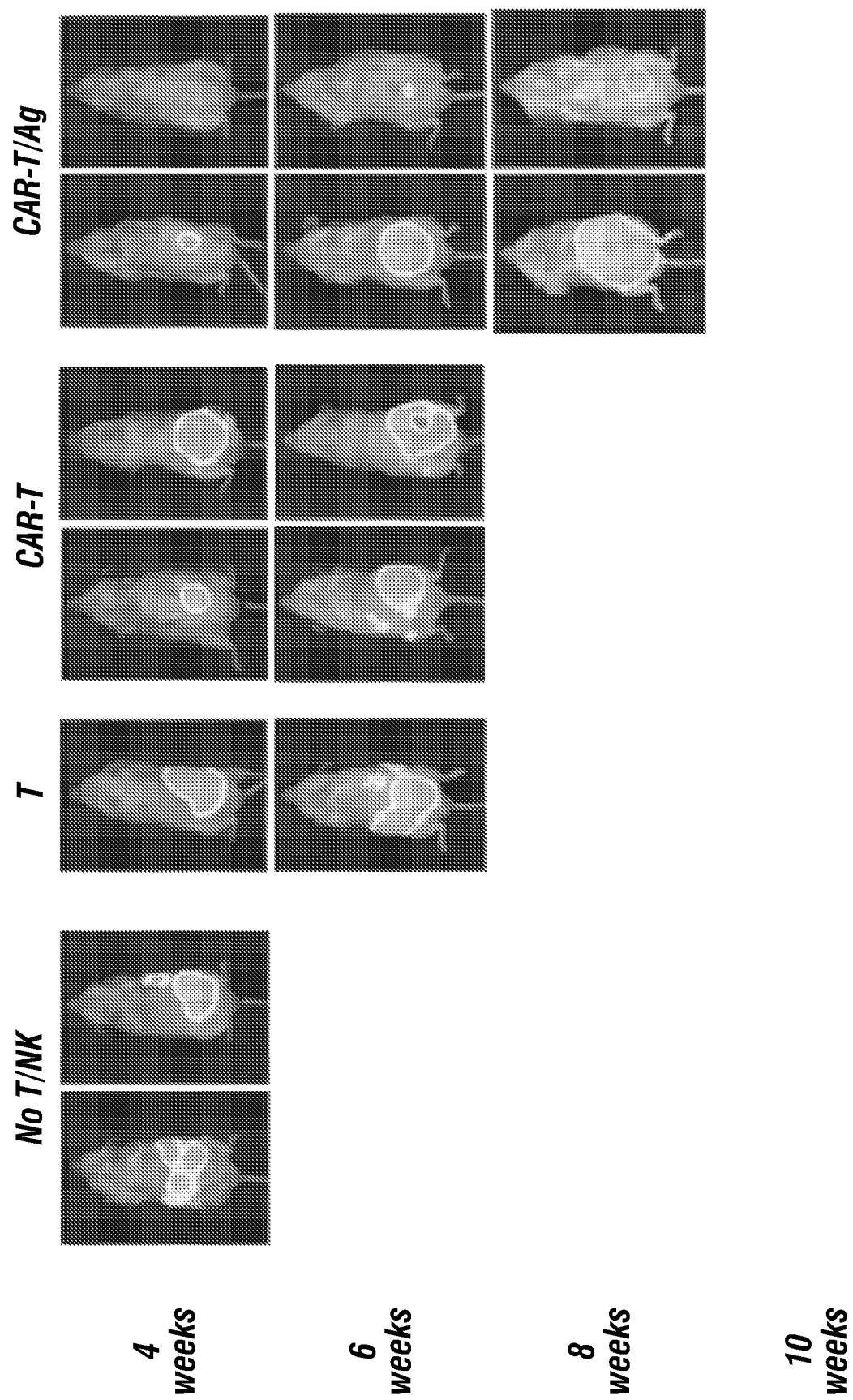
FIGS. 5A-5B: In vivo oncolytic potential of PSC-derived CAR-T/NK cells.
Figure 5A:
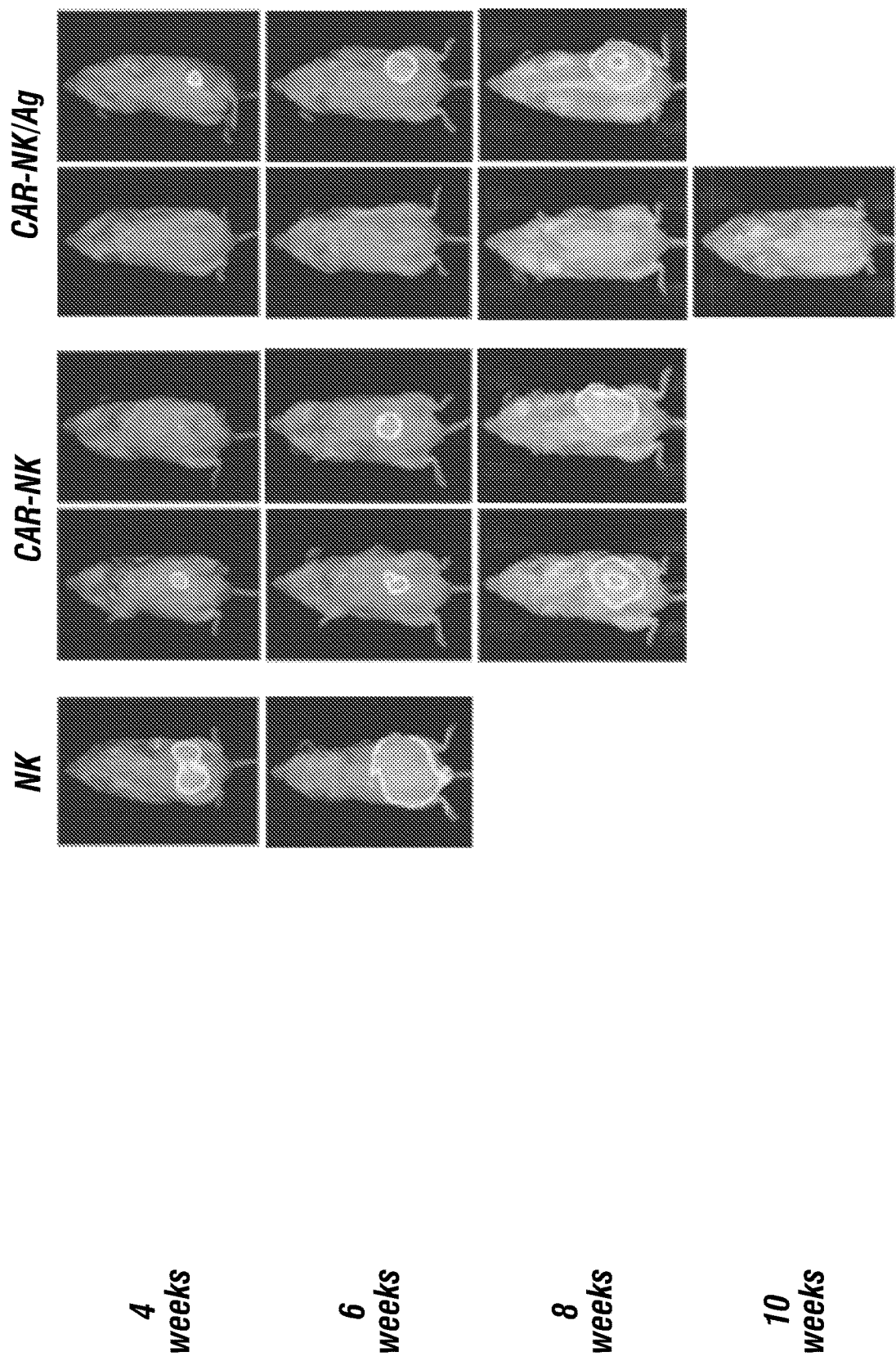
Figure 5B:
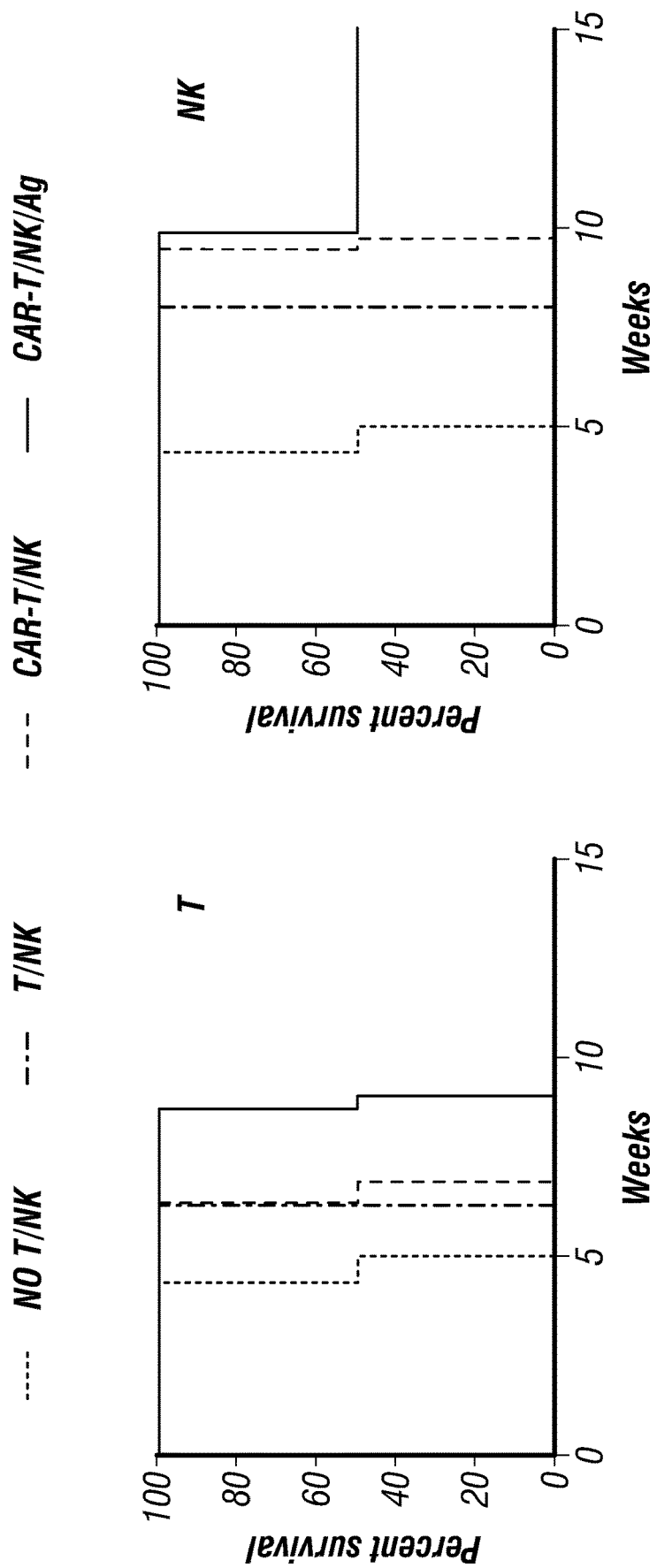

To test the efficacy of the CAR-T cells in vivo, 8-week old NSG mice were intra-peritoneally (ip) injected with $5 \times 10^4$ luciferase-expressing Raji cells. On the next day (day 1), T (1C-derived) and NK (A16-derived) cells were injected (ip) at a dose of $10^7$/mouse. T/NK injections were repeated on day 3 and 5. During T/NK injections (day 1-5), all mice were additionally injected (ip) with IL2 and IL15 cytokine combination (both at 500 ng/mouse). Tumor progression in mice was monitored by in vivo bioluminescent imaging every 2 weeks (FIG. 5A). Anesthetized mice injected (ip) with 150 mg/kg InVivo-Glo luciferin (Promega) were analyzed within 15 min after luciferin injection using Pearl Trilogy in vivo imager (LiCor). Survival curves in the different groups of mice treated either with PSC-derived T (1C) or NK (A16) cells are shown in FIG. 5B.

The tumors detected at 2 weeks were significantly suppressed, and average mice survival was ~2× prolonged by one treatment course (3 injections with 2 day intervals) with CAR-expressing PSC-derived T or NK cells. The in vivo oncolytic potential can be significantly improved by prior co-culture of CAR-expressing PSC-derived T or NK cells with antigen-positive tumor cells in vitro.

Example 2—Methods of Directed Differentiation

PCS Differentiation to CD34+ Lympho-Hematopoietic Progenitors:

The T-cell derived PSCs of Example 1 (1C and E11 TiPSCs derived from peripheral blood T cells by retroviral and episomal reprogramming, respectively) were differentiated to CD34+ hematopoietic progenitors through aggregate suspension culture. PSCs were maintained under feeder-free conditions on the Matrigel™- or Vitronectin-coated 6-well plates in Essential 8 (E8) medium. Aggregates were made from sub-confluent PSCs (<80% confluence) at a density of 0.5 million cells per ml in E8 medium supplemented with 2 µM CHIR99021 (GSK-3 inhibitor) and 5 µM blebbistatin (myosin-II inhibitor). Aggregate formation was performed during 6 hours culture in the ultra-low attachment (ULA) flasks under continuous agitation on the rocker platform at 15-20 rpm (including all subsequent culture steps).

Culture with preformed cell aggregates was gradually transferred to serum-free hematopoietic differentiation medium (HDM: 50% IMDM, 50% Hams F12 medium, 100 µg/ml polyvinyl alcohol, 100 µg/ml recombinant human serum albumin, 1x non-essential amino acid supplement (Invitrogen), 0.1× chemically-defined lipid supplement (Invitrogen), 125 µM ascorbic acid 2-phosphate magnesium, 0.25 µM linoleic acid, trace element supplements A (0.3×), B (0.2×) and C (0.1×) (Corning), 5 mM sodium chloride, 100 µM monothioglycerol, 20 µM ethanolamine, 100 ng/ml heparin, and 10 ng/ml IGF1) supplemented with 2 µM CHIR99021, 50 ng/ml VEGF and 50 ng/ml FGF2 by additions of equal medium volumes at 6 and 24 hours. On day 2, cell aggregates were settled by sedimentation during 15 minutes, medium was aspirated and cultures were transferred to HDM supplemented with hematopoietic mesoderm inducing cytokines—25 ng/ml BMP4, 50 mg/ml VEGF and 50 ng/ml FGF2. Cultures were continued for 3 days with complete medium change every day.

To support differentiation and expansion of hematopoietic CD34+ progenitors, cell aggregates were further transferred to HDM supplemented with hematopoietic supportive cytokines—50 ng/ml SCF, 50 ng/ml TPO, 20 ng/ml FLT3L and 20 ng/ml IL-3. Cultures were continued for 3-5 days with complete medium change every day. To improve the hematopoietic transition process, the following enhancing components can be added: IL11 (5-20 ng/ml), 8Br-cAMP (100-300 µM), and/or VEGF (20-50 ng/ml).

HPCs identified in suspension as floating individual cells or small clusters were harvested after 2+3+3-5 day differentiation process (total 8-10 days). HPCs were isolated by filtration of entire differentiation culture through 70 µm and 30 µm cell strainers (Corning). HPCs collected from filtrate by centrifugation were washed once in HDM and resuspended in TCDM (T cell differentiation medium). To enrich HPCs with T/NK potential, isolation of the CD34+ HPC fraction can be performed by magnet-activated cell sorting (MACS) using direct CD34 microbeads (Myltenyi Biotec) according to recommendations from the manufacturer. HPCs were plated to T/NK differentiation cultures or cryopreserved for later use within 1 hour of isolation.

T/NK Differentiation Cultures:

For T/NK differentiation, non-tissue culture treated plastic plates were coated with Notch ligand hDLL4-Fc chimeric protein and retronectin diluted in PBS (at 0.5 µg/cm² each). Before cell plating, coating solution was aspirated, plates washed once with PBS and filled with 0.25 ml/cm² T cell differentiation medium (TCDM) consisting of StemSpan SFEM (Stem Cell Technologies), GlutaMax (1/100), ascorbic acid magnesium phosphate (250 µM), nicotinamide (2 mM) and cytokines SCF, TPO, FLT3L and IL7 (at 50 ng/ml each). PSC-derived HPCs were plated at 5000 cells/cm² density and cultured in hypoxic (5% 02) $CO_2$ incubator for 2 weeks with addition of equal TCDM culture volume on day 3 and exchanging a half culture volume every second following day. Total differentiated cells were harvested by gentle resuspension and collection of non-adherent cells followed by collection of loosely attached cells by 5-10 min treatment with PBS-EDTA (0.5 mM). To continue differentiation process and improve the yield of T/NK cells, T cell differentiation culture can be repeated by re-plating harvested cells to freshly-prepared DLL4/retronectin plates at 10000 cells/cm² density, until desired yield of T/NK cells is achieved. The efficiency of T/NK differentiation can also be improved by addition of following enhancing components to TCDM: CHIR99021 (1-3 µM), IL2 (2-10 ng/ml), IL12 (10-50 ng/ml).

T Cell Expansion Cultures:

For T cell expansion, non-tissue culture treated plates were coated with anti-CD3 mAb (clone OKT3), hDLL4-Fc and retronectin diluted in PBS (at 0.5 µg/cm$^2$ each). Before cell plating, coating solution was aspirated, plates washed once with PBS and filled with 0.25 ml/cm$^2$ T cell expansion medium (TCEM) consisting of StemSpan SFEM (Stem Cell Technologies), Glutamax (1/100), ascorbic acid magnesium phosphate (250 µM), nicotinamide (2 mM) and cytokines SCF, TPO, FLT3L, IL7 (at 50 ng/ml each) and IL2, IL15 (at 10 ng/ml each). IL21 (5-20 ng/ml) could also be added to improve expansion. Cells harvested from T/NK differentiation cultures were plated at 10000 cells/cm$^2$ density and cultured in hypoxic (5% 02) $CO_2$ incubator up to 2 weeks with addition of equal TCEM culture volume on day 3 and exchanging a half culture volume every second following day. Expanded T cells were harvested by gentle resuspension and collection of non-adherent cells.

Example 3—Characterization of Directed Differentiation Method

PSCs were first differentiated to CD34$^+$ HPCs in suspension cell aggregate culture through successive steps of WNT-induced differentiation priming, mesoderm induction and HPC differentiation during 8-10 days (FIG. 1B). The HPC fraction was isolated by filtration. No MACs sorting of CD34$^+$ HPCs was performed, although it may be optionally performed using direct CD34 paramagnetic beads (Myltenyi Biotec). HPCs were then transferred to human DLL4-Fc$^+$ retronectin coated plates for T/NK differentiation during 2-4 weeks. T cells could further be expanded during 1-2 weeks in culture on the anti-CD3 mAb (OKT3 clone) coated plates.

Figure 1D:
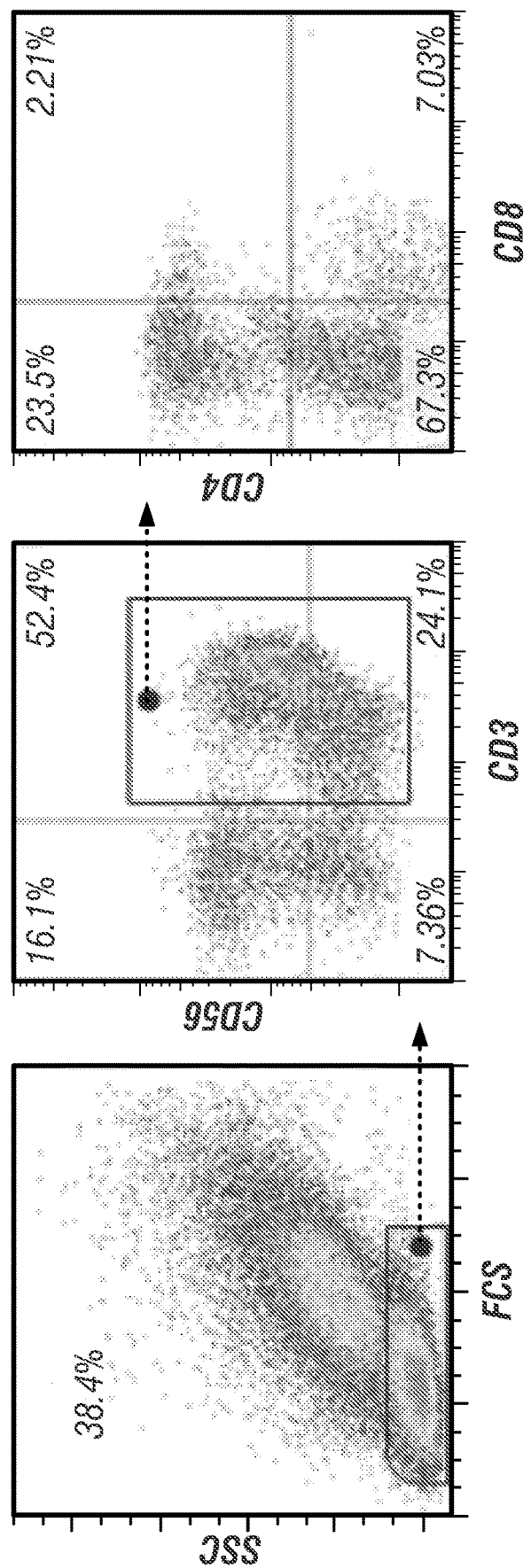

PSC (1C TiPSC)-derived CD34$^+$ cells after 2 weeks in T/NK differentiation conditions developed a typical lymphoid cell population defined by low FSC/SSC parameters (FIG. 1D, left dot-plot). This lymphoid population contained mostly CD3$^+$ T and CD56+CD3$^-$ NK cells (FIG. 1D, middle dot-plot). The T cell population included CD4$^+$ and CD8$^+$ single and double positive cells as well as a significant proportion of double negative cells (FIG. 1D, right dot plot).

Figure 1E:
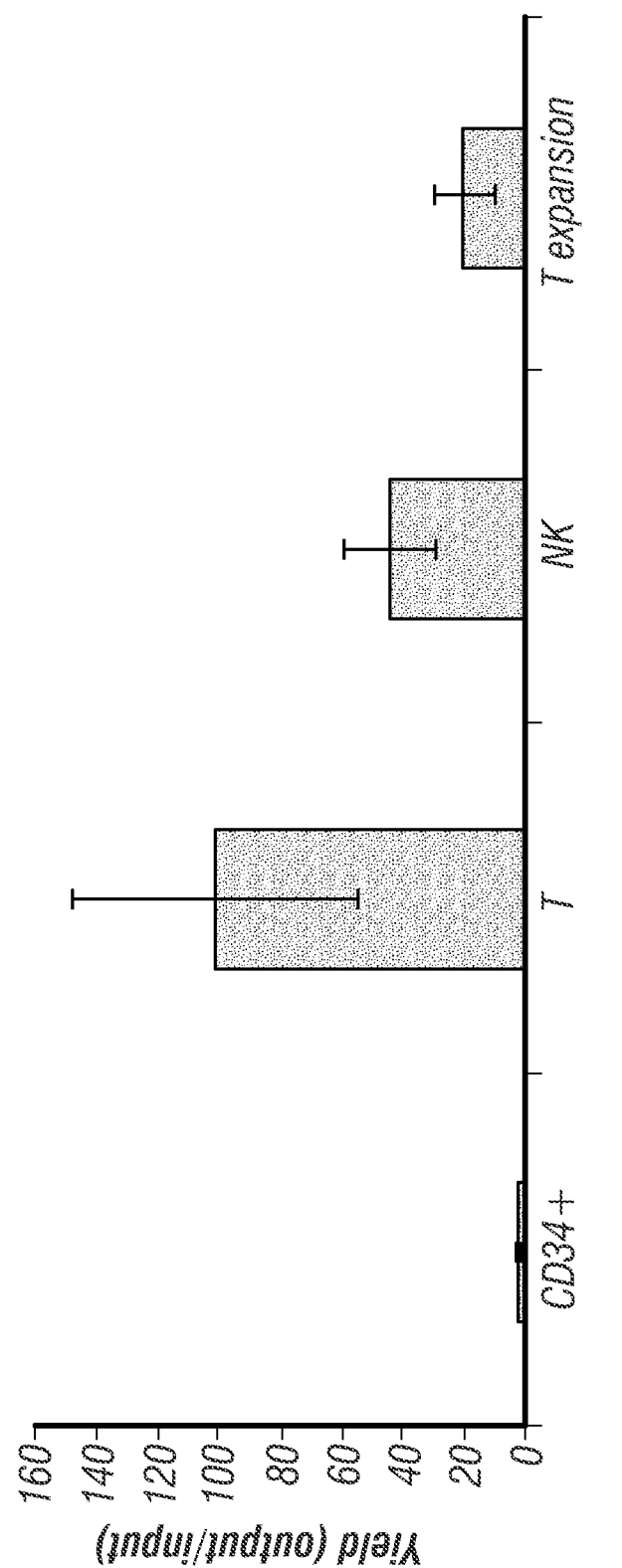

The yields of each respective cell type were calculated as a ratio of output to input absolute cell numbers at each stage of cell derivation. For example, 1.5 CD34+ HPC yield indicates that in average 1.5 (output) CD34$^+$ HPCs can be derived from 1 (input) PSC. Accordingly, 102 T cell yield indicates that 102 (output) T cells can be derived from 1 (input) CD34$^+$ HPCs (FIG. 1E).

Figure 1F:
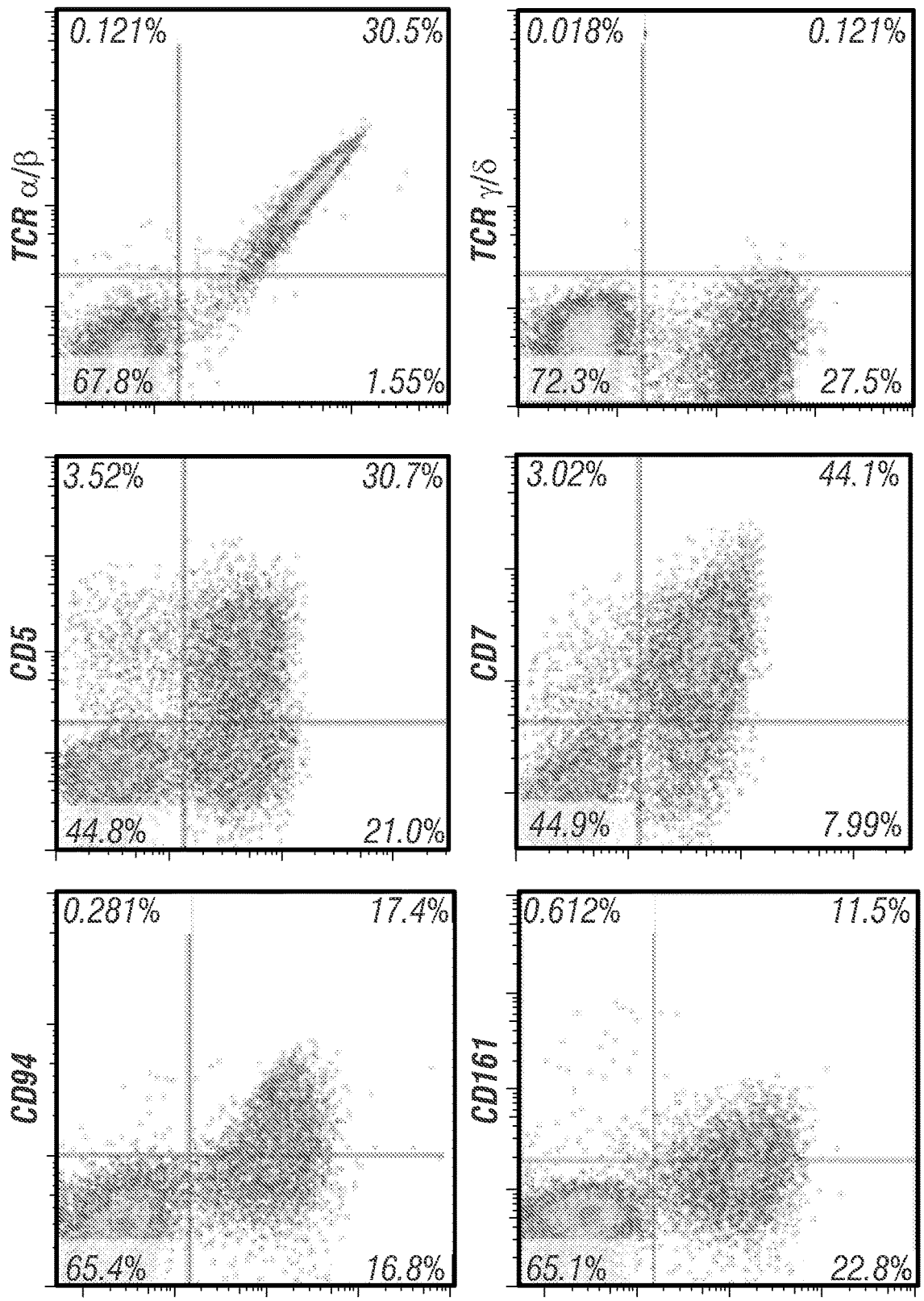
Figure 1F:
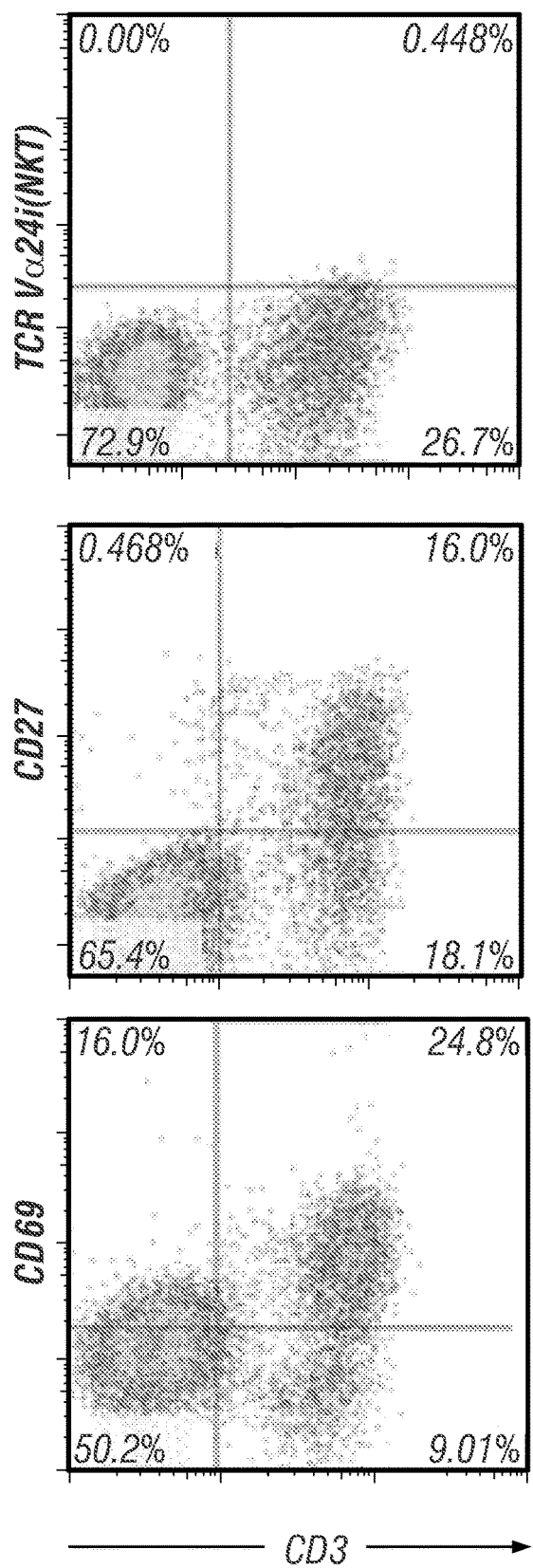

The PSC (1C TiPSC)-derived T cells (CD3$^+$) were differentiated and expanded during 4 weeks expressed a/β TCR (not γ/δ or invariant Vα24 NKT TCR) and typical T cell markers CD5, CD27, and CD7 (FIG. 1F). They also expressed cytotoxic T/NK associated (CD161, CD94) and activation (CD69) markers.

Figure 1G:
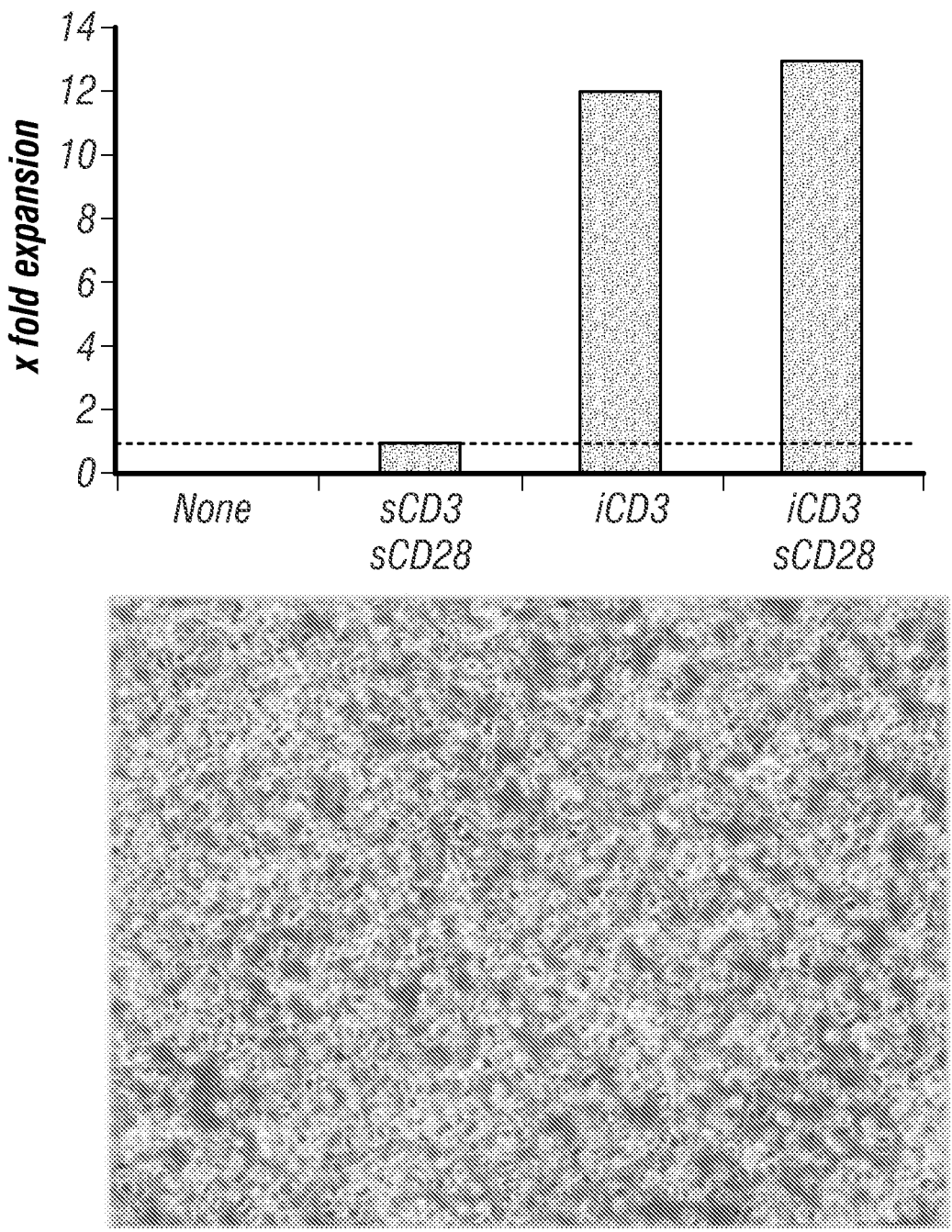
Figure 1G:
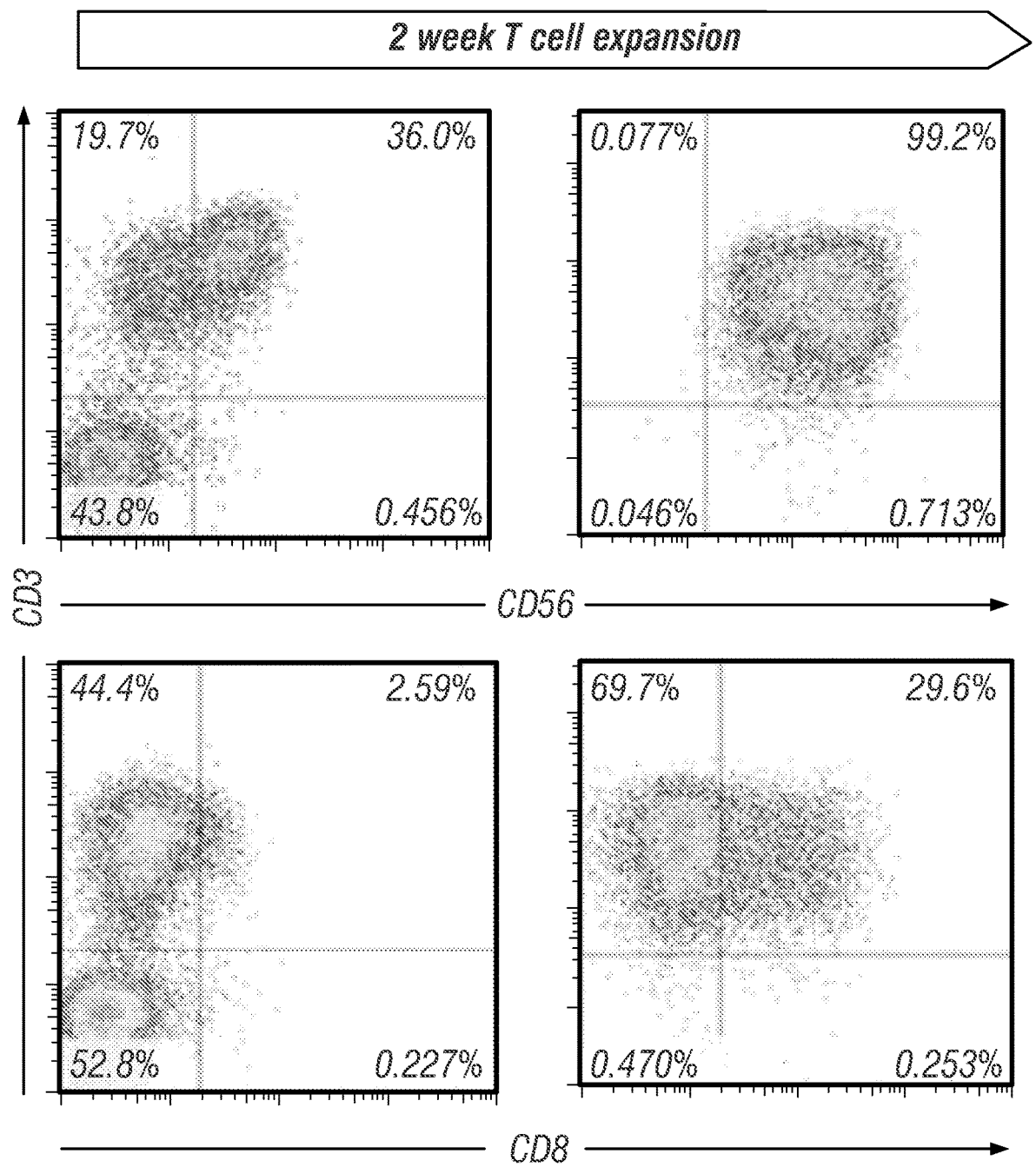
Figure 2:
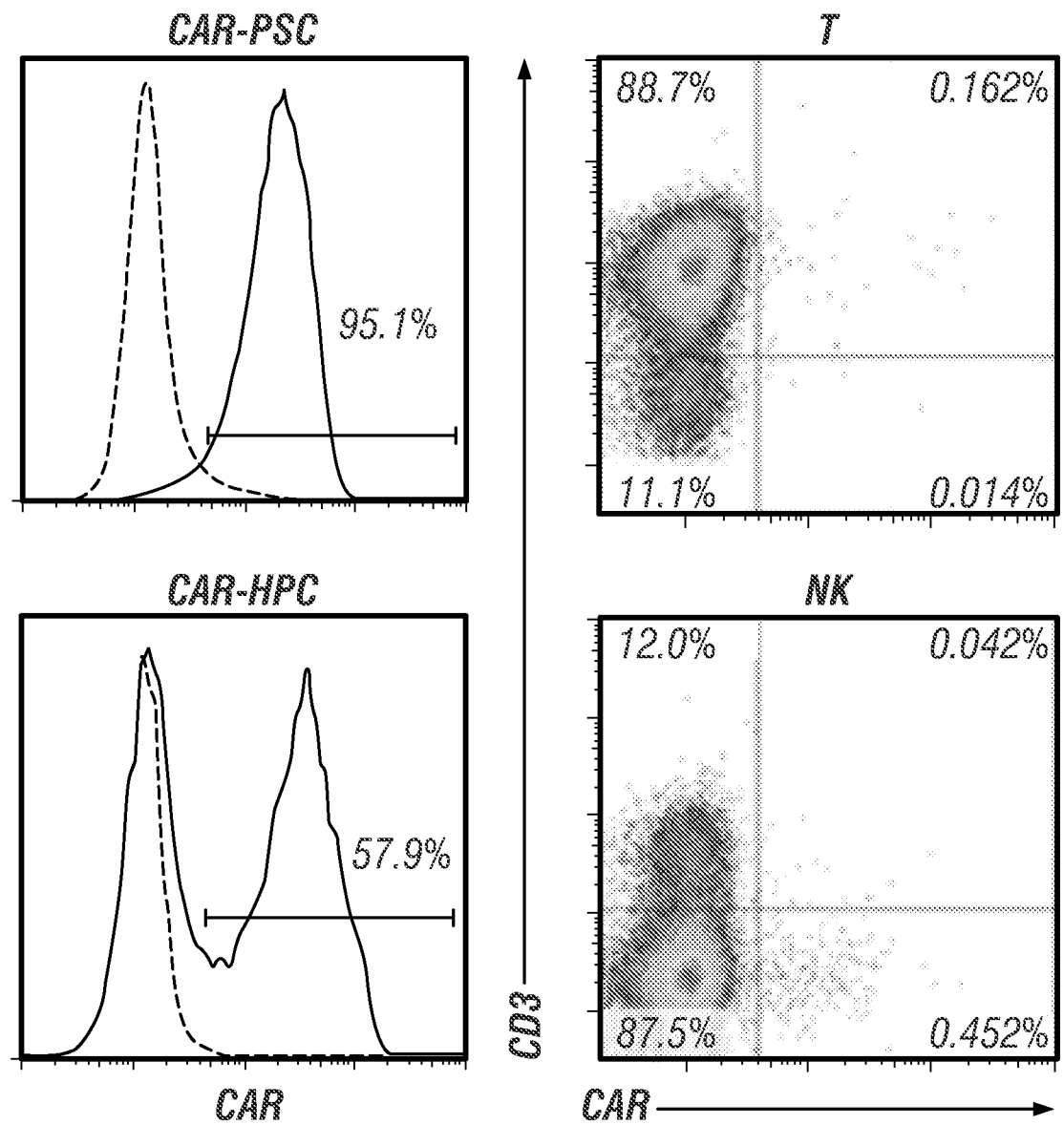
FIG. 2: CAR expression in PSC-derived T/NK cells. CAR expression throughout differentiation stages evaluated by flow cytometry using protein L staining. $CD3^+$ T cells were co-stained with lambda chain mouse anti-human CD3 mAb (clone SP34-2). CAR expression by E11 PSCs and E11-derived HPCs and T cells are shown.
Figure 2:
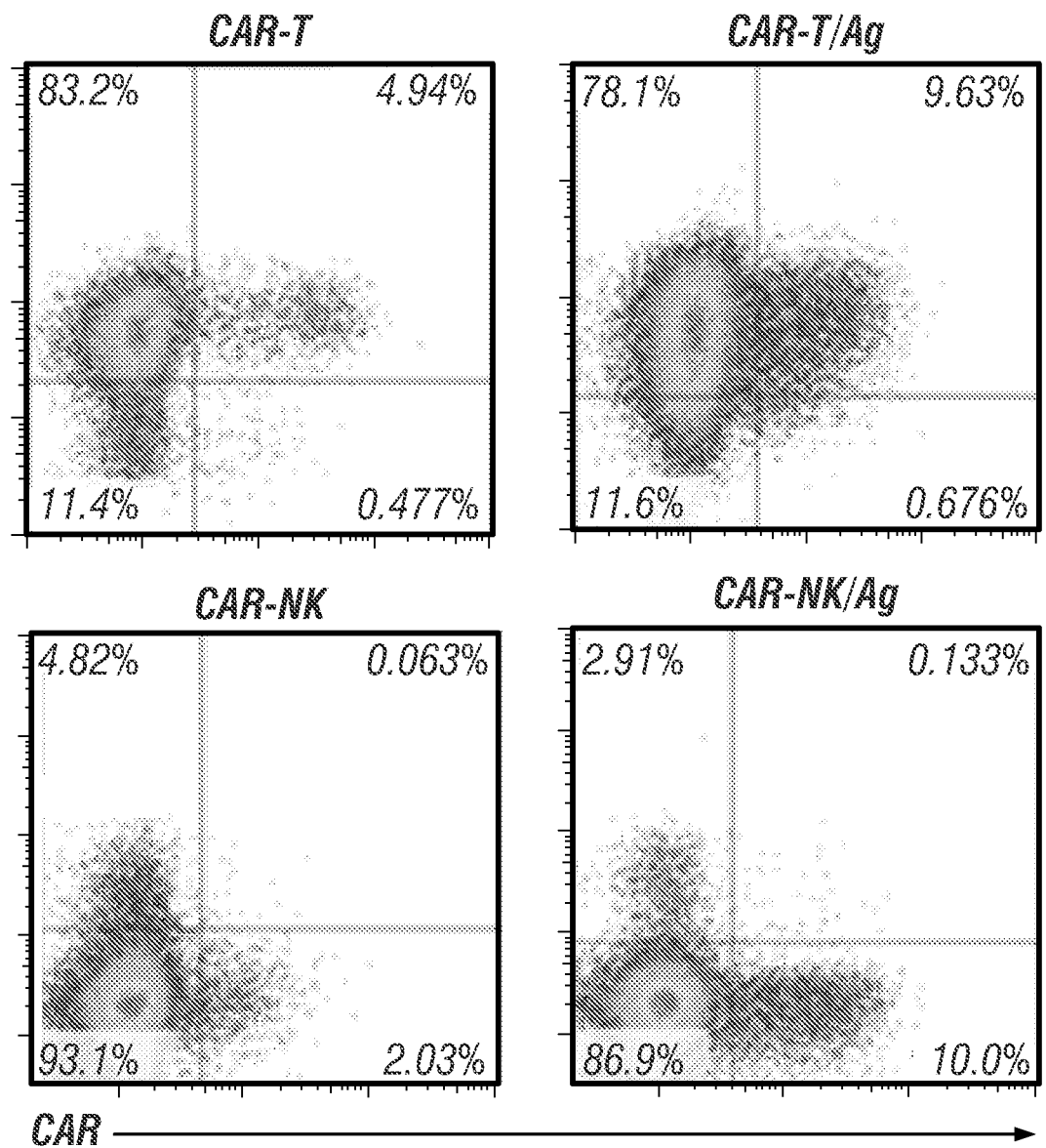

The immobilized anti-CD3 antibodies (iCD3) were minimally required and sufficient to achieve expansion of PSC-derived T cells (FIG. 1G, bar graph). Soluble stimulation with CD3 and CD28 mAbs (sCD3, sCD28) were not effective either alone or in combination (sCD3$^+$sCD28), or when added to iCD3 (iCD3$^+$sCD28). T cells proliferating in the expansion cultures acquired a characteristic morphology of irregularly shaped lymphoblasts (FIG. 1G, photograph). In contrast to the relatively heterogeneous input cell population, the cells harvested from the 2 week T cell expansion were essentially pure CD3$^+$ T cells, which also expressed CD56 and acquired CD8 expression (FIG. 1G, flow cytometry dot plots). Thus, the directed differentiation method efficiently produced T cells.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Akkina et al., *J. Virol.*, 70:2581-2585, 1996.
Alexander et al., *Proc. Nat. Acad. Sci. USA*, 85:5092-5096, 1988.
Ausubel et al., *Current Protocols in Molecular Biology*, Greene Publ. Assoc. Inc. & John Wiley & Sons, Inc., MA, 1996.
Biswas et al., *Annals NY Acad. Sci.*, 590:582-583, 1990.
Biswas, et al., *J. Clin. Microbiol.*, 29:2228-2233, 1991.
Blomer et al., *J Virol.*, 71(9):6641-6649, 1997.
Chen and Okayama, *Mol. Cell Biol.*, 7(8):2745-2752, 1987.
Chen et al., *Nature Methods* 8:424-429, 2011.
Chothia et al., *EMBO J.* 7:3745, 1988.
Doulatov et al., *Cell Stem Cell.* 10: 120-36, 2012.
Ercolani et al., *J Biol. Chem.*, 263:15335-15341, 1988.
Evans, et al., In: *Cancer Principles and Practice of Oncology*, Devita et al. (Eds.), Lippincot-Raven, NY, 1054-1087, 1997.
Fechheimer et al., *Proc Natl. Acad. Sci. USA*, 84:8463-8467, 1987.
Fraley et al., *Proc. Natl. Acad. Sci. USA*, 76:3348-3352, 1979.
Frisan et al., Epstein-Barr Virus Protocols, Part III, 125-127, 2001
Furie and Furie, *Cell* 53: 505-518, 1988.
Graham and Van Der Eb, *Virology*, 52:456-467, 1973.
International Publication NO. WO 2007/069666
International Publication No. PCT/US2016/057893
International Publication No. PCT/US2016/057899
International Publication No. WO 94/09699
International Publication No. WO 95/06128
International Publication No. WO 96/39487
Jores et al., *PNAS U.S.A.* 87:9138, 1990.
Kaeppler et al., *Plant Cell Reports* 9: 415-418, 1990.
Kaneda et al., *Science*, 243:375-378, 1989.
Karin et al. *Cell*, 36:371-379, 1989.
Kato et al, *J. Biol. Chem.*, 266:3361-3364, 1991.
Kim et al., *J. Virol.*, 66:3879-3882, 1992.
Knust et al, *EMBO J.* 761-766, 1987.
Ladi et al., *Nature Immunology*, 7: 338-343, 2006.
Langle-Rouault et al., *J. Virol.*, 72(7):6181-6185, 1998.

Lefranc et al., *Dev. Comp. Immunol.* 27:55, 2003.
Levitskaya et al., *Proc. Natl. Acad. Sci. USA*, 94(23):12616-12621, 1997.
Linnemann, C. et al. *Nat Med* 21, 81-85, 2015.
Ludwig et al., *Nat. Biotechnol.*, 24(2):185-187, 2006b.
Ludwig et al., *Nat. Methods*, 3(8):637-46, 2006a.
Macejak and Sarnow, *Nature*, 353:90-94, 1991.
Maniatis, et al., *Molecular Cloning, A Laboratory Manual*, Cold Spring Harbor Press, Cold Spring Harbor, N.Y., 1988.
Mann et al., *Cell*, 33:153-159, 1983.
Nabel et al., *Science*, 244(4910): 1342-1344, 1989.
Naldini et al., *Science*, 272(5259):263-267, 1996. Zufferey et al., *Nat. Biotechnol.*, 15(9):871-875,
Ng, *Nuc. Acid Res.*, 17:601-615, 1989.
Nicola, et al., *Blood*, 54:614-627, 1979.
Nicolas and Rubenstein, In: *Vectors: A survey of molecular cloning vectors and their uses*, Lab. Press, 2001.
Rodriguez and Denhardt, eds., Stoneham: Butterworth, pp. 494-513, 1988.
Nicolau and Sene, *Biochim. Biophys. Acta*, 721:185-190, 1982.
Nicolau et al., *Methods Enzymol.*, 149:157-176, 1987.
Notta et al., *Science*, 218-221, 2011.
Paskind et al., *Virology*, 67:242-248, 1975.
Patent Publication No. EP1507865
Pelletier and Sonenberg, *Nature*, 334(6180):320-325, 1988.
Potrykus et al., *Mol. Gen. Genet.*, 199(2):169-177, 1985.
Potter et al., *Proc. Natl. Acad. Sci. USA*, 81:7161-7165, 1984.
Quitsche et al., *J. Biol. Chem.*, 264:9539-9545, 1989.
Remington's Pharmaceutical Sciences 22$^{nd}$ edition, 2012.
Reubinoff et al., *Nat. Biotechnol.*, 18:399-404, 2000.
Richards et al., *Cell*, 37:263-272, 1984.
Rippe, et al., *Mol. Cell Biol.*, 10:689-695, 1990.
Sambrook and Russell, *Molecular Cloning: A Laboratory Manual*, 3rd Ed. Cold Spring Harbor 1997.
Suzuki et al, EMBO J. 6:1891-1897, 1987.
Takahashi et al., *Cell*, 131:861-872, 2007.
Temin, In: *Gene Transfer*, Kucherlapati (Ed.), NY, Plenum Press, 149-188, 1986.
Thomson and Marshall, *Curr. Top. Dev. Biol.*, 38:133-165, 1998.
Thomson and Odorico, *J. Trends. Biotechnol.*, 18:53-57, 2000.
Thomson et al. *Proc. Natl. Acad. Scie. USA*, 92:7844-7848, 1995.
Tur-Kaspa et al., *Mol. Cell Biol.*, 6:716-718, 1986.
U.S. patent application Ser. No. 08/464,599
U.S. patent application Ser. No. 12/715,136
U.S. Patent Application No. 61/088,054
U.S. Pat. No. 4,683,202
U.S. Pat. No. 5,030,015
U.S. Pat. No. 5,302,523
U.S. Pat. No. 5,322,783
U.S. Pat. No. 5,384,253
U.S. Pat. No. 5,464,765
U.S. Pat. No. 5,486,359
U.S. Pat. No. 5,538,877
U.S. Pat. No. 5,538,880
U.S. Pat. No. 5,550,318
U.S. Pat. No. 5,556,954
U.S. Pat. No. 5,563,055
U.S. Pat. No. 5,580,859
U.S. Pat. No. 5,589,466
U.S. Pat. No. 5,591,616
U.S. Pat. No. 5,610,042
U.S. Pat. No. 5,656,610
U.S. Pat. No. 5,702,932
U.S. Pat. No. 5,736,524
U.S. Pat. No. 5,780,448
U.S. Pat. No. 5,789,215
U.S. Pat. No. 5,843,780
U.S. Pat. No. 5,843,780
U.S. Pat. No. 5,928,906
U.S. Pat. No. 5,945,100
U.S. Pat. No. 5,981,274
U.S. Pat. No. 5,994,136
U.S. Pat. No. 5,994,624
U.S. Pat. No. 6,013,516
U.S. Pat. No. 6,200,806
U.S. Pat. No. 6,225,042
U.S. Pat. No. 6,355,479
U.S. Pat. No. 6,362,001
U.S. Pat. No. 6,544,518
U.S. Pat. No. 6,790,662
U.S. Pat. No. 7,029,913
U.S. Pat. No. 8,058,065
U.S. Pat. No. 8,129,187
U.S. Pat. No. 8,268,620
U.S. Pat. No. 8,268,620
U.S. Pat. No. 8,372,642
U.S. Pat. No. 8,741,648
U.S. Patent Publication No. 20020055144
U.S. Patent Publication No. 20050260186
U.S. Patent Publication No. 20060104968
U.S. Patent Publication No. 20090148425
U.S. Patent Publication No. 20090246875
U.S. Patent Publication No. 2010/0210014
U.S. Patent Publication No. 20120276636
U.S. Patent Publication No. 2014/0315304
U.S. Patent Publication No. 20160257939
Wilson et al., *Nature Reviews Immunology*, 9: 91-105, 2009.
Wilson et al., *Science*, 244:1344-1346, 1989.
Wong et al., *Gene*, 10:87-94, 1980.
Wynn, *Nature Immunology*, 6:1069-1070, 2005.
Xu et al., *Nat. Biotechnol.*, 19:971-974, 2001.
Yamanaka et al., *Cell*, 131(5):861-72, 2007.

What is claimed is:

1. A method of producing antigen-specific effector T cells and/or NK cells comprising:
   (a) engineering induced pluripotent stem cells (iPSCs) to express a chimeric antigen receptor (CAR), thereby producing CAR-iPSCs;
   (b) priming CAR-iPSCs for mesoderm induction by directed differentiation of the CAR-iPSCs to CD34$^+$ hematopoietic progenitor cells (HPCs) by generating embryoid bodies (EBs) in the presence of a ROCK inhibitor, a GSK-3 inhibitor, FGF2, and VEGF;
   (c) contacting the EBs with BMP-4, VEGF, and FGF2 to induce mesoderm induction;
   (d) differentiating the EBs in the presence of Flt-3 ligand, IL3, SCF, and TPO, thereby producing a population of HPCs comprising at least 40% CD34+CD43+ cells;
   (e) further differentiating the HPCs in the population to T cells and/or NK cells comprising culturing the HPC population on a fibronectin or fragment thereof and Notch DLL-4 coated surface in the presence of ascorbic acid and nicotinamide under hypoxic conditions; and
   (f) expanding the T cells and/or NK cells by co-culturing with antigen-specific target cells, thereby producing antigen-specific effector T cells and/or NK cells.

2. The method of claim 1, wherein the iPSCs are reprogrammed from T cells.

3. The method of claim 1, wherein differentiating of step (b) is essentially free of BMP4 and step (d) is essentially free of BMP4, VEGF and FGF2.

4. The method of claim 1, wherein the GSK-3 inhibitor is CHIR99021.

5. The method of claim 1, wherein the T cells are $CD4^+$ T cells, $CD8^+$ T cells, cytotoxic T cells, regulatory T cells, natural killer T cells, naïve T cells, memory T cells, or gamma delta T cells.

6. The method of claim 1, wherein step (b) further comprises selecting for cells that express CD34 and CD43 prior to differentiating to antigen-specific T cells and/or NK cells.

7. The method of claim 6, wherein the cells that express both CD34 and CD43 comprise at least 65 percent of the total cell population.

8. The method of claim 1, wherein at least 5 percent of the HPCs express the CAR.

9. The method of claim 1, wherein the culture in step (e) further comprises SCF, FLT-3 ligand, TPO, and IL7.

10. The method of claim 9, wherein the culture of step (e) further comprises a GSK-3 inhibitor, IL-2, and/or IL-12.

11. The method of claim 1, wherein expanding the T cells of step (f) further comprises culturing the antigen-specific T cells in the presence of anti-CD3 antibody, IL-2, and IL-15.

12. The method of claim 1, wherein at least 1.5 percent of the differentiated $CD34^+$ HPCs are $CD3+CAR^+$ T cells.

13. The method of claim 1, wherein at least 5 percent of the antigen-specific effector T cells display cytotoxic activity against target cells.

14. The method of claim 1, wherein the iPSCs are homozygous for one or more of the loci alleles HLA-A, HLA-B, HLA-C, HLA-DR, HLA-DP or HLA-DQ.

15. The method of claim 1, wherein expanding comprises culturing the antigen-specific T cells in the presence of anti-CD3 antibody, FLT3-ligand, IL-7, IL-2, IL-15, and/or IL-21.

16. The method of claim 1, wherein the method comprises culturing the cells under defined, feeder-free conditions.

17. The method of claim 11, wherein the expanding the T cells produce a cell population comprising $CD3^+$ T cells.

18. The method of claim 1, wherein the fibronectin fragment is retronectin.

19. The method of claim 1, wherein the population of HPCs comprise at least 45% CD34+CD43+ cells.

20. The method of claim 19, wherein the population of HPCs comprise at least 50% CD34+CD43+ cells.

21. The method of claim 20, wherein the population of HPCs comprise at least 60% CD34+CD43+ cells.

22. The method of claim 21, wherein the population of HPCs comprise at least 70% CD34+CD43+ cells.

* * * * *